(12) United States Patent
Bernstein et al.

(10) Patent No.: US 12,112,854 B2
(45) Date of Patent: Oct. 8, 2024

(54) SOFTWARE APPLICATIONS RESIDING ON HANDHELD ANALYTE DETERMINING DEVICES

(71) Applicant: ABBOTT DIABETES CARE INC., Alameda, CA (US)

(72) Inventors: Daniel M. Bernstein, El Granada, CA (US); Brittany K. Bradrick, San Francisco, CA (US); Erwin S. Budiman, Fremont, CA (US); Eric Davis, Castro Valley, CA (US); Timothy C. Dunn, San Francisco, CA (US); Mani Gopal, Hillsborough, CA (US); Wesley S. Harper, Alameda, CA (US); Gary A. Hayter, Oakland, CA (US); Steve Scott, Pleasanton, CA (US); Todd Winkler, Cameron Park, CA (US); Howard Wolpert, Brookline, MA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 186 days.

(21) Appl. No.: 15/901,791

(22) Filed: Feb. 21, 2018

(65) Prior Publication Data
US 2018/0242891 A1    Aug. 30, 2018

Related U.S. Application Data

(63) Continuation of application No. 13/984,815, filed as application No. PCT/US2011/066585 on Dec. 21, 2011, now Pat. No. 9,913,599.
(Continued)

(51) Int. Cl.
*G16H 80/00*    (2018.01)
*A61B 5/145*    (2006.01)
(Continued)

(52) U.S. Cl.
CPC ......... *G16H 80/00* (2018.01); *A61B 5/14532* (2013.01); *G16H 10/60* (2018.01);
(Continued)

(58) Field of Classification Search
CPC ........................ A61B 5/14532; A61B 5/7275
See application file for complete search history.

(56) References Cited

U.S. PATENT DOCUMENTS

| 4,545,382 A | 10/1985 | Higgins et al. |
| 4,711,245 A | 12/1987 | Higgins et al. |
(Continued)

FOREIGN PATENT DOCUMENTS

| WO | WO PCT/US2011/066585 | 6/2012 |

OTHER PUBLICATIONS

Barker, N., "A Practical Introduction to the Bootstrap Using the SAS System", SAS Conference Proceedings, 2005, Paper PK02, 17 pages.
(Continued)

*Primary Examiner* — Carrie R Dorna
*Assistant Examiner* — Karen E Toth
(74) *Attorney, Agent, or Firm* — ONE LLP

(57) ABSTRACT

Presented herein is a handheld analyte measurement device. The analyte measurement device includes one or more software applications to help the user manager their diabetes. Embodiments and descriptions of the various applications are provided below in conjunction with the handheld analyte measurement device.

12 Claims, 33 Drawing Sheets

Related U.S. Application Data

(60) Provisional application No. 61/485,840, filed on May 13, 2011, provisional application No. 61/442,092, filed on Feb. 11, 2011.

(51) Int. Cl.
*G16H 10/60* (2018.01)
*G16H 15/00* (2018.01)
*G16H 20/00* (2018.01)
*G16H 40/63* (2018.01)
*G16H 40/67* (2018.01)
*G16H 50/20* (2018.01)

(52) U.S. Cl.
CPC ............. *G16H 20/00* (2018.01); *G16H 40/67* (2018.01); *G16H 50/20* (2018.01); *G16H 15/00* (2018.01); *G16H 40/63* (2018.01)

(56) References Cited

U.S. PATENT DOCUMENTS

| | | |
|---|---|---|
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,356,249 A | 10/1994 | Heller et al. |
| 5,509,410 A | 4/1996 | Hill et al. |
| 5,536,249 A | 7/1996 | Castellano et al. |
| 5,543,236 A | 8/1996 | Heller et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 5,925,021 A | 7/1999 | Castellano et al. |
| 6,071,391 A | 6/2000 | Gotoh et al. |
| 6,103,033 A | 8/2000 | Say et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,281,006 B1 | 8/2001 | Heller et al. |
| 6,284,478 B1 | 9/2001 | Heller et al. |
| 6,299,757 B1 | 10/2001 | Feldman et al. |
| 6,302,844 B1 * | 10/2001 | Walker .................. G16H 20/30 600/300 |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,616,819 B1 | 9/2003 | Liamos et al. |
| 6,618,934 B1 | 9/2003 | Feldman et al. |
| 6,638,716 B2 | 10/2003 | Heller et al. |
| 6,650,471 B2 | 11/2003 | Doi |
| 6,654,625 B1 | 11/2003 | Say et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,932,892 B2 | 8/2005 | Chen et al. |
| 6,932,894 B2 | 8/2005 | Mao et al. |
| 6,942,518 B2 | 9/2005 | Liamos et al. |
| 7,041,468 B2 | 5/2006 | Drucker et al. |
| 7,167,818 B2 | 1/2007 | Brown |
| 7,299,082 B2 | 11/2007 | Feldman et al. |
| 7,766,829 B2 | 8/2010 | Sloan et al. |
| 7,866,026 B1 | 1/2011 | Wang et al. |
| 8,262,874 B2 | 9/2012 | Forrow et al. |
| 8,514,086 B2 | 8/2013 | Harper et al. |
| 8,601,465 B2 | 12/2013 | Bernstein et al. |
| 9,913,599 B2 | 3/2018 | Bernstein et al. |
| 2003/0208110 A1 | 11/2003 | Mault et al. |
| 2004/0054263 A1 | 3/2004 | Moerman |
| 2004/0186365 A1 | 9/2004 | Jin et al. |
| 2004/0254434 A1 | 12/2004 | Goodnow et al. |
| 2005/0101841 A9 | 5/2005 | Kaylor et al. |
| 2005/0182306 A1 | 8/2005 | Sloan |
| 2006/0025662 A1 | 2/2006 | Buse et al. |
| 2006/0040402 A1 | 2/2006 | Brauker et al. |
| 2006/0091006 A1 | 5/2006 | Wang et al. |
| 2006/0173260 A1 | 8/2006 | Gaoni et al. |
| 2006/0224141 A1 | 10/2006 | Rush et al. |
| 2006/0271565 A1 * | 11/2006 | Acevedo-Aviles .......................... G06F 16/24564 |
| 2007/0056858 A1 | 3/2007 | Chen et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2007/0227911 A1 | 10/2007 | Wang et al. |
| 2007/0233013 A1 | 10/2007 | Schoenberg |
| 2008/0066305 A1 | 3/2008 | Wang et al. |
| 2008/0081977 A1 | 4/2008 | Hayter et al. |
| 2008/0102441 A1 | 5/2008 | Chen et al. |
| 2008/0119705 A1 | 5/2008 | Patel et al. |
| 2008/0139910 A1 * | 6/2008 | Mastrototaro ......... G16H 40/63 600/365 |
| 2008/0148873 A1 | 6/2008 | Wang |
| 2008/0161666 A1 | 7/2008 | Feldman et al. |
| 2008/0234992 A1 | 9/2008 | Ray et al. |
| 2008/0249470 A1 | 10/2008 | Malave et al. |
| 2008/0267823 A1 | 10/2008 | Wang et al. |
| 2009/0054748 A1 | 2/2009 | Feldman |
| 2009/0054753 A1 | 2/2009 | Robinson et al. |
| 2009/0095625 A1 | 4/2009 | Forrow |
| 2009/0164251 A1 | 6/2009 | Hayter |
| 2009/0171589 A1 | 7/2009 | Kovatchev |
| 2009/0240127 A1 * | 9/2009 | Ray ........................ G16H 20/17 600/365 |
| 2009/0240128 A1 | 9/2009 | Mensinger et al. |
| 2009/0247857 A1 | 10/2009 | Harper et al. |
| 2009/0253970 A1 | 10/2009 | Bashan et al. |
| 2009/0255811 A1 | 10/2009 | Forrow et al. |
| 2009/0294277 A1 | 12/2009 | Thomas et al. |
| 2010/0081909 A1 | 4/2010 | Budiman et al. |
| 2010/0094251 A1 * | 4/2010 | Estes ...................... G16H 20/17 604/504 |
| 2010/0198034 A1 | 8/2010 | Thomas et al. |
| 2010/0198142 A1 | 8/2010 | Sloan et al. |
| 2010/0204557 A1 * | 8/2010 | Kiaie ..................... A61B 5/411 600/365 |
| 2010/0213057 A1 | 8/2010 | Feldman et al. |
| 2010/0222648 A1 | 9/2010 | Tan |
| 2010/0230285 A1 | 9/2010 | Hoss et al. |
| 2010/0256047 A1 | 10/2010 | Sieh et al. |
| 2010/0274592 A1 | 10/2010 | Nitzan et al. |
| 2010/0312577 A1 | 12/2010 | Goodnow et al. |
| 2010/0313105 A1 | 12/2010 | Nekoomaram et al. |
| 2010/0324392 A1 | 12/2010 | Yee et al. |
| 2010/0325868 A1 | 12/2010 | Wang et al. |
| 2010/0326842 A1 | 12/2010 | Mazza et al. |
| 2010/0331654 A1 * | 12/2010 | Jerdonek ............ A61B 5/14532 600/365 |

(56) References Cited

U.S. PATENT DOCUMENTS

| | | | |
|---|---|---|---|
| 2010/0332445 A1* | 12/2010 | Ray | G16H 40/63 706/54 |
| 2011/0015511 A1 | 1/2011 | Bousamra et al. | |
| 2011/0021889 A1 | 1/2011 | Hoss et al. | |
| 2011/0082484 A1 | 4/2011 | Saravia et al. | |
| 2011/0082711 A1* | 4/2011 | Poeze | A61B 5/14532 705/3 |
| 2011/0098548 A1 | 4/2011 | Budiman et al. | |
| 2011/0106011 A1 | 5/2011 | Cinar et al. | |
| 2011/0106126 A1 | 5/2011 | Love et al. | |
| 2011/0119080 A1 | 5/2011 | Hayter et al. | |
| 2011/0125530 A1 | 5/2011 | Drucker et al. | |
| 2011/0152830 A1 | 6/2011 | Ruchti et al. | |
| 2011/0160544 A1 | 6/2011 | Hayter | |
| 2011/0184264 A1 | 7/2011 | Galasso et al. | |
| 2011/0190603 A1 | 8/2011 | Stafford | |
| 2011/0191044 A1 | 8/2011 | Stafford | |
| 2011/0213225 A1 | 9/2011 | Bernstein et al. | |
| 2011/0256024 A1 | 10/2011 | Cole et al. | |
| 2011/0319729 A1 | 12/2011 | Donnay et al. | |
| 2012/0157801 A1 | 6/2012 | Hoss et al. | |
| 2014/0088392 A1 | 3/2014 | Bernstein et al. | |
| 2014/0142981 A1 | 5/2014 | Gopal et al. | |

OTHER PUBLICATIONS

Benton, D., et al., "Performance of the Parametric Bootstrap Method in Small Sample Interval Estimates", Adv. & Appl. in Stat., 2002, vol. 2, No. 3, pp. 269-285.

Nathan, D. M., et al., "Translating the A1C Assay Into Estimated Average Glucose Values", Diabetes Care, 2008, vol. 31, No. 8, pp. 1473-1478.

The Diabetes Control and Complications Trial Research Group, "The Effect of Intensive Treatment of Diabetes on the Development and Progression of Long-Term Complications in Insulin-Dependent Diabetes Mellitus", The New England Journal od Medicine, 1993, vol. 329, No. 14, pp. 977-986.

* cited by examiner

| 4 | Glucose control targets achieved for hypoglycemia, variability and mean glucose exposure. | |
|---|---|---|
| 3 | Reduce mean glucose exposure. | A. Both Day and Night above target.<br>   i. Day = Night<br>   ii. Night > Day<br>   iii. Day > Night |
| | | B. Night only above target. |
| | | C. Day only above target. |
| 2 | Reduce glucose volatility. | A. Both Day and Night above target. |
| | | B. Night only above target. |
| | | C. Day only above target. |
| 1 | Reduce hypoglycemia. | A. Both Day and Night above target. |
| | | B. Night only above target. |
| | | C. Day only above target. |
| 0 | Increase glucose monitoring. | Insufficient monitoring is available to assess control level. |

FIG. 2

| Assessment Schedule | Early Sleep 11pm-3am | Late Sleep 3am-7am | Morning 7am-11am | Midday 11am-4pm | Evening 4pm-11pm |
|---|---|---|---|---|---|
| Hypoglycemia | X | XX | | X | |
| Volatility | X | XX | | | XX |
| Excess Exposure | | X | XX | | XX |

X = Collect a measurement on 5 of 14 days.
XX = Collect a measurement on 10 of 14 days.

FIG. 15

| | | | |
|---|---|---|---|
| Walking/fasting | X | | |
| Pre-breakfast | X | X | |
| Post-breakfast | X | X | X |
| Pre-lunch | X | X | X |
| Post-lunch | | | |
| Pre-dinner | X | X | |
| Post-dinner | X | X | |

FIG. 16

SOFTWARE APPLICATIONS RESIDING ON HANDHELD ANALYTE DETERMINING DEVICES

CROSS-REFERENCE TO RELATED APPLICATIONS

This application is a continuation of U.S. application Ser. No. 13/984,815, filed Nov. 25, 2013, which is a national stage entry of PCT Appl. No. PCT/US2011/066585, filed Dec. 21, 2011, which claims priority to U.S. Provisional Application No. 61/442,092, filed Feb. 11, 2011, and U.S. Provisional Application No. 61/485,840, filed May 13, 2011, the disclosures of which are incorporated by reference herein in their entireties for all purposes. This application is related to U.S. Provisional Patent Application No. 61/442,063 filed on Feb. 11, 2011; U.S. Provisional Application No. 61/442,085 filed on Feb. 11, 2011; U.S. Provisional Application No. 61/486,117 filed on May 13, 2011; U.S. Provisional Application No. 61/442,093 filed on Feb. 11, 2011, and Application No. 61/442,097 filed on Feb. 11, 2011, the disclosures of which are all incorporated herein by reference in their entirety and for all purposes.

BACKGROUND OF THE INVENTION

The Field of the Invention

The present invention relates to handheld analyte measurement systems. More specifically, the present invention relates to a handheld analyte measurement device having one or more diabetes management applications.

Background

One tool used in diabetes management is an analyte meter. An analyte meter is typically used to measure the blood glucose level of a user based on a sample of blood. The process of using an analyte meter is not complicated, and is often performed several times a day. First, the user inserts an analyte test strip into a test strip port of the meter. The user then lances her finger to obtain a small sample of blood. The blood sample is then placed onto the analyte test strip, and the meter analyzes the blood sample. The meter then typically displays a blood glucose level from the analysis.

What is needed is an analyte meter with sophisticated software to help a user manage their diabetes.

BRIEF SUMMARY

Presented herein is a handheld analyte measurement device. The analyte measurement device includes one or more software applications to help the user manager their diabetes. Embodiments and descriptions of the various applications are provided below in conjunction with the handheld analyte measurement device.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the present invention.

FIG. 2 illustrates a glucose control level triage scale.

FIG. 15 provides an example of self-monitoring schedules according to the dimension of concern.

FIG. 16 provides a sample display in accordance with one embodiment presented herein.

DETAILED DESCRIPTION OF THE INVENTION

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be limited only by the appended claims.

Figure 1:
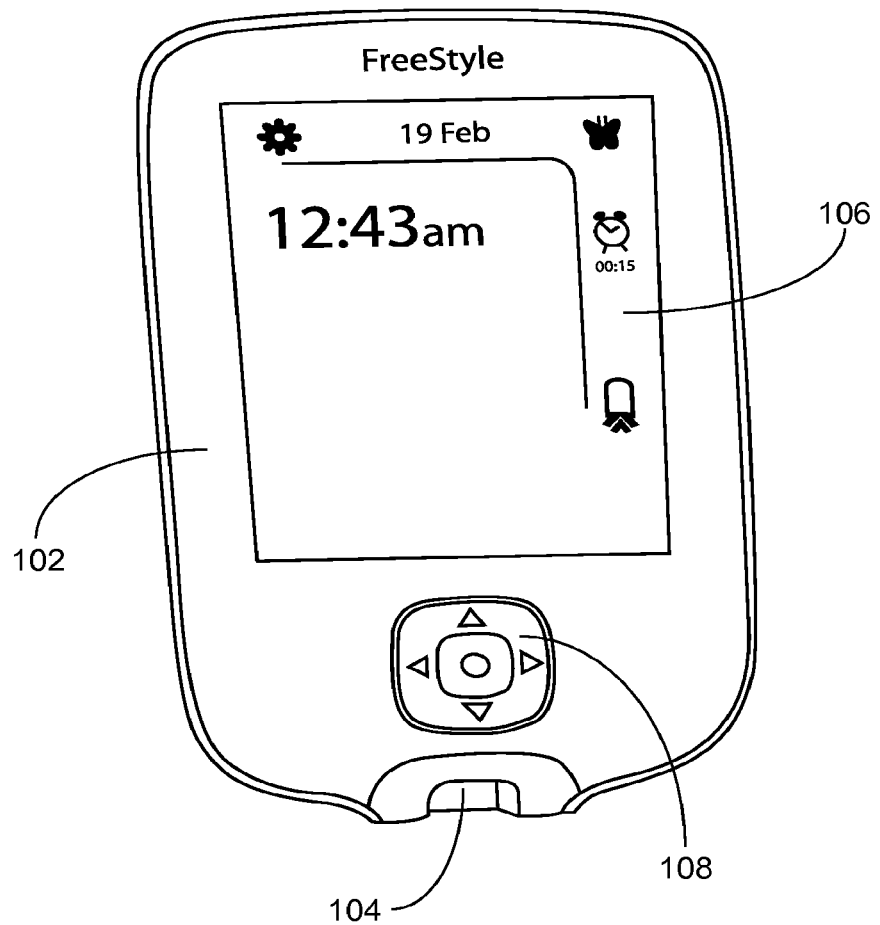
FIG. 1 provides a front-side view of handheld analyte measurement device in accordance with one embodiment presented herein.

FIG. 1 provides a front-side view of handheld analyte measurement device, such as an analyte meter 102, in accordance with one embodiment presented herein. In one embodiment, analyte meter 102 includes a test strip port 104, a display unit 106, and at least one control button 108. In practice, an analyte test strip (or sensor) is inserted into test strip port 104 in order to conduct an analyte test; for example, a blood glucose reading or a blood ketone reading. Meter 102 includes software (as described below) to analyze the sample placed on the test strip, and the results of the analysis are typically displayed to the user via display unit 106. The user may also use control button 108 to provide appropriate instructions to meter 102.

In one embodiment, meter 102 includes one or more diabetes management software applications. The integration of software applications with meter 102 provides an opportunity to augment traditional glucose and/or ketone readings to provide more useful information and feedback to patients and doctors. As such, meter 102, with loaded software applications, can be part of a robust therapy management system. The software applications can be factory pre-loaded, or installed by the user or health care provider after first use by the user. In addition to the software applications discussed below, meter 102 may include one or more of the software applications described in U.S. Pat. No. 7,766,829; and U.S. Provisional Patent Application Nos. 61/015,185; 61/262,849; 61/290,841; 61/254,156; and 61/325,155; the disclosures of which are incorporated herein by reference in their entirety.

In one embodiment, software applications are licensed, acquired, or otherwise built by third-parties to be incorporated into meter 102, or other biometric devices. Examples of the types of software that may be incorporated include: (a) behavioral engagement software; (b) therapy recommendation algorithms; (c) survey applications; (d) standardized reports; etc. A means may be provided to prevent unauthorized software from being executed by the device. A number of methods may be used to prevent such unauthorized execution. For example, the operating system on the device may require a code imbedded in the software before it would allow the software to be executed. The code may be provided by the meter manufacturer to trusted third-party vendors. Furthermore, the code may be generated from information provided regarding the application, to prevent the code from being publicized. In other words, a generation algorithm code may be provided. The information used to generate the code may be, for example, the company name or product name or another code. Also, time-based information may be used, such as the earliest date that the application may be installed. Further, actual loading of the software on the device may be prevented, using the same techniques. For example, the installation driver located on the device may require authorization before it proceeds with installation.

Analyte meter 102 may further include one or more internal or external communication modules. The communication module(s) may be used to receive and/or transmit data and/or program instructions. The communication module(s) may also download software applications from one or more servers. In one embodiment, the communication module is used to communicate with one or more external devices; such as, for example, a medication (drug) deliver device; a cellular phone; a laptop computer; a mobile device, such as a PDA, iPhone, iPad, tablet computer, etc.; a desktop computer; an analyte meter; and/or another analyte measurement system. For example, in one embodiment analyte meter 102 is a handheld component of a CGM or on-demand glucose monitoring system. In one embodiment, the communication module can be configured for wireless communication to an external device. Wireless communication may be provided by, for example, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM)).

Software applications can reside on multiple patient devices at the same time. As such, the same user interface and software interface may be provided to the patient regardless of which personal device the patient is using. Modifications and updates to the software may be pushed or pulled down to all devices. Further, devices can be linked and synced with one another to ensure continuity of data and patient experience.

Software Application for Triaging Glucose Control Assessment and Adapting Self-Monitoring Intervention For people with diabetes who are not taking multiple daily injections of insulin, the utility of self-monitored glucose measurements has not been well established. The current standard of care is to use the long-term biomarker of average glucose control A1C to assess and titrate diabetes therapies, with little or no regard to self-monitored glucose acquired using strips and sensors by patients in everyday settings. However, the failure of this approach is evident in that less than half of patients with diabetes in the U.S. meet control targets, putting them at higher risk for diabetes-related complications. The opportunity exists to create a software application which is capable of identifying underlying glucose control defects made apparent by self-monitored glucose that are not identifiable from long-term biomarkers such A1C.

Furthermore, for patients who do take insulin, identification of clinically-important patterns in their self-monitored glucose is extremely unstructured, and generally inefficient and time-consuming for care providers. The effect is such that the vast majority of care providers of insulin-using patients do not even bother creating computer-generated summary reports of downloaded self-monitored blood glucose (SHBG) values.

Further, A1C, as a long-term biomarker of excess glucose exposure, falls short of being able to monitor and assess important dimensions of glucose control. Such dimensions include overall hypoglycemia and glucose volatility, as well as periods of the day with excess hypoglycemia, glucose volatility, and glucose exposure. Therapeutic interventions to achieve target glucose control must recognize the trade-off between long-term risk of complications and acute risk of low glucose (hypoglycemia). If therapy is added improperly, there is the possibility of causing more harm (hypoglycemia) than good (reduction of long-term complication risk). To mitigate this situation, self-monitored glucose measurements may provide the necessary dimensions of control assessment, such that therapy can be adjusted in a progressively safe manner. Furthermore, since the physiologic defects in type-2 diabetes progress over time, there is a need to maintain monitoring of control even once targets have been met.

In one embodiment, there is provided a software application that uses a clinically-rational scale of glucose control; i.e. a "triage" scale, and associated logic for selecting self-monitoring schedules (when and how often to measure) that are optimized to provide assessment of the main control defect identified on that scale. This logic is envisioned to be therapy-dependent in that the times of day posing control risk are expected to vary according to the type of diabetes therapy (e.g., single oral agent, combination therapy, background insulin only, background insulin with other agents, pre-mixed insulin, basal and bolus insulin, etc.) that is being utilized by the patient.

The first aspect of this application provides a rational priority to addressing out-of-target dimensions of glucose control provided by self-monitored glucose, as shown in FIG. 2, where the priorities are numbered (beginning with zero) in the order that they should be addressed. Within the categories it is proposed that problems identified during the night take priority over those during the day due to the increased risk of acute problems (low glucose) being unrecognized by the patient or others while sleeping. When self-monitored glucose data is analyzed (either on a meter or external to a meter), this scale helps focus clinicians on therapy adjustments which address the triaged levels of control in a safe manner. While the general categories are fixed, the criteria for satisfying each level may vary according to individual patient differences or class of patient (e.g., age, therapy used, duration of disease, diabetes type). In any case, the goal of the software application is to focus on the optimally addressing a single aspect of glucose control while keeping other dimensions of glucose control in proper and safe context.

Figure 3:
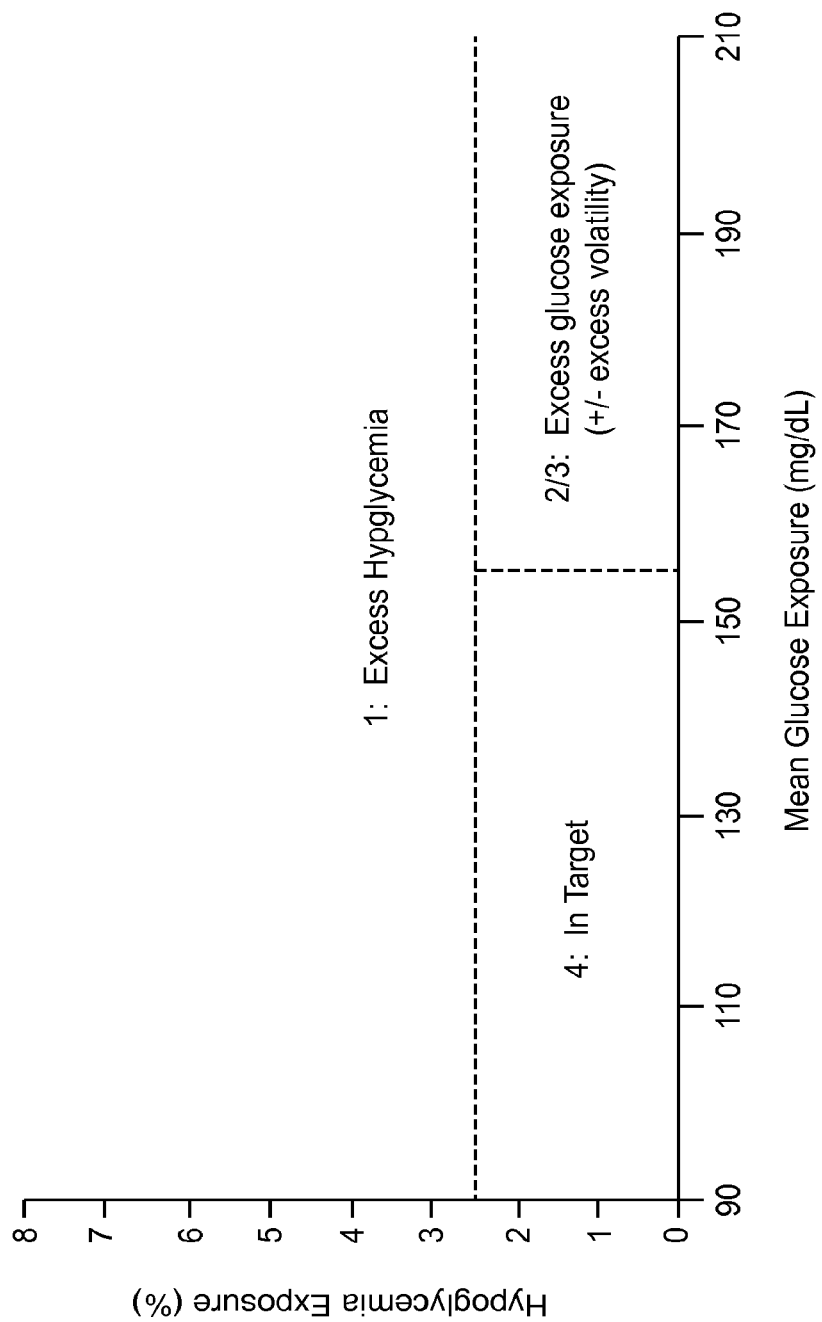
FIG. 3 shows a glucose control grid: Hypoglycemia vs. Mean Glucose Exposure.
Figure 4:
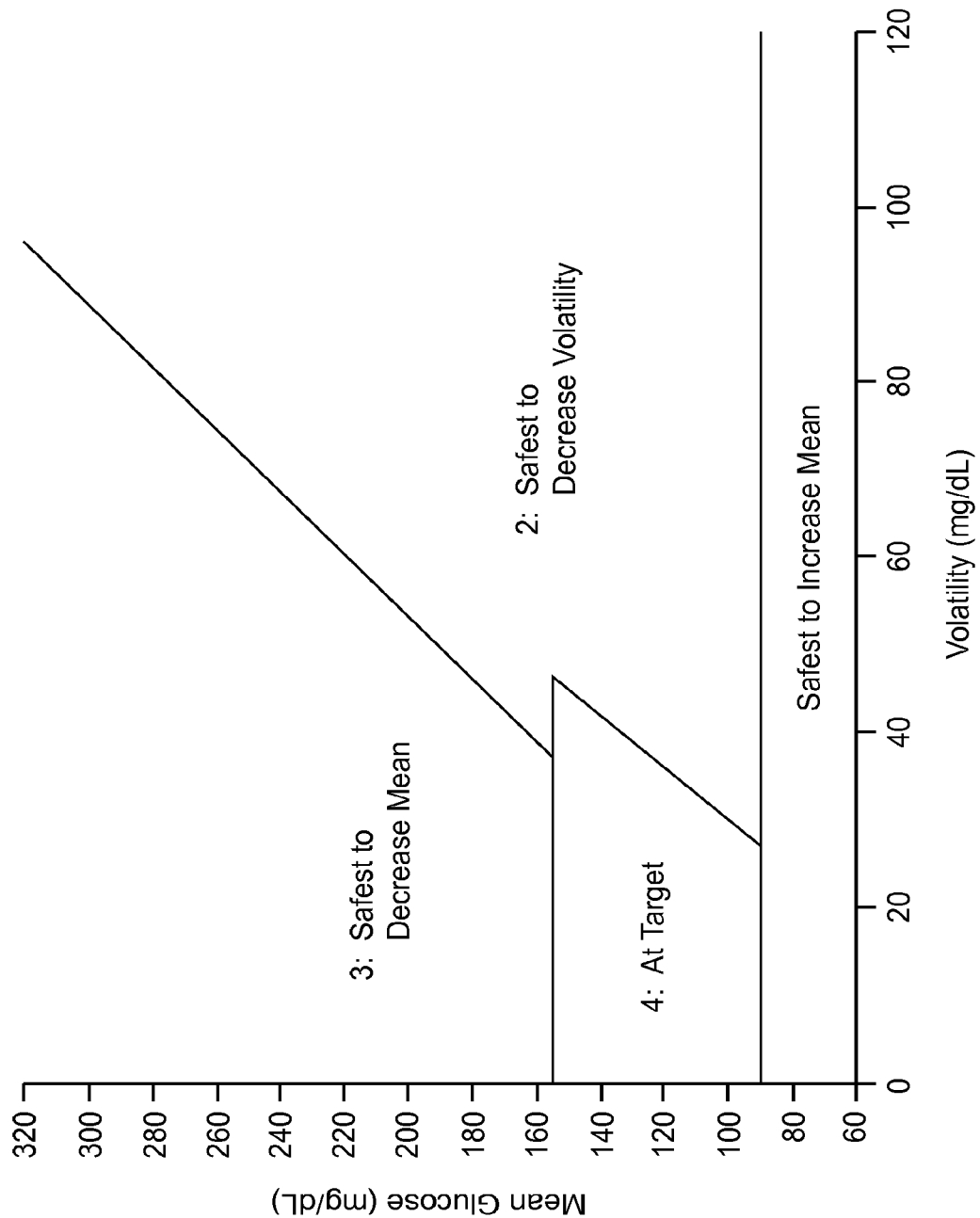
FIG. 4 shows a glucose control grid: Mean Glucose Exposure vs. Volatility.

Progress along this glucose control scale can be represented along the dimensions of interest. For example, FIG. 3 shows how the scale maps to a grid of hypoglycemia versus glucose exposure. This representation emphasizes that hypoglycemia needs to be addressed first, even if it results in an increase in glucose exposure to get control levels 2 or 3. In another example, FIG. 4 shows a grid of glucose exposure versus glucose volatility. This representation is more effective at contrasting control levels 2 and 3.

In another aspect of the present inventions, the software application proposes how to allocate discrete self-monitored glucose measurements according to glucose control level. This aspect is intended to guide how to allocate a relatively small number of glucose measurements per day (e.g., 1-12) over a number of days such that the dimension(s) of glucose control of interest is optimally measured. At minimum, the software application proposes that there are optimal "schedules" of discrete self-monitoring of glucose for each glucose control level (1-4). The schedules are likely to be further refined according to diabetes therapy type being used or other patient characteristics. Furthermore, algorithms may be developed which automatically shift between schedules as each dimension of control is assessed and surpasses thresholds. In some cases, prior knowledge of the initial condition of the patient, such as non-insulin-using type-2, may be used to modify the testing schedule to reduce testing for hypoglycemia.

Figure 5:
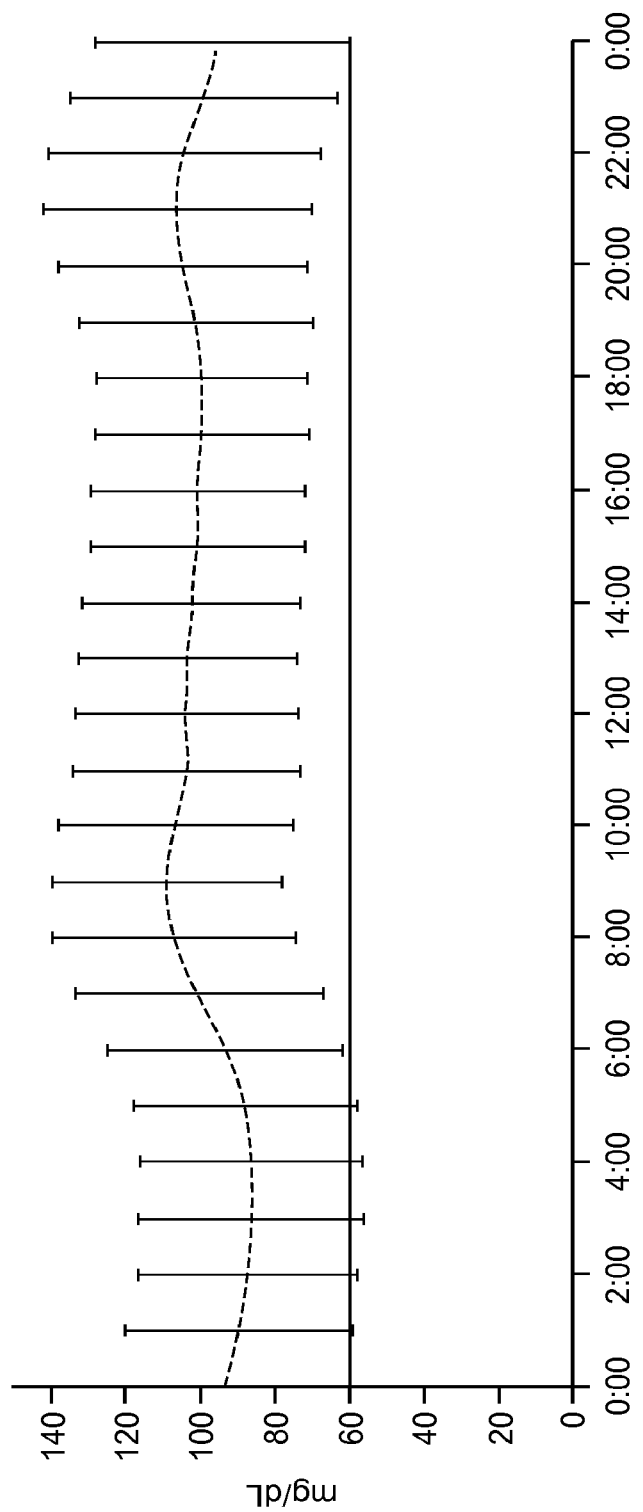
FIG. 5 provides a mean and standard deviation graph of hourly 10th percentile of glucose values for 80 patients on multiple daily injections of insulin.
Figure 6:
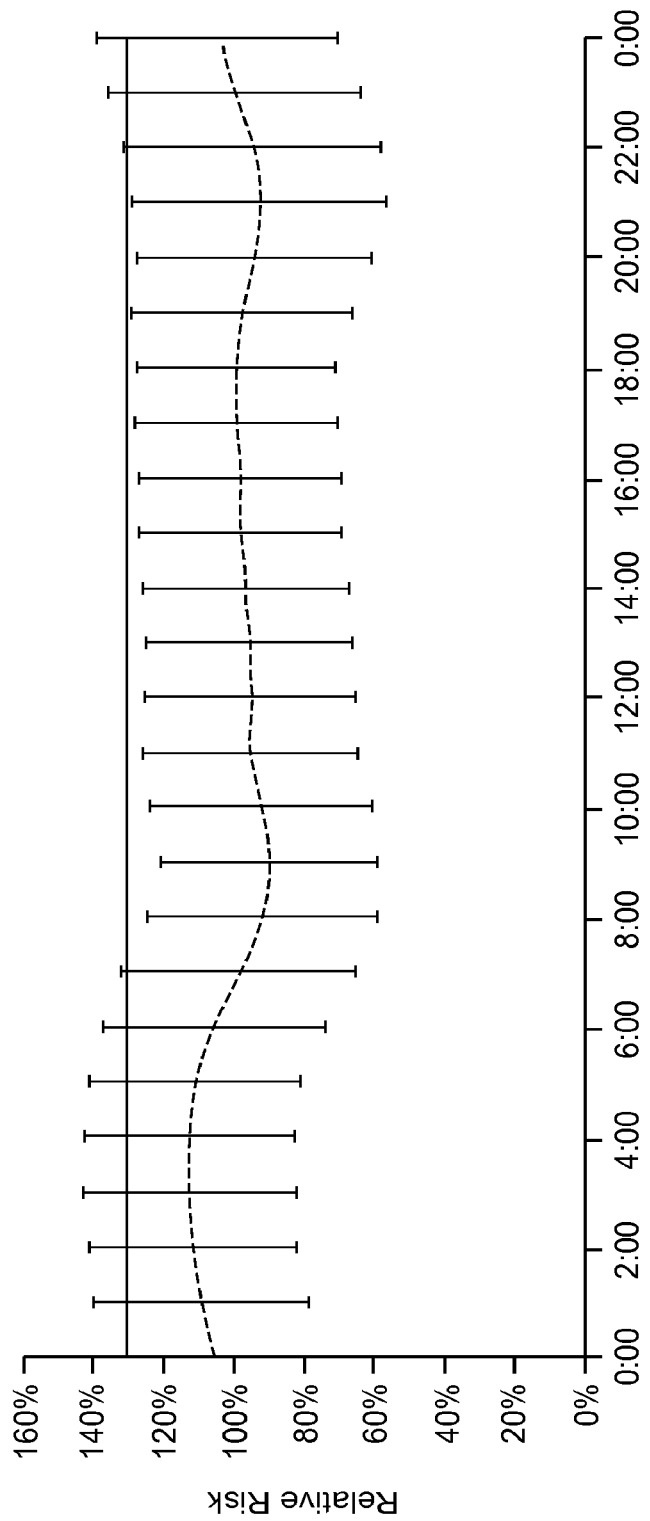
FIG. 6 provides hourly hypoglycemia risk: hourly mean and standard deviation of 10th percentile adjusted for 24-hour mean (80 patients on multiple daily injections of insulin), 100% set to mean hourly hypoglycemic risk.
Figure 7:
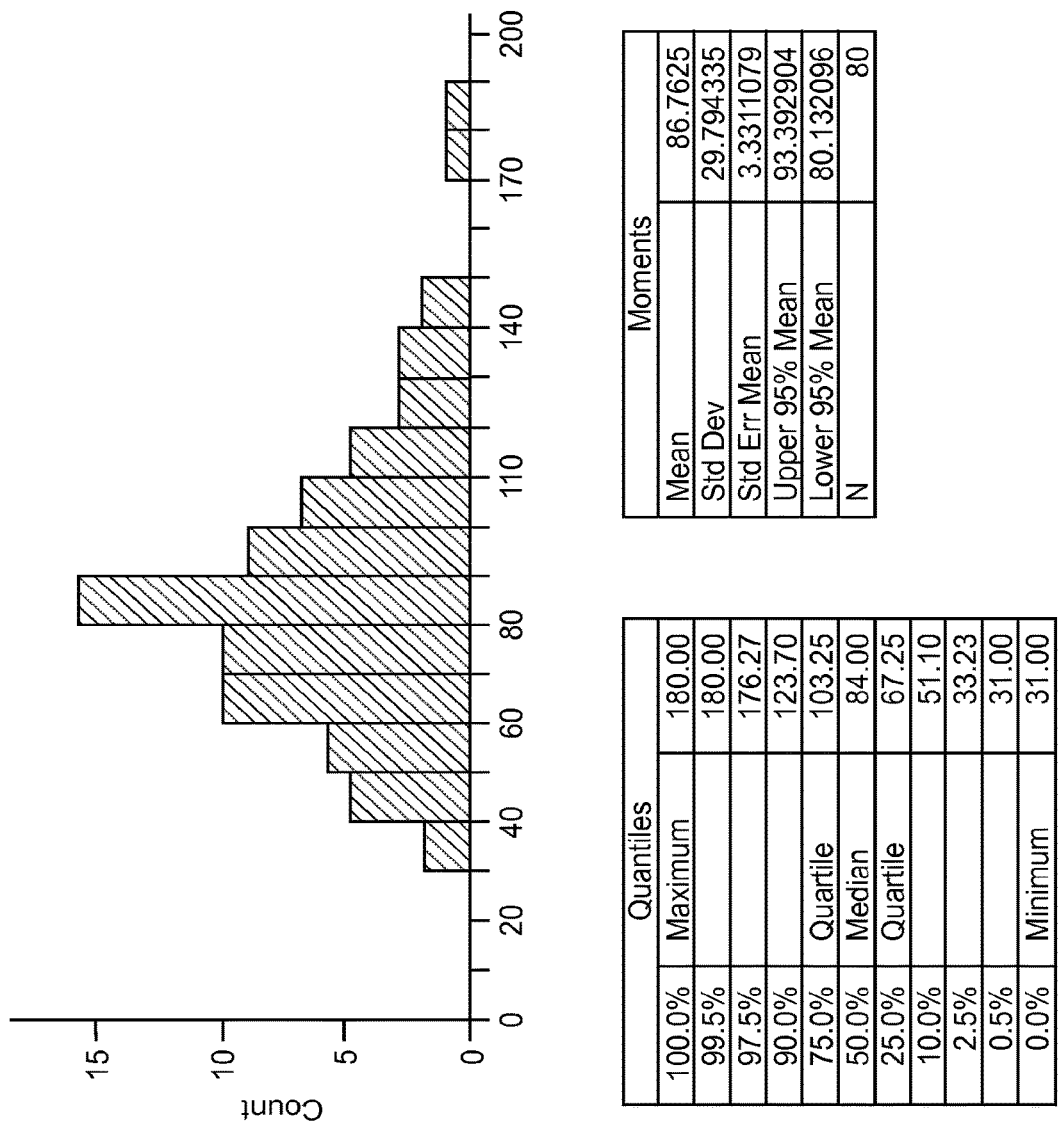
FIG. 7 provides 10th percentile of glucose values at 4 AM for 80 patients on multiple daily injections of insulin.
Figure 8:
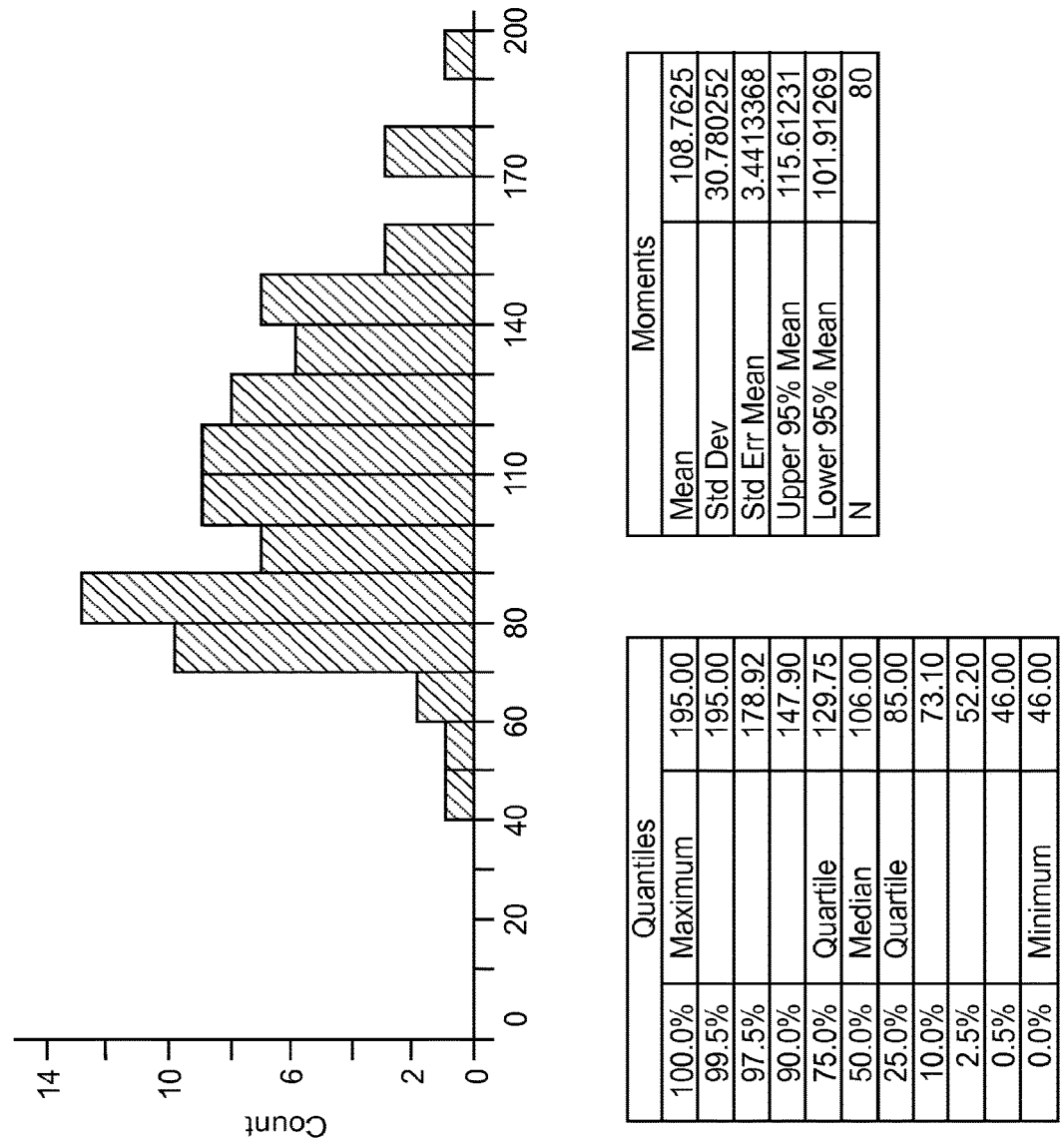
FIG. 8 provides 10th percentile of glucose values at 9 AM for 80 patients on multiple daily injections of insulin.

To demonstrate this aspect of the invention, it is applied to a group of patients on multiple daily injections of insulin (MDI). Each patient had continuous glucose monitoring every 10 minutes for 14 days. Within each hour of the day, the 10th percentile value was found. Typically this means there were 6 measurements per hour over 14 days for a total of 84 values within each hour. These values are sorted, highest to lowest, and one method to define the 10th percentile value is to do a linear interpolation between the 8th and 9th lowest values (since the $^{84}/_{100}$="8.4$^{th}$" value doesn't exist). In this way, a glucose value is found for each hour where 90% of the glucose measurement in this hour of the day are higher than that value, and 10% are lower. Combining all the patients, the mean and standard deviation of their hourly 10th percentile glucose values are shown in FIG. 5. These values are transformed into hourly hypoglycemia risk by scaling to the 24-hour mean of the 10th percentile values by: [1-(24-hr mean-x-hr)/24-hr mean] *100, where x is each hour of the day, shown in FIG. 6. This shows that for this class of patients the highest hypoglycemia risk is between 11 PM and 7 AM, shown by having the error bars exceed the selective threshold of 130%. Two hours of the day are compared in FIG. 7 and FIG. 8. At 4 AM, 25% of the patients have 10% of their glucose values below 67.25 mg/dL, representing more hypoglycemia during that hour of the day then at 9 AM (less than 10% of the patients have 10% of their glucose values below 67.25 mg/dL). This indicates that self-monitoring schedule to assess hypoglycemia risk should be more comprehensive during the night then during the day.

Figure 9:
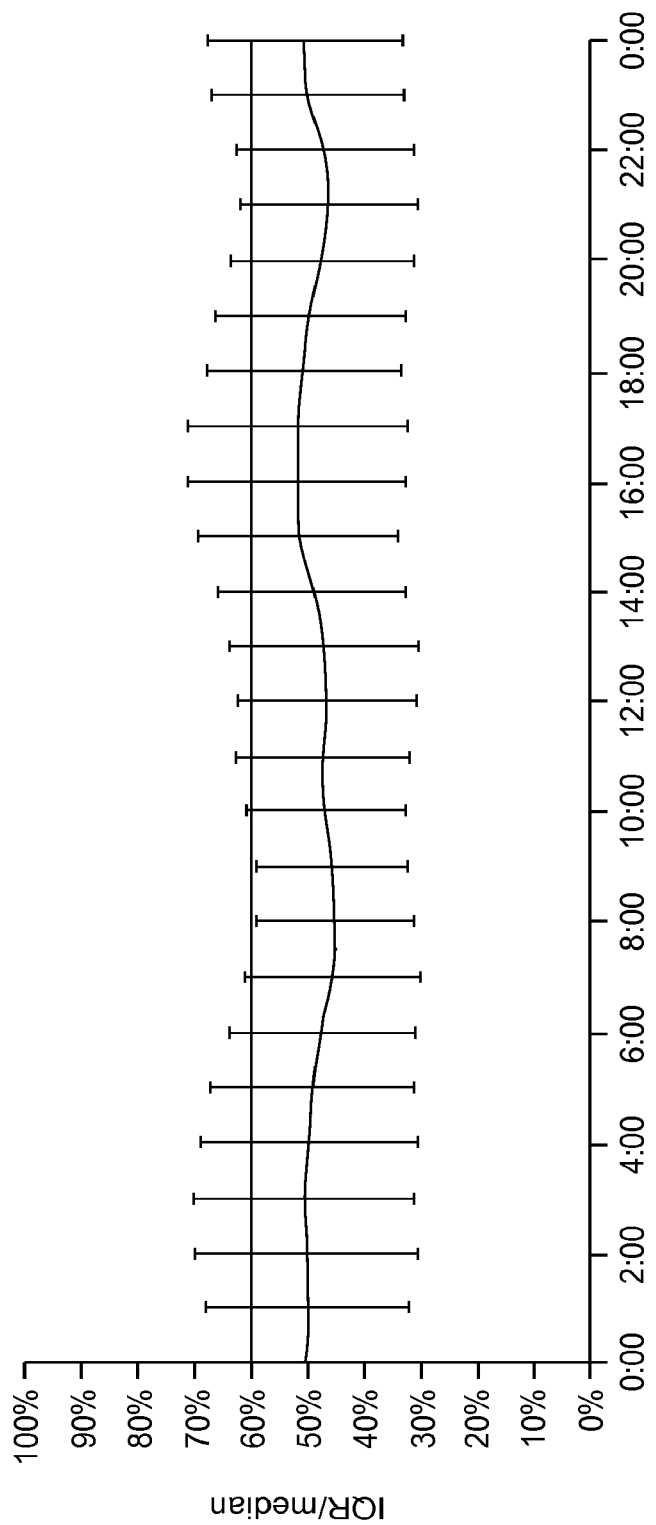
FIG. 9 provides hourly volatility risk: mean and standard deviation of hourly (interquartile range/median) of glucose values for 80 patients on multiple daily injections of insulin.
Figure 10:
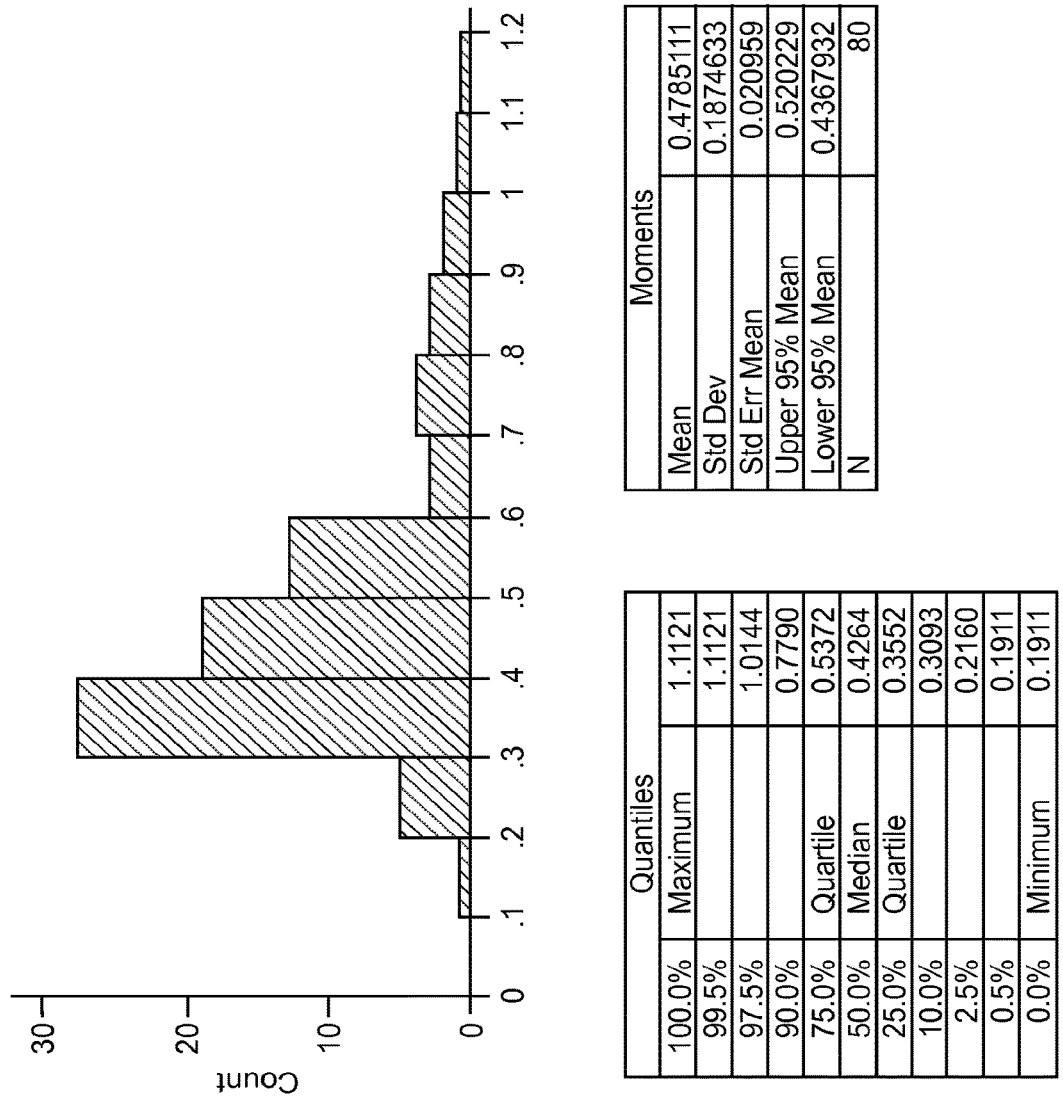
FIG. 10 provides relatively interquartile range (IQR/median) of glucose values at 9 AM for 80 patients on multiple daily injections of insulin.
Figure 11:
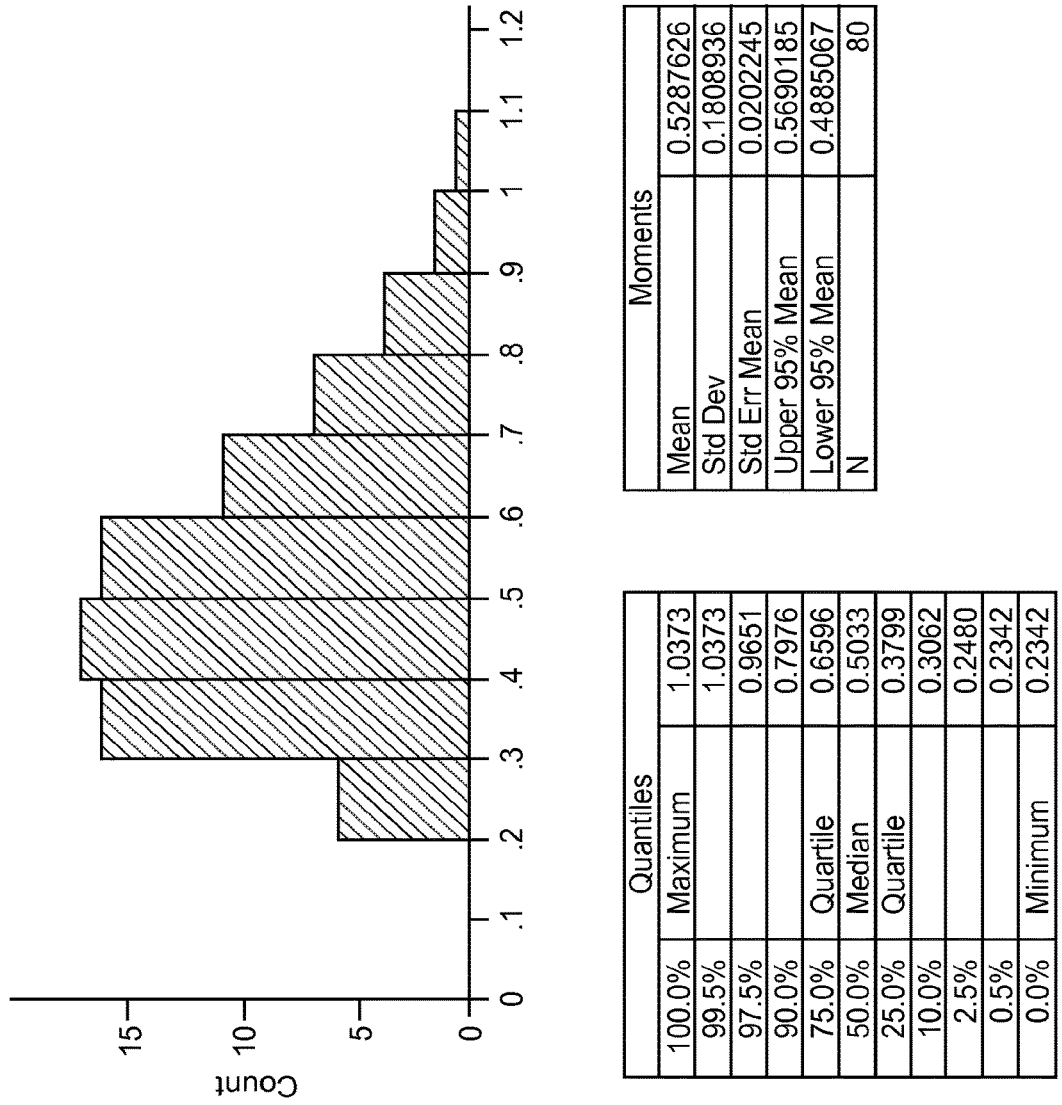
FIG. 11 provides relative interquartile range (IQR/median) of glucose values at 4 PM for 80 patients on multiple daily injections of insulin.

It is important to manage glucose volatility, since excess volatility may result in increased hypoglycemia when therapies are adjusted to reduce overall glycemia. FIG. 9 shows the volatility per hour of this group of MDI patients, indicating that a self-monitoring schedule to assess volatility should be more comprehensive during the hours of 10 PM-7 AM and 2 PM-8 PM. FIG. 10 and FIG. 11 compare the volatility of two different hours of the day, one with the main time of concern (4 PM) and one outside the time period of concern (9 AM).

Figure 12:
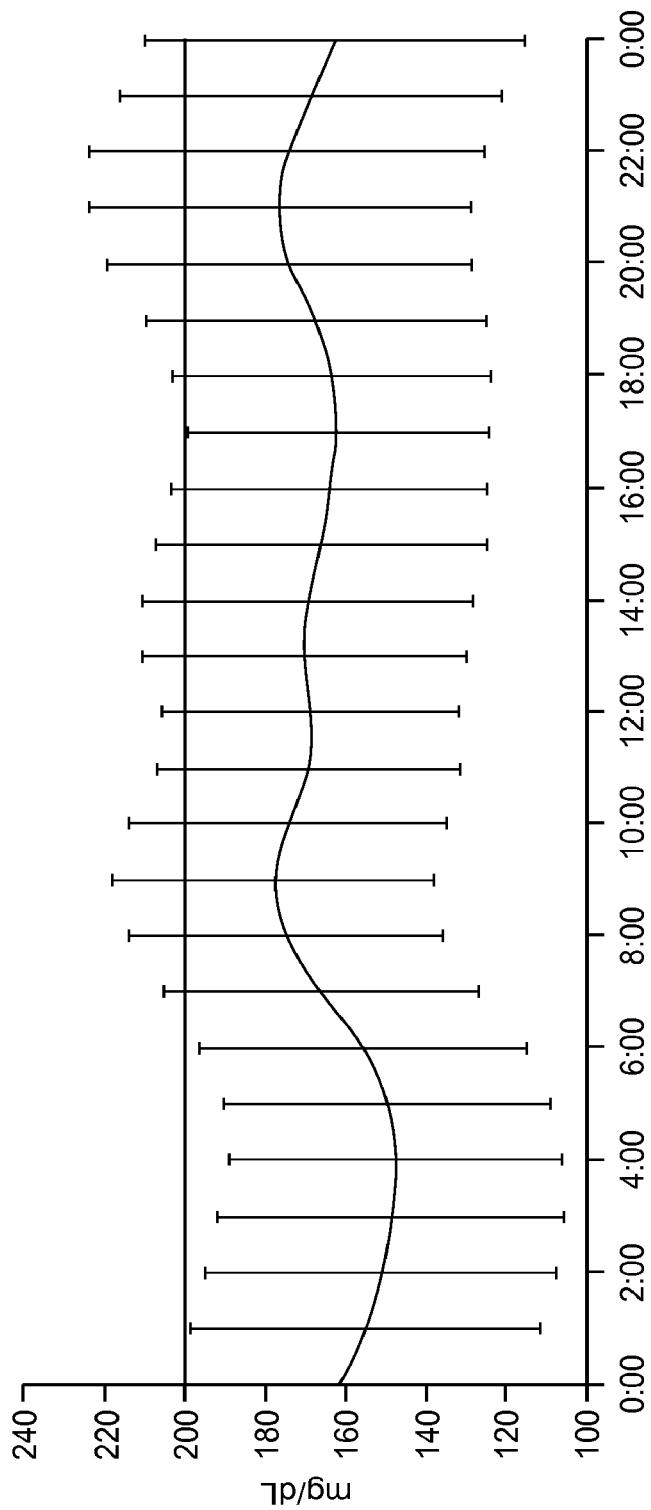
FIG. 12 provides hourly excess glucose risk exposure: mean and standard deviation of hourly median of glucose values for 80 patients on multiple daily injections of insulin.
Figure 13:
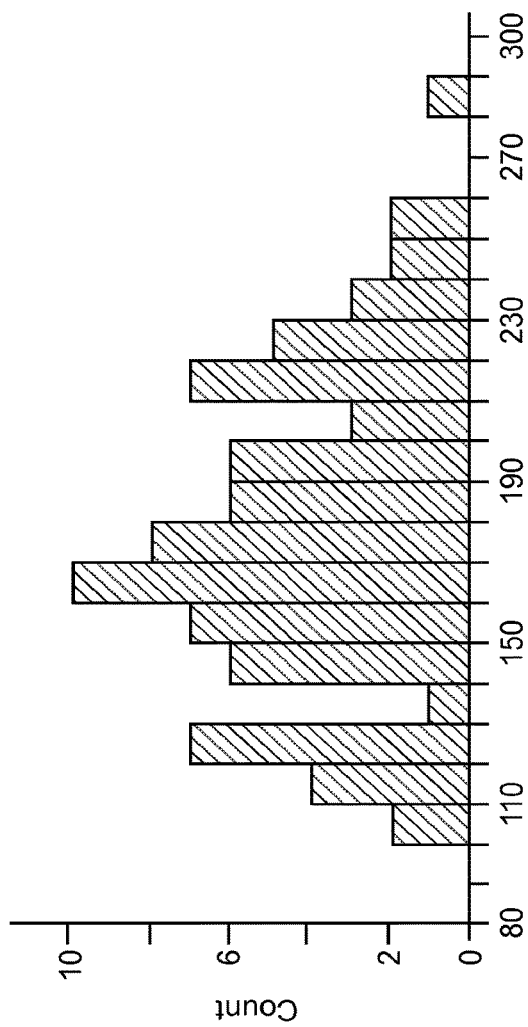
FIG. 13 provides median of glucose values at 9 AM for 80 patients on multiple daily injections of insulin.
Figure 14:
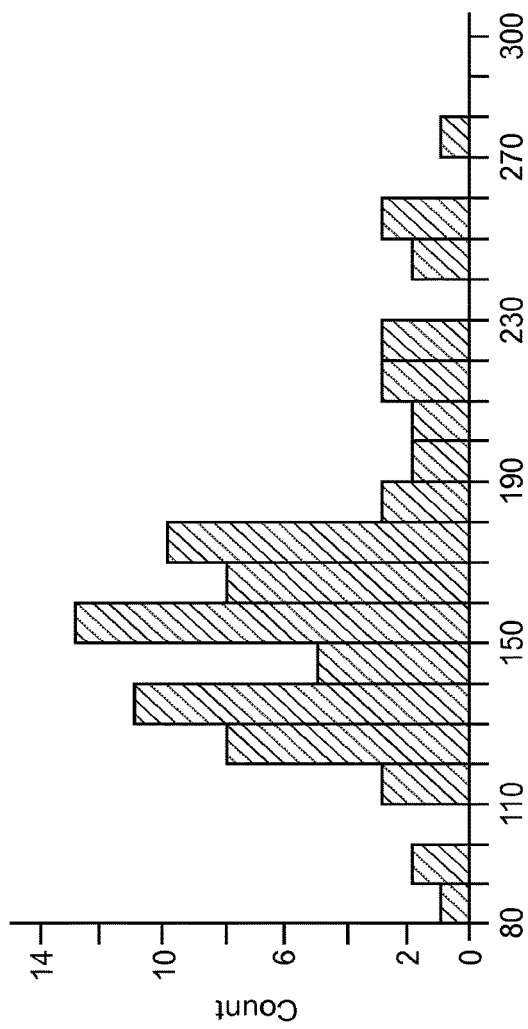
FIG. 14 provides median of glucose values at 4 PM for 80 patients of multiple daily injections of insulin.

In order to assess excess glucose exposure, FIG. 12 shows the exposure per hour for this group of MDI patients, indicating that a self-monitoring schedule to assess excess glucose exposure should be more comprehensive during the hours of 7 AM-3 PM and 7 PM-12 AM. FIG. 13 and FIG. 14 compare the excess glucose exposure of two different hours of the day, one with the main time of concern (9 AM) and one outside the time period of concern (4 PM).

In summary, an example of self-monitoring schedules according to the dimension of concern is shown in FIG. 15.

Software Application for Prompting Patient to Test Per Optimal Schedule

Glucose meters and monitors commonly allow patients to configure them to provide reminders to test their blood glucose. Another aspect of this disclosure is to provide a means to configure a meter to schedule a number of test reminders, to occur over one or more periods of time. This test reminder schedule may be optimized to ensure glucose data are collected for different possible analysis purposes. For instance, the test reminder schedule for one test period may be optimized for diagnosing the patient's glucose control and providing insight into appropriate treatment modifications. The test reminder schedule for another test period may be optimized to determine if a patient's medication is effective—in this case, more than one test period may be used; one corresponding to one medication dose and another corresponding to another medication dose, with the results from the two periods compared to determine if the medication dose or dose change is effective. For instance, if a medication is intended to reduce post-meal glucose, then the difference of the median of the post-meal glucose values may be compared to a predetermined threshold to determine if the medication is effective. Many other mathematical comparisons may be contemplated. The test reminder schedule for another test period may be designed to provide a margin of safety for the patient while requiring a lower frequency of testing than the other two periods. The meter may be configured to perform test prompts according to different schedules over multiple periods.

Test schedules may be defined a number of ways. One convenient schedule is to define specific date and time instances when the test prompt should be displayed. The actual date and time may be derived from a desire to gather sufficient data within specific time-of-day periods across multiple days, for example 14 days, and to require a certain number of total tests per day, such as 7 tests. The schedule may consist of reminders scattered across the days so that they appear random, or the times may shift from day to day. In one embodiment, the schedule provides instances when consecutive tests are performed. For instance, post-meal reminders would be serially paired with pre-meal reminders. Another example is fasting reminders serially paired with bedtime reminders. Test schedules may require serial pairs, serial triplets or even more data points that are serially adjacent. Providing this type of test data allows analyses of data that may be used to indicate serial patterns in data that could be indicative of diabetes management issues that should be addressed. For instance, a bedtime high glucose reading followed by a fasting (morning) low glucose reading may indicate problems with correction doses of insulin at night.

In another embodiment, rather than defined by time-of-day, test schedules may be defined relative to events such as meals, or a combination of time-of-day and relative to meal events. For instance, a test schedule may produce a reminder at 10 am to test the following day for pre-breakfast, if a glucose reading was not taken between 6 am and 10 am and tagged as pre-breakfast. If a pre-breakfast reading did occur, a post-breakfast reminder would be generated some time later, for example 2 hours and 15 minutes later.

Test schedules may be defined for a specific period but the algorithm in the meter may have a feature to "catch up" to acquire readings that were missed. For instance, if a reading was missed for the period of 10 am (when the reminder occurred) to 12 am (when the next reminder is presented), the software may request another 10 am reading the next day even though this was not part of the original schedule. Another example is that a reminder may be provided for the missed 10 am reading after original test period was completed. Many variations of this concept can be contemplated.

The test schedule may also be derived from configurable time periods. For instance, in one embodiment, four time periods—overnight/fasting, post-breakfast, post-lunch and post-dinner—may be defined by three instances—breakfast, lunch and dinner. The system used to generate the test schedule may provide as an input to the test schedule generation algorithm, means for the user to adjust these three instances, so that the test reminder prompts can be tailored to the patient's lifestyle.

The test reminder schedules and test periods may be configured into the meters by a user interface on the meter or, in one embodiment, by a computer-based software program. The configuration interface may provide a "pick-list" of possible schedules: for instance, the interface may provide a choice of no schedule, a 4-per-day time-of-day schedule, a 7-per-day time-of-day schedule and a 7-per-day relative meal schedule. Test periods may also be configured, by start time and by duration. As mentioned, multiple periods of different types of testing may be defined and configured into the meter. The selected test schedule may be presented graphically to the user, and a means for the user to modify the schedule can be contemplated—for instance, adding or moving tests to tailor the schedule. Also, this means of configuring test reminders may include other reminders, such as the patient's next doctor visit, or when to take medications. The software mechanism for providing multiple reminders according to a schedule can be accomplished using a table that includes, e.g., date and time of reminders—many different software designs may be implemented to accomplish this goal. In one embodiment, where the configuration interface is provided by a software program, once the user selects the desired schedule, it may be loaded into the connected meter.

Retrospective Association of Events Types with Detected Glucose Events

Clinicians commonly review patient glucose data to detect adverse events such as glucose highs and lows, or other glucose patterns, such as high rates-of-change or other episodic patterns that can indicate problems with glucose management. In order to mitigate the cause of these adverse glucose events, the clinician will benefit from knowing what patient activity, e.g., life-style event, was associated with the adverse event. For instance, highs may be due to the patient missing their medication, or lows may be due to exercise or alcohol consumption. Clinicians typically review patient glucose data during patient's office visit and may ask the patient if they remember the circumstances just preceding the adverse event. However, patients usually cannot remember with an adequate level of detail events that occurred many days or weeks previous.

In one aspect, the present disclosure provides a means to help patients and clinicians identify and associate adverse glucose events with life-style events. Such means may be located on a meter or monitor, and such embodiments are applicable, for example, to discrete SMBG devices, "on-demand" continuous glucose meters, and "real-time" continuous glucose monitors (which may contain real-time glucose alarms). Specifically, when an adverse glucose event is detected by the device or observed by the patient, the notification on the device provides a pick-list of possible life-style events for the patient to select from. For instance, using an SMBG device, if a patient conducts a measurement and it is low, then the device user interface (UI) provides a list of event choices, either on the same screen as the reading or on a screen that can be reached with a button press (either a "hard" or "soft" button or any form of user activation link) to initiate a screen that provides event choices. The selection list may be provided as a radio button (meaning only one choice can be made) or a check box list (meaning that one or more choices can be selected). Upon selection, or upon accepting the selection such as with an OK button, the reading is associated with the one or more events selected and this information is stored in the device log. A means to retrieve past glucose values may also be provided similarly.

The list of life-style events displayed to choose from may also be specific to the type of adverse event. For instance, occurrences of lows may be associated with insulin corrections, alcohol consumption, exercise, missed meals, etc; while occurrences of highs may be associated with missed insulin boluses, over-eating, inadequate insulin boluses, etc. In addition to a pick list, an entry field may be provided for the patient to type in a custom event.

The event pick list could also be provided in the context of a CGM system, wherein a CGM device would detect the adverse glucose event, such as a low glucose occurrence, in real-time and notify the patient with an audible, vibratory or visual indication. Along with such an indication, an event pick list may be provided which the patient may use to associate a life-style event with the adverse glucose event, as described above. A glucose low event, for instance, could be defined as a glucose value detected below a predefined threshold following a glucose value detected above a predefined threshold.

The event pick list could also be provided for an on-demand CG system. The device would detect adverse glucose events that have occurred in the past based on stored data. When the user accessed the data, the display would provide a notification of any one or more adverse events (such as glucose lows) and access the event pick-list for each as described above. A glucose low event, for instance, could be defined as a glucose value detected below a predefined threshold following a glucose value detected above a predefined threshold. Many other event detection schemes have been employed in CGM alarm systems and data analysis systems which may be applicable here.

A CGM or on-demand CG device may also provide a periodic notification, e.g., once per day, to the patient that provides past detected adverse events and a means to associate these with one or more life-style events. The notification period or time could be configured by the user in a setup function. In addition, a means to generate and access this notification via a menu on demand can be provided.

Multiple adverse event detections and means to associate each with life-style events could be provided a number of ways using standard user interface techniques understood by those skilled in the art. For instance, a list of adverse event names and corresponding event times could be displayed, each with a link to the event pick-list pop up screen to allow the user to associate one or more events. In one embodiment, when all events are selected for a particular event, the user accepts the selection and the display returns to the list to allow the user to initiate the event pick-list for another adverse event. The user accepts the event associations and the adverse events, life-style events and associations are stored in the device memory.

The device may have another screen that can retrieve the stored adverse events and display this information as a list of adverse events and associated life-style events. Again, this information may be displayed on the device a number of ways using standard user interface techniques understood by those skilled in the art. In one embodiment, this information may be retrieved by a computer software program for display, for instance, to a clinician. Furthermore, the adverse events may be mapped to outputs by the software, as described elsewhere in this disclosure. For instance, adverse events may be mapped to recommended treatment options. The associated events may be used to modify the outputs indicated by the adverse events. For instance, they may specify a subset of recommended treatment options, for display to the clinician. As an example, a low glucose adverse event may indicate the necessity to address one of the following possibilities: errors with insulin corrections, alcohol consumption, exercise, and missed meals. If the event associated with the adverse event was alcohol consumption, the software would, e.g., only provide information regarding self-care management consideration regarding alcohol consumption.

In addition to the potential benefits of this aspect of the disclosure regarding clinical review and intervention to help a patient mitigate adverse events, this disclosure also provides a method of providing direct feedback to a patient without clinician intervention—e.g., as the patient associates life-style events with adverse events, they will have an opportunity to learn the impact of behaviors on their glucose and learn how to better manage these behaviors.

Software Application for Tagging Compliance Features for Glucose Monitor

Clinical analysis of diabetes data can be used by health care providers (HCP's) to determine appropriate treatment adjustments to optimize glucose management for patients. Glucose data is the primary source for this analysis. For patients who monitor their glucose with discrete blood glucose tests, it is necessary to conduct a specific test regimen for a period of time, such as three day to two weeks, to provide sufficient data for the HCP to adequately assess glucose management success and determine appropriate adjustments to therapy to improve glucose management. A widely accepted regimen is for seven blood glucose tests per day; one fasting test (waking), one test just prior to each meal and one test two hours after each meal. Methods for helping patients maintain compliance to this testing regimen are needed.

Diabetes data, in addition to glucose values, can be used to help HCP's assess and adjust treatment. For discrete blood glucose testing, it is informative to record whether a blood glucose test is associated with pre-meal, post-meal, or fasting—this is often referred to as tagging. For patients who wear continuous glucose sensors, it is useful to record meals and fasting to resolve periods of glucose data appropriately. For patients who treat their disease with insulin, it is informative to record prandial insulin injection and insulin amount, and meal amounts. However, it is a challenge for some patients to maintain compliance with tagging and event logging. Presented below is a software application that provides help to encourage compliance with recording necessary data for clinical assessment.

For example, in one embodiment, there is provided a software application with tagging and logging modes. Various tagging and logging modes are available. Tagging modes may be enabled/disabled via the meter display, or a PC application designed to configure the meter.

In one embodiment, the software application provides a means for continuous glucose display tagging. For sensor based glucose meters, such a CGM and on-demand meters, another useful mode would be to allow tagging associated with glucose result display. The glucose result display sequence would be similar to blood glucose test tagging, however, the tag would be recorded as a time-stamped event in the meter log. Post analysis of the glucose data would allow segmentation into fasting, pre-meal, and post-meal periods.

In another embodiment, the software application provides a means for prandial bolus and meal logging reminder modes. For patients who treat with insulin (or when it is important to understand meal effects on glucose for non-insulin using patients), recording not only the time of meals and prandial boluses is important, but also amounts. For some patients, it may be difficult to remember to record this information, so a mode is proposed where predefined time periods (such as morning, mid-day, and evening) have associated reminders to prompt the patient to enter this information. At a predetermined time within this period, if the event associated with this period has not yet been recorded, then the meter will provide a reminder for the patient to enter this data.

In another embodiment, the software application provides a "tag when out of range" mode. For instance, the software requests tagging when the blood glucose test or continuous glucose display indicates a glucose result that is out of the target range. Such request would serve two purposes: 1) provide the HCP with additional data to further investigate problems, and 2) provide a reward system to the patient in that they won't need to tag if they stay within range. The software may also allow recording of events associated with past low or high glucose, or high variability events, associated with the sensor based continuous glucose data.

In yet another embodiment, there is provided a test/tagging status display as a home screen or before or after a blood glucose test or glucose display. The display would illustrate the regimen and indicate how much of the regimen had been completed. An example display is provided in FIG. 16, where three tests each are required for seven times during the day. Additional rows can be contemplated to encourage patients to perform other test regimens that are useful for diabetes assessment, such as missed-meal testing. The status display may be associated and enabled with an appropriate tagging or logging mode. When the status display indicates that the regimen has been satisfied, the tagging or logging mode may be configured to disable automatically.

In another embodiment, there is provided a diabetes assessment scheduling program. A patient may not need to continuously tag and record events, as HCP's really only need to assess data over a fraction of time since the last clinical visit. Tagging and logging modes described above would only need to be enabled as needed. However, a convenient means to ensure that these goals are enabled at the appropriate time, e.g., prior to the next office visit, may be provided. For example, the software application may provide a doctor visit reminder. The meter, or a PC application that can configure the meter, is designed to allow the patient or HCP to set a reminder for the patient indicating the next HCP appointment. The reminder may be configured to occur one or more times prior to the appointment. This feature may be enabled at the current clinical visit, or when the next visit is scheduled. In another embodiment, there is provided a tagging reminder (or mode auto enable). As part of the doctor appointment reminder, one of the various tagging modes can be programmed (or scheduled) to be enabled at a predetermined time prior to the appointment. Again, this feature may be enabled and set up from the meter or a PC application that can configure the meter.

Software Application for Providing Upload Prompts to a Patient

In one embodiment, there is provide a software application for providing upload prompts to a patient.

Patients do not currently self-test their blood glucose levels or other biometric data (blood pressure, weight) with the frequency suggested by their physician. This leads to physicians not having adequate information to make appropriate testing and therapy changes that would keep the patient within specified blood glucose targets. As such, there is provided a software application that would prompt the patient to upload their blood glucose or other biometric data at specific times to allow physicians to have the information needed to make appropriate changes to therapy and thereby better manage their disease.

Figure 17C:
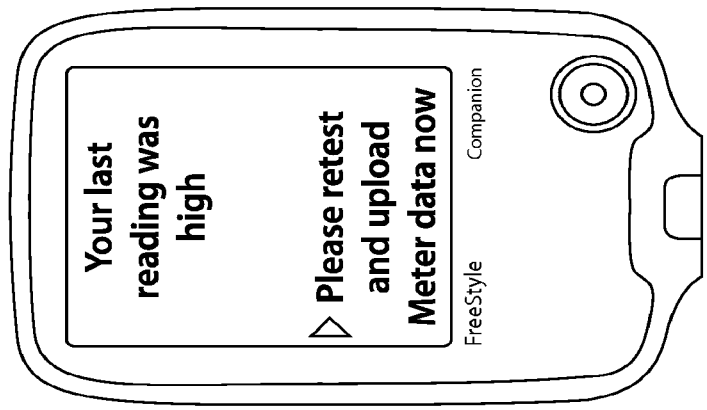
FIGS. 17A-17C provide example prompts on an analyte meter.
Figure 17B:
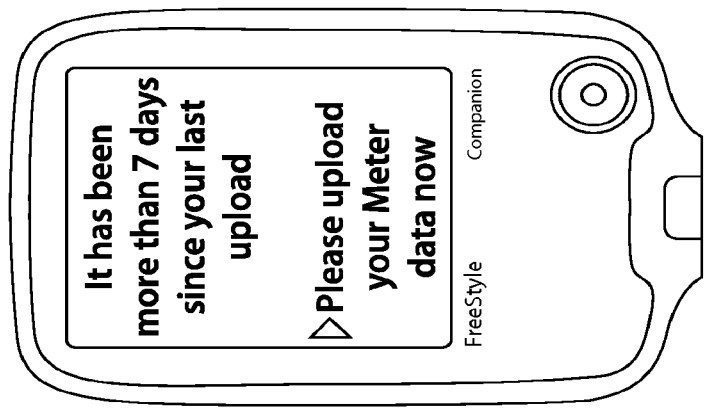
Figure 17A:
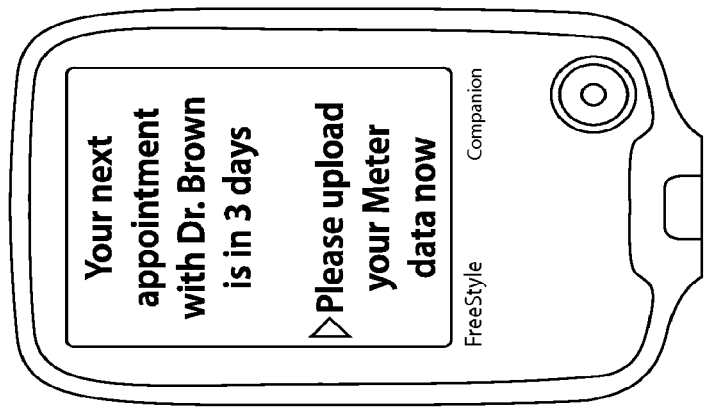

FIGS. 17A-17C provide three examples of where a patient is prompted to upload data. For example, FIG. 17A shows a prompt prior to a physician visit. When a patient connects their handheld device either to their computer through a USB cable, or via a Bluetooth or cellular connection to the cloud/server, a patient reminder is put on their device based on an upcoming scheduled doctor visit. A reminder would be highlighted on the device for the patient to upload their data (blood glucose or other biometric data) several days prior to the doctor visit.

FIG. 17B shows a prompt for when the patient has not sent blood glucose or other biometric data to the cloud/server in a specified amount of time. For example, if it has been more than seven days since the patient has uploaded their blood glucose data or other biometric data, the handheld device would send them a reminder. This would be an algorithm that would be based in the cloud/server that would automatically send the reminder to the handheld device.

FIG. 17C shows a prompt for when a blood glucose value is reported that is outside of a specified target range. The prompt may indicate a higher potential for a hypoglycemia or hyperglycemia event. Alternatively, other biometric data that is entered into the cloud/server may indicate a health issue related to a co-morbid condition. Use of the application in this manner would be dependent on the data input into the cloud/server, which would then be analyzed by algorithms to determine if the input value is outside of the range. If the input value is out of the range, a prompt would ask the patient to test again. If this value is still outside of the range, the server/cloud may prompt a stakeholder to contact the patient via text or phone call to provide assistance or therapy changes as necessary. Prompts may also be provided to make a therapy recommendation change based on the reported blood glucose value or other biometric data.

In another embodiment the software application may provide prompt uploads based on rules-based risk designation. For example, based on the blood glucose data or other biometric data that has been analyzed by the server/cloud, the patient may be designated through algorithms to be in a high-risk category. Based on this analysis, the physician can be alerted to the deteriorating condition of the patient and a new testing regimen can be suggested with new patient upload prompts. Changes in testing regimen may be automated by the algorithms in the server/cloud.

In another embodiment the software application may provide prompts for performing structured test for specific timeframes prior to HCP visits in order to assess glucose control. Prompts would provide reasons, timeframes, and/or specific times to test as well as prompts for upload. If a reading is out of a specified range, the system can then prompt the user and also alert a health care provider of an out-of-range reading.

Software Application for Transmitting/Receiving Information about Multiple Biometrics In one embodiment, there is provide a software application for transmitting/receiving information about multiple biometrics. For example, a meter may be configured to captures three key pieces of information: 1) blood glucose; 2) ketone levels; 3) carbohydrates consumed; and 4) suggested insulin dosing. Alternatively, the meter may be modified to receive/transmit other biometric information such as: blood pressure; body weight; cholesterol; etc. As such, there is provided a software application that can process, transmit, receive and display different biometric data.

Software Application for Enabling Third-Parties to Conduct a Survey

In one embodiment, there is provide a software application for enabling a third-party to conduct a survey.

One of the challenges faced by certain third-parties (e.g., payors, disease management companies, etc.) is the inability to identify certain patient segments and understand their behavior. Typically third-parties use call centers that employ several people to call patients on their phones. If the patient picks up the phone and is willing to talk to the representative from the call center, the representative then asks the patient the desired questions. The responses from the patients are then analyzed to make the relevant determinations. Provided herein is a software application for conducting such surveys on the patient's handheld device. As such, surveys are performed on the actual meter. The third-party may then receive patient-specific information from the meter (e.g., glucose reading, or other biometric) and can then segment the patient based on various criteria. Upon segmentation, the third-party sends surveys to patients through their respective devices. Patients may then enter necessary information and transmit the surveys back to the third-party for analysis.

The software application may be employed on any device that transmits biometric information about patients. Such devices should be capable of receiving and sending text information.

The primary purpose of these surveys will be to help third-parties identify patients who are at risk, and help them better manage the disease. Such surveys fall into several categories including: medical (e.g., Are you taking any drugs to treat hypertension?); compliance (e.g., Did you get a micro-albumin test done in 2011?); behavioral (e.g., Do you exercise 3+ times a week?); etc. In addition, the survey can be used by manufacturers to target patients for commercial activities. Commercial questionnaires may require the patient to give: their approvals; purchase patterns (e.g., Do you purchase glucose tablets for treating hypoglycemia?); channel questions (e.g., Do you purchase products on-line or at your local pharmacy?); promotions (e.g., The attached coupon will give you a 10% discount on your next purchase); etc.

The method of use for these surveys requires bi-directional communication capabilities. The questions are sent from the third-party to the cloud which then send it to the device either wirelessly or through a wired connection. The patients answers the questions, and the responses are sent back to the cloud and third-party either wirelessly or through a wired connection.

Software Application for Structured Testing Protocol

In one embodiment, there is provide a software application for structured testing protocols such as: hospital admission control; high risk patient populations control; assessing efficacy of a medication therapy control; and prior to a physician visit control.

1) Hospital Admission Control

A large number of procedures are currently cancelled on the day of scheduled procedures because patients are not within the specified glucose control range. This causes significant costs in both labor and facilities to the hospital as the physician and operating room time cannot be quickly rescheduled.

Structured testing may be used in the hospital setting around three use cases. First, patients with diabetes that have a scheduled hospital procedure would be given a structured testing regimen to follow for a certain number of days pre-admittance to ensure that their glucose is within a range specified by their physician. Secondly, once the patient is admitted, structured testing can be used to maintain glucose within a specified range so that the length of hospital stay is minimized and complications associated with diabetes are avoided. Thirdly, once the patient is released from the hospital, structured testing will be used to ensure the patient is within a specified glucose control range for a specified number of days post hospital release (e.g., 30 days), which will minimize diabetes related complications which may require additional medical attention or hospital readmission.

2) High Risk Patient Populations

Structured testing may be used for patients who are at high risk for low blood glucose (hypoglycemia) or high blood glucose (hyperglycemia) events to help them maintain their blood glucose level within a target range. This structured testing would include patients that are poorly controlled, as well as adolescent patients who need help to transition to monitoring their own glucose levels, and elderly patients who are not good at remembering to test. By having the blood glucose meter to prompt these patient populations to test at specified times, the patient will be more compliant with the recommended testing regimen.

3) Efficacy of Medication Therapy

Structured testing may be used to determine the efficacy of current or new medication therapy on glucose control. By having patients test on a specified regimen, a pattern of glucose control can be established. Along with the information that is inputted in the blood glucose meter regarding the time, date and amount of a specific medication taken, the blood glucose levels surrounding the time of injection/ingestion will indicate how quickly the medication takes effect as well as how long the medication remains effective. If a patient follows the structured testing regimen and is shown to be outside of the recommended blood glucose target range, changes to the type or amount of medication can be recommended by the physician.

4) Prior to a Physician Visit

Structured testing may be used to guide a patient to test for a specified period of time using a structured testing regimen prior to a physician visit in order to obtain the necessary blood glucose level trend information needed to assess the patient's current state of disease and any changes to the therapy or testing regimen that may be required to keep the patient within blood glucose targets.

Software Application for Behavioral Feedback and Clinical Adherence to Patient

In one embodiment, there is provide a software application for behavioral feedback and clinical adherence to patient.

One reason why patients do not currently self-test their blood glucose levels with the frequency suggested by their physician is because blood glucose levels are not meaningful to the patient if the patient does not understand the correlation between blood glucose levels and their diet, exercise, and/or medication. As such, a software application may provide behavioral feedback to a patient. The behavioral feedback would try to make a patient's blood glucose level and/or other biometric data more meaningful to them and, therefore, engage them in active management of their disease through more frequent blood glucose testing or uploading of other biometric data. The application would also have the capability of providing medication and blood glucose testing adherence messages.

The software app may work in any device that is capable of receiving information including (a) BGM meters; (b) sensor based devices; (c) cell-phones including select features and smart phones; (d) connected biometric monitoring devices such as Bluetooth enabled blood-pressure meters; (e) home monitoring units; etc.

Based on the blood glucose level or other biometric data entered or communicated to the cloud/server, the application would deliver a response to the patient that provides feedback that would include an encouraging remark or corrective behavior modification. This feedback may be based on a single blood glucose test result or the feedback may be based on a trend observed over time. For example, a feedback response based on a single BG test result may be: (a) "120=in target range. Keep up the good work"; (b) "50=below target range. Take 15 grams of a fast-acting carbohydrate and re-test in 15 minutes"; (c) "200=above target range. Please call your physician"; or (d) "200=above target range. Inject one unit of insulin."

Feedback that is based on a trend observed over time would be analyzed in the server/cloud and the feedback would be generated by algorithms. Types of feedback responses based on a trend of blood glucose data and/or other biometric data may be: (a) "120=in target range. Your post-meal BG levels are improved over last week"; (b) "120=in target range. Your blood pressure and blood glucose levels are improved over last month. Keep up the good work!"; (c) "50=below target range. Your blood glucose levels have been volatile over the last week. Try to eat more fast-acting carbohydrate snacks."; (d) "200=above target range. Your blood glucose has been above target 30% of the time in the last week. It may be time to talk to your doctor about starting insulin therapy."; or (e) "Based on your blood glucose levels, blood pressure data and weight over the last month, you have taken a big step toward controlling your diabetes. That is fantastic and I am sure you are feeling more energy."

Messages may also be sent to the patient that improves medication adherence and effectiveness. For example: (a) "Take ABC and XYZ medications now. Perform a blood glucose test before and one hour post your meal."

Software Application for Providing Summary Reports Based on Historical Glucose and Other Biometric Information In one embodiment, there is provide a software application for providing summary reports based on historical glucose and other biometric information.

From a physician perspective, one of the challenges in treating patients with diabetes is the lack of a universal dashboard that provides a synthesis of historical glucose data for all meters used. All BGM companies have a version of a dashboard, but these dashboards are not compatible with competitor meters. From a patient perspective, these summary reports reside only the computer and are therefore not easily accessible. Further, the incompatibility results in information that is lost when a patient switches meters. As such, there is provided a software application that provides a summary report the users historical glucose reading. These summaries, which can exist for different periods of time, will enable the patient to track his performance over significant periods of time. The summaries, which can be extended to all biometric information (e.g., glucose, cholesterol, weight), will enable a patient to better manage his co-morbidities. The software application adapts existing summary reports, and presents it in a manner that is easy to access by the patient. There are different use cases for this software application.

(1) HCP/Physician Facilitates Download—Patient Visits HCP Office for a Consultation.

Prior to or during the visit, the glucose information from the meter is uploaded into the HCP's computer either wirelessly or through a wired connection. Software that is present in the system in the cloud, or physicians computer, analyzes the historical glucose data, and generates a summary report for the physician to view. The physician reviews the summary reports, makes recommendations, and sends the approved summary report back to the patient's device either wirelessly or through a wired connection.

(2) System Generates Reports and Automatically Downloads—Patient Sends Glucose Data from Device to Cloud Wirelessly or Through a Wired Connection.

Information is analyzed in the cloud, either automatically or with input from humans. Summary report is generated, and is sent back to the patient either wirelessly or through a wired connection.

(3) Patient Customizes Report and Self-Downloads—Patient has Several Summary Reports that are Stored on the Device or in the Cloud. Patient Chooses the Reports that are relevant to his needs and customizes them as appropriate.

Software Application for Providing Heuristic Meal Announcements

In one embodiment, there is provide a software application for providing heuristic meal announcements. One problem with meal announcement (or bolus calculators) used today is that they force the user to count carbs. Another problem is that the carb count is often very inaccurate. A third problem is that carbs are not the whole story; fat content, glycemic level, and other factors influence how food is converted into glucose—this is also influenced by each patients individual physiology.

As such, provided herein is a software application where the meal announcement is tailored to a specific patient's eating habits and physiology. One method is described, but many variations may be contemplated. The software application may be provided in a CGM with a function similar to a bolus calculator. The CGM is integrated with an insulin delivery system in such a way that insulin delivery information is retrievable or in some way available to the CGM processor. The CGM is also interfaced with a PC application. The system may or may not be a closed loop control system. The PC application provides a means for the user to define meals or portions of meals, in any fashion that is convenient to the user. It may provide pick-lists for meals/portions that are common, to assist the user in these definitions. These meals may also have associated with them heuristic amounts (e.g., large, small), carb values, fat content, glycemic index, or any other factor they may attribute to metabolic conversion.

In one embodiment, the user creates a list of common meal/portion names and characteristics and downloads these to the CGM (this functionality may also be included in the CGM; however, do to the limited data entry capability typical of CGMs it is probably more practical to incorporate it into a PC application). This information may also be prepared independently from the patient and downloaded into the CGM. However, the patient would likely need to tailor it to their own eating habits. New meal names may be added or subtracted at any time.

The software application may also take into account personal therapy factors such as carb ratio, insulin sensitivity, and basal rate. It may use these to also associate meal bolus amounts or amount/time profiles with the meal name. However, since these therapy factors may change in time, it is probably best to let the bolus calculator on the CGM which has the latest therapy parameters, to determine the bolus.

Currently, when the patient first selects a meal name when announcing a meal to the CGM, the UI would (in some embodiments) display all or some of the meal attributes and allow the user to edit. Alternatively, the UI would provide a means for the user to scale the amount (primarily related to carb count). For instance, the user may select small, medium or large. The bolus calculator would use the factors associated with the meal and estimate an appropriate bolus amount and profile (that is, an amount of insulin to be delivered at various amounts over time for some time period). Initially, the bolus calculator may delivery a dented amount less than the calculated amount in order to be conservative. The time associated glucose response, insulin delivery data including subsequent correction bolus and basal (both before and after the bolus and meal), therapy parameters and meal definition are stored in the CGM for subsequent analysis.

At some point after the data is acquired, either on the CGM or on an external PC or network processor or other external device, the data is analyzed as associated with this meal name. Using standard system identification techniques, more appropriate meal attributes are defined to be used the next time the meal is announced. These attributes may be optimized such that the glucose profile matches a desired profile (which may not be flat glucose in the euglycemic range in order to be more conservative). The optimal attributes may be determined or more conservative attributes may be used. If on an external device, they need to be downloaded into the CGM. The CGM bolus calculator may be less conservative in its derating with these new parameters.

This system may also be integrated with other meal announcement system, such as a food bar code reader or a standard bolus calculator. Another aspect of this invention would be to draw from the list of meals (either provided by the invention described above or by some other method) whenever low glucose is detected. The CGM may recommend a favorite food and amount. Or it may provide a list of food (perhaps rescue foods preselected), then after selecting the desired, it may provide a recommended amount, in either carb values or heuristic values.

Software Application for Incorporating Advanced Therapy Management Features without Requiring Training Before Purchase Advanced features such as a bolus calculator and treat-to-target are being contemplated for glucose measurement devices. It is desired that these devices be purchased without any training. However, it is likely that regulatory concerns will require the patient to undergo some training prior to using these features. So there is a conflict with the manufacturers desire to sell a product without requiring any training and providing these advanced features.

As such, in one embodiment, there is provide a software application for incorporating advanced therapy management features without requiring training before purchase. Said software application provides that the "out of the box" device have all of its features disabled. The software application includes a user interface that provides a means to enter a special code that would allow select features to be enabled (or would now display the enable item in a set-up menu so that the patient may at any time enable or disable the feature). The code would be provided per prescription from a doctor, just like prescription medication and devices are provided. The doctor's prescription would be an indication that the doctor had provided or was aware of the training required for that patient to use the select feature.

A unique code may be provided for each device serial number or a code may be good for a number of serial numbers. The manufacturer may provide a service to accept and confirm a prescription and provide the code. The code may be transmitted and entered into the device in a number of ways. One way would be for the manufacturer (or representative) to provide the code explicitly. The device would have a user interface option that would allow direct entry. Alternatively, the code may be entered via a PC connected to the device. Another method would be to connect the device to a PC that was connected remotely to a service that directly downloads the code into the device. The manufacturer may provide this service for a fee or provide it for free (or pay the customer to use it).

For a simple user interface, the code may be entered a number of ways. One possibility is a two button interface, where the left button increments each digit, starting at the left digit, and the right button selects the value for that digit and progresses the display to the second digit. Holding the right button for 3 seconds may return back one digit to make corrections. When the value for the final digit is selected, then the display may move to an enter field that can be selected by the right button.

A further method would be for a software application upgrade via prescription, with the new software including the advanced features. With this method, glucose measurement devices may be sold without a prescription to a large market, and a subset of this market that may benefit from the advanced features may get these enabled without exposing the features to untrained customers.

Software Application for Displaying Complication Risks Based on Average Glucose and Other Risk Factors Type-2 diabetes is a "boring" disease where symptoms are often not apparent to the patient—only doctors reminding the patient that they have diabetes. This dynamic creates the challenge of encouraging the patient to comply with their prescribed treatment. Elevated glucose is an abstraction to some patients, even though it may lead to health problems down the road or sudden problems such as a heart attack. As such, in one embodiment, there is provide a software application for displaying complication risks based on average glucose and other risk factors.

This software application provides a way to convey glucose data to patients such that the imperative of diabetes management is clear and present. The application can also lead to more consistent use of glucose measurement devices as it will provide a more relevant measure of health status. In addition, the application may provide the non-diabetic-expert clinician with a way to identify and diagnose health complications due to diabetes.

Results from clinical trials can be used to add context to the individual patient's current risk of complications, and relative change in their risk profile over time. For example, the UKPDS trial demonstrated a 16% reduction in risk for myocardial infarction for patients with an A1C of 7.0% compared to patients with an A1C of 7.9%.

The software application may apply to any glucose meter or monitor, and utilize glucose data (or other data relevant to diabetes). The key aspect of the software application is a table that associates key diabetes health complication risks with risk factors such as glucose data (and/or other relevant diabetes data). For instance, a risk of heart attack may be associated with average glucose over some period of time such as two weeks. The complication risk may be enumerated such as "a 1 in N chance of heart attack" within some standardized period of time such as 5 years, or it may be enumerated such as "likely to occur within N years," where N is the enumeration variable associated with average glucose level. The complication risk may also be enumerated as "50% more likely to occur than average person," or similar types of enumeration. The table would allow the software to lookup the complication risk(s) based on the current average glucose. The table may also be designed to allow lookup based on one or more other inputs; some input would be other calculations based on glucose such as number of hypoglycemic or hyperglycemic occurrences, inputs of other patient data relevant to diabetes, such as patient weight, A1C or whether the patient smokes or not. For instance, the complication risk may be different for a patient that smokes than for a patient that doesn't smoke but has the same average glucose. Current medication or therapy may also be an input to the table. Other patient information may be considered to determine risk of complications. Other than diabetes, the established risk factors for CVD are family history, hypertension, dyslipidemia, smoking, obesity, and ethnicity. For people with diabetes, gender is also a factor, as women with diabetes have increased risk for CVD compared to men with diabetes Besides CVD, the major complications associated with diabetes are "microvascular," causing damage to kidneys (nephropathy), peripheral nerves (neuropathy), and eyes (retinopathy).

The identified complication risk may be displayed to the patient either on the glucose measurement device, on the data analysis software application, or on a report that is generated from the data analysis software. Multiple results may be displayed in order of priority, either predetermined or configured by the doctor. They may be displayed graphically, such as a gauge where normal is indicated in green (and associated with a normal risk enumeration) and riskier values are associated with shades of yellow and red—the determined risk value would be indicated on this gauge. They may also be displayed on a standard modal plot with target ranges—the display may highlight complication risk gradations on this plot. When a complication risk exceeds a predetermined value, an indicator may flash or otherwise indicate that the risk has exceeded some warning level. This warning level may be configured by the doctor or patient.

The glucose (and other relevant) data may be analyzed over a period such as the previous two weeks of data. The analysis and display may occur periodically, or whenever the measurement device or software is activated. One possible procedure for this application is as follows:

1) display is activated;
2) most recent two weeks of data are retrieved from memory;
3) the average glucose level is determined from data;
4) other lookup table inputs and configurable parameters are retrieved from memory (or prompted for);
5) the complication risk and enumeration are determined firm the lookup table based on the inputs (e.g., average glucose, or other inputs and parameters); and
6) the complication risk is displayed on the device or PC.

The software application also may be configurable; e.g., the doctor may select appropriate complication risk categories that are deemed relevant for a particular patient For instance, for a particular patient the doctor may be more concerned about the risk of stroke than the risk of blindness, so the risk of stroke may be displayed on the meter.

Software Application for Providing a Bolus Calculator Safety Feature

In one embodiment, there is provide a software application for providing a bolus calculator safety feature.

A bolus calculator is a common product feature that allows patients to determine the amount of a bolus necessary in response to high glucose, or a meal, or both. More advanced bolus calculators have been disclosed that incorporate advanced physiological models and utilize glucose trajectory information that has not traditionally been available with SMBG meters, but is becoming more common with CGM systems, and may also be available with glucose-on-demand meters. One hazard associated with bolusing is the potential for overdose which may drive the patient's glucose to dangerously low levels. As such, there is provided a software application that provides a number of safety features that may be associated with a bolus calculator to enhance the patient's safety and improve outcomes.

Bolus Response Monitor—CGM

The remote device which contains the bolus calculator will initiate a process to specifically monitor the glucose response to the bolus. This would require a continuous glucose monitor capability, where CGM data is available to the remote in real-time. The remote will initiate a special process upon the start of the bolus (or the UI may need a means for the patient to initiate the monitor for non-pump injections). This process will estimate an expected glucose profile over a period of time using a physiological model associated with the patient's insulin action time and other patient physiological parameters, and based on trajectory, meal input data, and insulin input data, and potential other data such as exercise, health, time of day, etc. In addition, the process will estimate a "minimum" acceptable profile where the glucose has a minimum value at a predetermined low glucose safety limit. Also, the process will estimate a "maximum" acceptable profile where the predicted glucose has a maximum value at a predetermined high glucose management limit. Both of these limits may alternatively be determined based on a predetermined period of time below or above the limit—so that a brief excursion may be allowed. These profiles can be determined in a number of ways. For instance, they may be determined by increasing and decreasing the meal carbs to the point that the profile limits are reached. Or the meal timing relative to the bolus may be varied. Or any of the physiological model parameters may be varied. The profiles may be determined by cut-and-try methods or by backwards simulation to determine the initial conditions that may create the desired profile range.

The process would monitor each received real-time data to determine if it fell within the minimum and maximum profiles indicated at that point in time. If a predetermined number (one or more) of glucose readings fell outside the profile range, then the remote would provide an alarm notification to the patient and indicate that the glucose was lower or higher than expected, and perhaps recommend a course of action This process may provide a more timely notification to the patient of an upcoming adverse condition than traditional methods such as a simple linear projected alarm. These methods may be extended to other events such as meals (with no insulin, for example), other medications, exercise, and the like. This feature may be enabled by the patient or may automatically be turned on for high risk boluses, like for large boluses or boluses that occur when there is a large IOB.

Bolus Response Monitor—GoD

For the GoD system, it is assumed that glucose trend information will be available along with the glucose level reading. Here, a similar scheme as described above for the CGM system can be contemplated, except that the CGM automatically monitors glucose where the GoD (or SMBG) system is patient initiated, so the bolus response cannot be automatically continuously monitored. The patient may periodically (like every 5 minutes) take a GoD (or SMBG) measurement.

In one aspect, the monitoring process provides a prompt or alarm to the patient to perform one or more follow-up GoD (or SMBG) readings after the bolus was initiated. The timers for these prompts may be associated with one or more fixed, predetermined times relative to the bolus, such as 20 minutes and 45 minutes—these times may be pre-set at the factory or settable by the patient or health care provider or determined by a therapy optimizer tool that reviews a patient's past bolus histories to determine the critical times. These would represent critical times when it would be most informative to acquire glucose readings. The times may also be associated with the calculated glucose profile in some way.

This feature may be enabled by the patient or may automatically be turned on for high risk boluses, like for large boluses or boluses that occur when there is a large IOB. Also, subsequent prompts after the first prompt may be disabled if the reading from the first prompt was well within the safety range, and so on to subsequent prompts.

Bolus Response Monitor—SMBG

Trend data may be readily available for GoD systems, but not necessarily for SMBG meters. One distinct aspect of this invention is that the bolus calculator associated with an SMBG function may request a follow up SMBG some time (say 5 minutes) after the initial SMBG and bolus calculation in order to estimate rate. Then the bolus calculation can take into account a rate factor determined from the two SMBG values separated in time. The bolus may be adjusted based on this second reading, or the bolus start may be postponed until this second reading is taken, or it may be determined that the initial bolus fully delivered was too high and corrective action must be taken to prevent over-delivery. One embodiment would be to deliver a portion of the calculated bolus (say 70%) based on the initial SMBG, then deliver the remaining bolus (if any) upon the bolus calculation performed after the second SMBG is performed, now taking into account the glucose rate estimate.

One scheme for injectors would be to provide 100% of the bolus upon the initial SMBG and then after the second SMBG, if the bolus calculation indicated that too much insulin was delivered initially, warn the patient to ingest some correction carbs immediately.

Software Application for Diabetes Record Keeping Including a Fantasy Sports Game In one embodiment, there is provide a software application for diabetes record keeping including a fantasy sports game.

The acquisition of records for effective assessment of diabetes therapy is important but difficult for patients to adhere to. One reason for lack of adherence is a lack of understandable feedback as to the value of the records. As such, there is provided a software application that converts the acquisition and value of glucose and other records into outcomes of games, typically games based on athletic sports, such as baseball, football, basketball, hockey, etc. This conversion has the potential to provide more immediately understandable value of the record keeping since the outcome or advancement in the game is related to the records. In addition, users may get some entertainment or diversionary value from the invention. Furthermore, the glucose measurement can be properly relegated to "just a number," rather than a "personal failure," and yet still be a learning opportunity for future diabetes management.

In one example, each rapid-acting Insulin dose would be considered an "at bat" opportunity. A full set of baseball related outcomes and statistics can be developed to access incident dosage effectiveness. These numbers can be used to identify areas of success and improvement. The HCP ("batting coach") can identify which of the fundamentals need more work, and direct the patient to areas of education. A person can then follow their progress over several days by playing a full nine inning game.

The quality of the batting outcomes can be related to the quality of the record keeping about insulin, carbohydrate intake, activity, and glucose. With minimal amounts of records, the game can still be played, but some outcomes may be out of reach. By using more sophisticated tools, such as sensor-based glucose measurement devices that can record historical values, better batting outcomes are attainable. For example, with a sensor detecting the glucose throughout the action-time of the insulin dose, higher order measures can be computed, such as exposure to hypoglycemia and rapid increases in glucose. If these are acceptable, they can enhance the batting outcomes (make a double into a triple or home run).

The outcome of these at-bats becomes therapeutically meaningful. By reviewing the frequencies of different at-bat outcomes, the HCP can suggest therapy changes or educational material for review. Through the use of downloaded software and web-based services, the game can be extended, having individuals play each other, or having multiplayer modes, where people join teams and play against other teams. Fantasy sport extensions may be developed where a person or team playing "glucose controlled baseball" competes against fantasy teams of the outcomes of real major-league players To make the therapy/education intervention even more specific, optional "avatars" or batters can be associated with different days, times of the day, and or days of the week.

Other sports related metaphors may be developed, particularly for international markets Software Application for Advertising on a Meter In one embodiment, there is provided a software application for providing advertisements on an analyte measurement system.

Cost is a bather to adoption of glucose monitoring for many persons with diabetes. As such, a software application may be provide that may mitigate some or all of the cost associated with self-monitoring glucose, either using blood glucose meters or continuous glucose monitors, or the cost associated with insulin pumps. A software application is provided as a means to advertise on the handheld monitor and to sell the advertising. The products or services advertised may be anything, but may be specific to the diabetes industry. For instance, advertising for a type of insulin or dietary food supplement. Sales from this advertising may be used to offset costs of the device, costs of the disposable components of the glucose monitor (e.g., strips or sensors), even costs associated with HCP visits.

The advertising may be presented in many forms; e.g., a static image, an animation, a video, with or without our audio, or audio by itself. The advertisement may be presented in different contexts; for instance, an advertisement may present itself when the display is first activated. The advertisement may turn off automatically or be cleared by the patient, to return to the standard home screen. The advertisement may also be presented upon certain actions by the user. For instance, when the user initiates a blood glucose reading, the display may be presented and an advertisement associated with the blood glucose readings may be provided. The advertisement may also be presented at different frequencies, for instance, once every 6 display activations. The same advertisement may be repeated, or various advertisements may be cycled through, in order or randomly, or some other process (for instance, higher-paying advertisers may have their ads appear more frequently).

The advertisements may incorporate a means for ordering more supplies. For instance, the device may keep track of blood glucose strips used since the last order and prompt the user to order more strips when the time is appropriate.

Software Application Providing Optimal Storage Schedule of Analyte Data

This disclosure provides a software application (and/or method) whereby an analyte data storage schedule is provided which optimizes the amount of recoverable historical information while at the same time minimizing the amount of data stored. In the context of glucose monitoring, such an application finds use, for example, in both CGM and discrete glucose monitoring (DGM) systems. In a CGM system including both a hand-held device and an on-body component, one or both of the hand-held device and the on-body component may utilize such an application to optimize the storage of glucose data. For DGM systems, such an application can be used to encourage increased measurement frequency and/or optimized measurement timing by the patient. For CGM systems, such an application can extend the number of days historical glucose can be stored in the device without adding more memory. In an informatics context, such an application can be used to reduce the amount of raw data needed by the system. In systems where information on meals, insulin, and other related physiological activity is available, such an application can further enhance the storage schedule by using physiological glucose models that account for external inputs and physiological activities.

Figure 18:
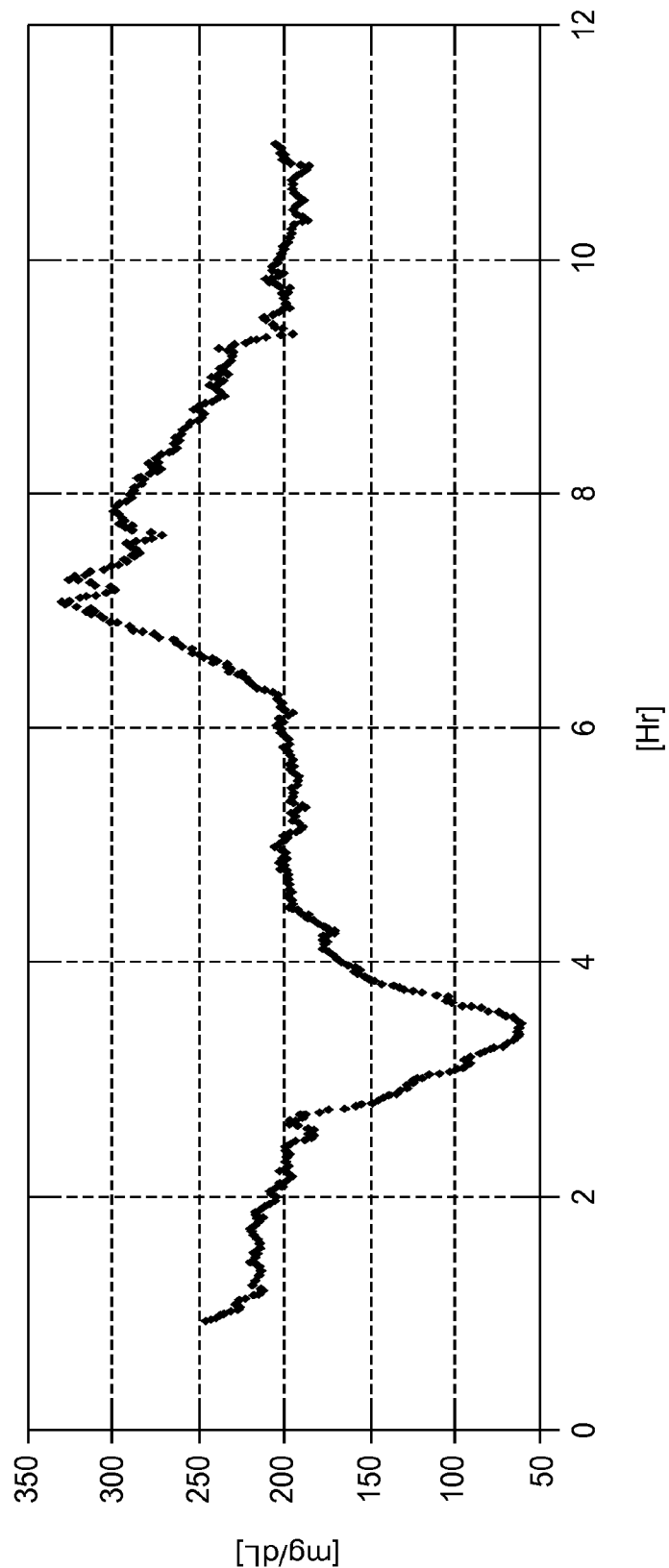
FIG. 18 provides a graph of a patient's glucose level recorded at one minute intervals.

FIG. 18 illustrates a theoretical patient's glucose as recorded at one minute intervals. Different regions in time exhibit different levels of glucose change. For example, periods between hours 3 and 5 are characterized by rapid and relatively constant rates of change, while periods between hours 5 and 6 barely exhibit any clinically significant glucose change. For systems that store glucose in a fixed sample period, the sample period may be a tradeoff between maximizing the utility of the glucose information and minimizing storage space. In order to capture the relatively fast excursions, a sample period in the order of 10 to 15 minutes is typically a good compromise.

Figure 19:
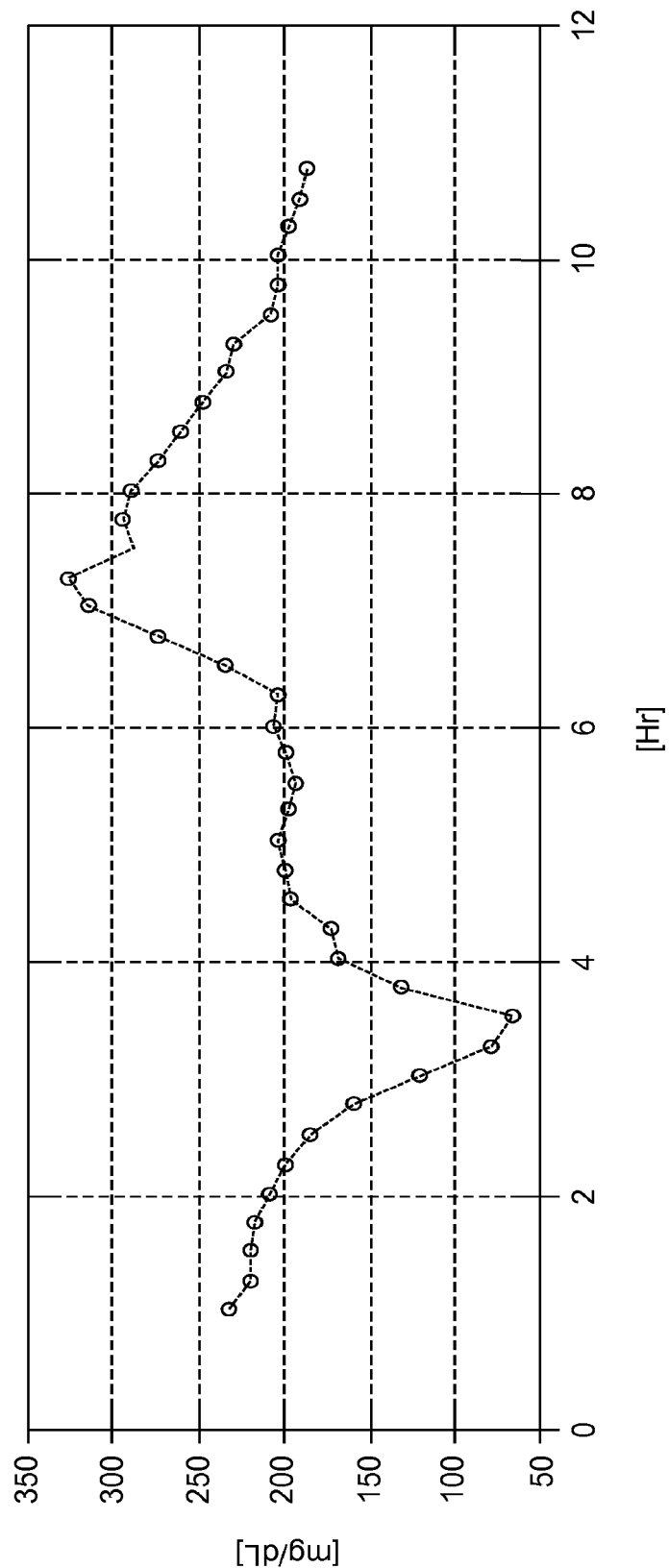
FIG. 19 provides a graph of a patient's glucose level recorded at a fixed sample interval of 15 minutes.

As can be seen in FIG. 19, a fixed sample interval of 15 minutes captures the general movement of glucose over time, even though a few sharp changes such as the one seen before the rapid descent around hour 3 is somewhat attenuated. On the other extreme, patient-initiated, asynchronous measurements may simply miss important features unless the patient is either in very good control or is fully aware of how their glucose changes over time in order to time the observations accordingly.

Figure 20:
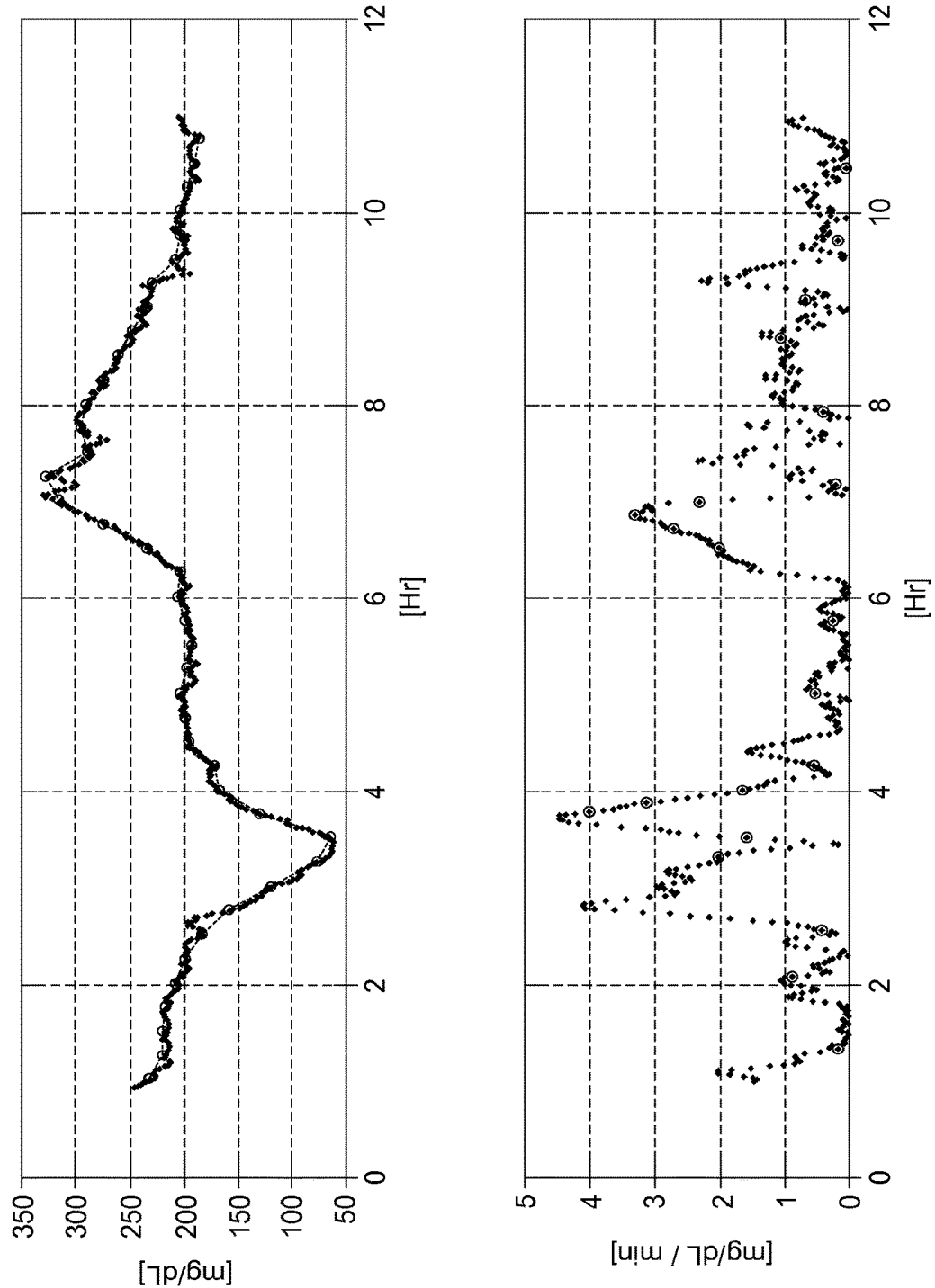
FIG. 20 provides a graph showing the glucose data depicted in FIG. 18, along with the absolute value of the instantaneous rates of change on the bottom plot. The circled points indicate points at which data is recorded (and/or a reminder is communicated to the patient to make a measurement) in an exemplary embodiment in which the glucose rate of change is used to estimate the time interval where glucose will change by a certain pre-determined amount from the current value.

In one embodiment, the application and/or method takes into account only the instantaneous glucose information and the glucose rate of change information. This information may be used to optimize the storage and/or measurement schedule. FIG. 20 displays the glucose data, originally recorded at 1 minute fixed sample intervals (top), along with the absolute value of the instantaneous rates of change (bottom).

For any measurement, the glucose rate of change may be used to estimate the time interval where glucose will change by a certain pre-determined amount from the current value. Consider, for example, a situation in which a 25 mg/dL change in glucose concentration is chosen as the pre-determined amount. Then, for any measurement, the absolute value of the rate of change will be used to divide the pre-determined amount, 25, in order to obtain the estimated duration. The system will wait until this estimated duration before making another measurement (and/or communicate a reminder to the patient to make a measurement). Once the time elapses, a measurement is made and recorded. The resulting observations are circled in FIG. 20. It should be noted that the pre-determined change in glucose concentration used to calculate the time until the next measurement and/or recording may be adjusted as appropriate to obtain a balance between the amount of data stored and the capture of clinically significant glucose change.

Figure 21:
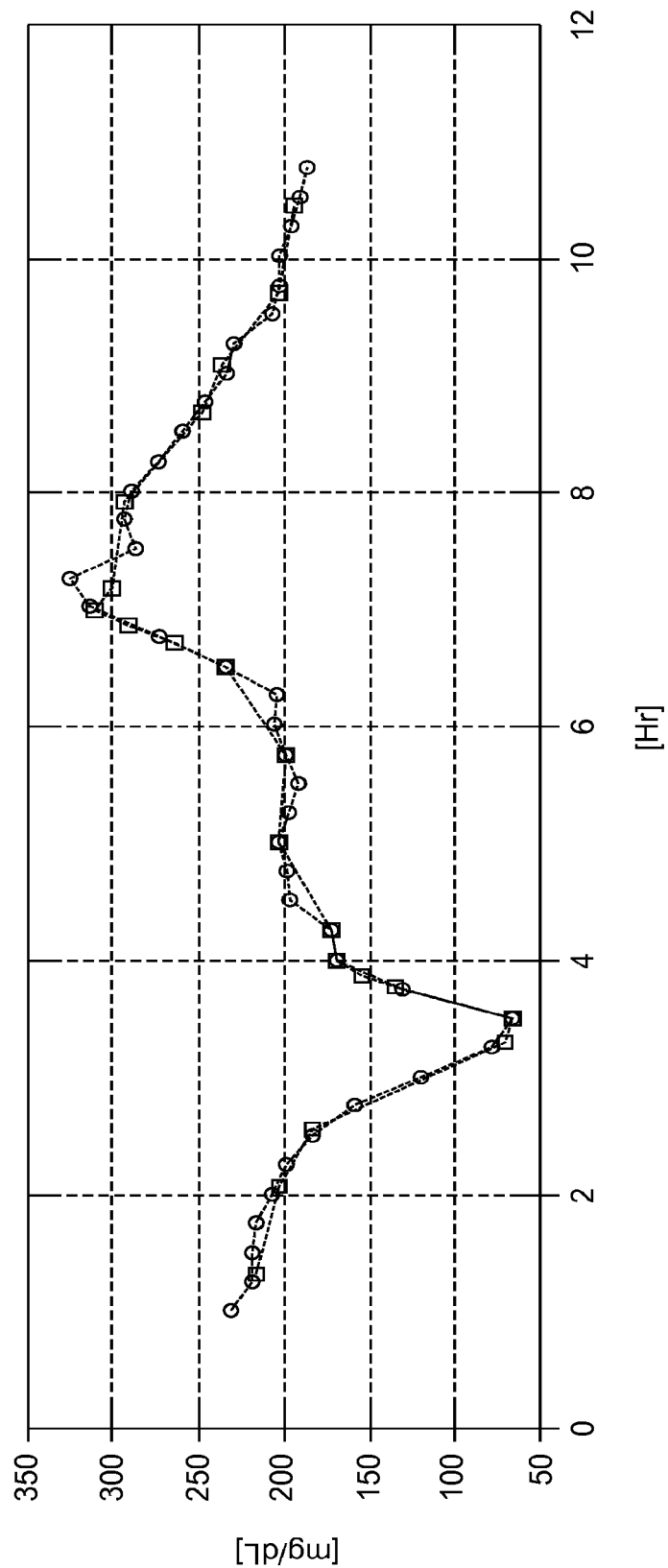
FIG. 21 provides a comparison between a fixed 15 minute sample interval (as shown above in FIG. 19) and a variable rate-based sample interval.

FIG. 21 compares the result presented in FIG. 20 (squares) against a relatively frequent sampling schedule of 15 minutes as previously described in FIG. 19 (circles). Note that both manage to achieve similar glucose features, and that the variable rate-based schedule focuses on areas with more glucose change and places less emphasis on areas with little glucose change.

Additional complexities can be introduced, such as providing an upper and lower limit on the time interval between measurements. For example, one can set a lower limit of once per 5 minutes and an upper limit of once per 45 minutes.

For CGM system, where the latest 1-minute glucose data is available to the recording module (e.g., the on-body or the handheld component of the system), determining the time to the next recording can simply be based on the latest instance where the observed glucose value have changed at least the pre-determined amount with respect to the latest recording.

When historical glucose data is available in addition to the instantaneous glucose and glucose rate of change, a more complex approach can be adopted. For example, the use of an AutoRegressive (AR) model can be used, where glucose values at various future times can be estimated, and the shortest one that exceeds a pre-determined glucose change (with respect to the present glucose value) is used to determine when the next measurement should be made and/or recorded. Other approaches can also be used to estimate glucose values at a plurality of future times. One example is the use of polynomial fitting on the present and historical data to extrapolate these future glucose values.

When meal, insulin, exercise, or other relevant information is available, an extension of AR model, along the lines of the AutoRegressive with eXogenous input (ARX) model, can be used, where relevant information is added as the input to the ARX model to estimate future glucose values. As before, these future glucose values will be used to determine the time to the next measurement and/or recording.

In another embodiment, where both external information and historical glucose data is available, physiology-based glucoregulatory models such as Bergman's minimal model can be employed to determine the time to the next measurement and/or recording. Such an implementation may employ state observers such as a Kalman Filter, in which the glucose estimation variance can also be used as yet another criteria for the future measurement timing. This is because the longer the estimation horizon, the larger the estimation variance becomes. Unlike the simpler models previously mentioned, an erroneous glucose measurement at any observation instant can result in large residuals between the estimated current glucose and the latest glucose reading. This too can be used to shorten the time interval to the next measurement.

Software Application for Evaluating Patients Using Random Analyte Determinations and/or Analyte Determination Storage Times The present disclosure provides a software application (and/or method) designed to randomly generate analyte measurement times and/or analyte measurement storage times. Such an application finds use, for example, in the context of a CGM system utilizing an on-body component with or without a hand-held component. In one embodiment, the CGM system is configured to measure glucose concentration only at the time the measurement is to be stored in memory. In another embodiment, the CGM system is configured to continuously measure glucose, but only stores the glucose measurements at the designated time points.

The application and/or method is designed such that the times at which the analyte measurement (e.g., glucose measurement) is stored in memory are randomly generated within broad constraints. For example, the minimum number of glucose measurement storage times within a specific time period may be specified, e.g., 6 glucose measurement storage events per 24 hr period. These constraints may be based on clinical factors (e.g., minimal number of readings required as a basis for useful clinical decisions) and/or technical considerations (e.g., memory storage capacity of storage unit in an on-body component of a CGM system).

In one non-limiting example, a microprocessor of an on-body component of a CGM system is configured to run an application which generates the following random glucose measurement storage times:

Day 1: 2 am, 7 am, 3 pm, 8 pm, 10 pm, 11 pm
Day 2: 5 am, 8 am, 10 am, 11 am, 6 pm, 11 pm
Day 3: 1 am, 10 am, 11 am, 3 pm, 5 pm, 9 pm
Day 4: 1 am, 3 am, 5 am, 2 pm, 8 pm, 11 pm
And so on

Figure 22:
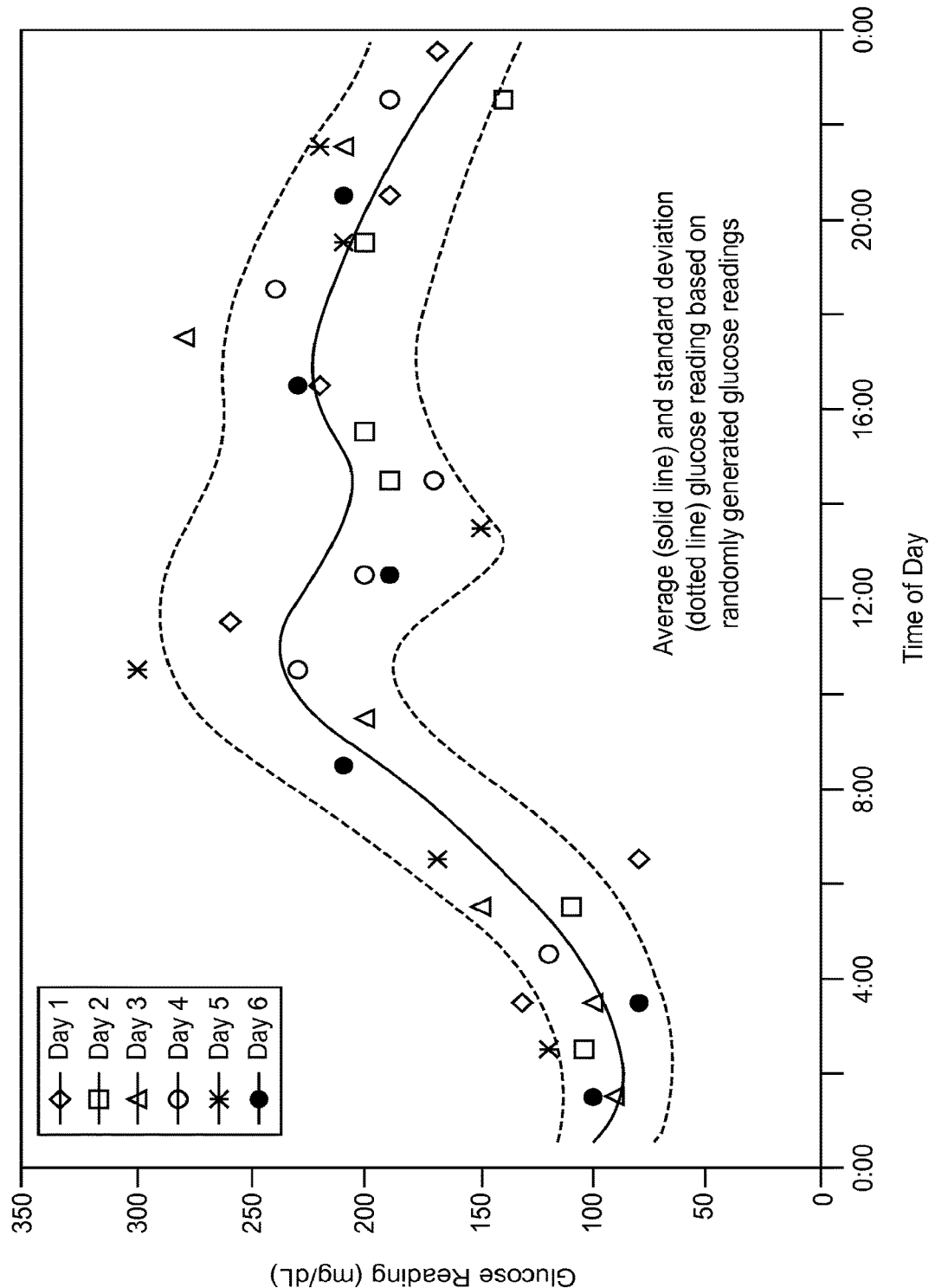
FIG. 22 is an illustrative plot showing the average glucose and standard-deviation lines for randomly generated glucose data from an implantable sensor based on a 6-day analysis period.

In one embodiment, the application and/or method functions as part of a system as follows: Based on the product use specifications, the patient wears the on-body component of a CGM system for a fixed number of days (e.g., 6 days) and then sends it to the manufacturer, an HCP or other suitable 3.sup.rd party who then extracts the data from the on-body component and graphically displays the data over, e.g., a 24-hour period. Alternatively, the data may be communicated from the on-body component to a hand-held component of the system and then sent from the hand-held component to the manufacturer, HCP or $3^{rd}$ party, e.g., via a wireless or wired network connection. In still another embodiment, the analysis may be performed on the hand-held component of the CGM system. In addition to plotting the data, the manufacturer, HCP, $3^{rd}$ party or the hand-held component itself may generate curves that show the average glucose reading and one or more standard-deviation lines (e.g., ±65% range, ±90% range). FIG. 22 is an illustrative plot that shows such a display with a single standard-deviation line. The results of this analysis may then be analyzed by HCPs, who can then recommend a suitable treatment protocol to the patient.

Software Application for Identifying Diabetes Self-Care Behaviors of Therapeutic Importance The present disclosure provides an application and/or method which uses clinically-informed algorithms to search glucose data acquired for an individual patient to reveal diabetes self-care behaviors. There are five main components to the operation of the invention: 1) defining "episodes" of interest, either daily activities or glucose-derived, 2) selecting a "kernel" episode for the search routine, 3) constructing "episode chains" of a sequence of episodes (including the kernel episode) and logical rules for the inclusion or exclusion of episodes in close proximity to the kernel, 4) associating one or more episode chains with a diabetes self-care behavior, and 5) displaying the findings of the search algorithms.

Episodes

This application and/or method uses episodes related to daily activities (e.g., meals, taking medications, exercise, etc.) as well as four main classes of glucose-based episodes: High, Low, Rise, and Fall. Each of these glucose episodes are defined by thresholds (as previously described in Provisional Application No. 61/442,085; filed Feb. 11, 2011; and entitled "Feedback from Cloud or HCP to Payer or Patient via Meter or Cell Phone"; the disclosure of which is incorporated by reference in its entirety and for all purposes). For each class of glucose episode, several instances (or "flavors") may be defined for use in the search algorithms. For example, two types of "High" glucose episodes may be constructed: "Extreme High" may have entrance/exit thresholds of 240/220 mg/dL and minimum duration of 15 minutes, while a "Moderate High" may have entrance/exit thresholds of 180/160 mg/dL and minimum duration of 2 hours. In this way, a clinically-informed hierarchy of severity of high glucose may be formed, such as a clinical statement to a patient of: "Try to never go above 240 mg/dL ("Extreme High"), and try to avoid going above 180 for more than 2 hours ("Moderate High")." In the example shown in Table 1, two activity-based episodes (Meal and Exercise) and five glucose episodes have been defined: "Low (L)", "High (H)", "meal-related Rise (m-R)", "low glucose treatment Rise (lt-R)" and "Fall (F)". In the absence of daily activity records, it is envisioned the search algorithms could be executed on glucose episodes alone.

TABLE 1

Episode and Logic Nomenclature Definitions

| Episode Type Definitions | Meal | A patient-recorded meal event |
|---|---|---|
| | Exer | A patient-recorded exercise event |
| | L | Low glucose episode |
| | H | High glucose episode |
| | m-R | meal-related glucose Rise (starts above 75 mg/dL) |
| | lt-R | low glucose treatment Rise (starts below 75 mg/dL) |
| | F | glucose Fall to below 100 mg/dL |
| Logic Definition | not | Prefix meaning that episode type is not in the relative-time window |
| | *bolded* | This episode is the "kernel" of the search routine, which starts the search algorithm |
| | \| | "Logical OR (any item(s) can be "true" for the entirety to be "true")" for more than one episode type in the chain position |
| | & | "Logical AND (all items must be "true" for the entirety to be "true")" for more than one episode type in the chain position |
| | Time Slot | amount of time before/after an episode to look for other episodes of interest in the chain |

Kernel Episode Selection

The "episode kernel" is the episode which initiates the search algorithm for each episode chain, and there is only one kernel per chain.

Episode Chain Construction and Search Logic

Using the kernel as the starting point, other episodes before and/or after are defined to specifically identify the self-care behaviors of clinical interest. A duration of time relative to other episodes in the chain would be defined for each "Relative Time Slot". For example, 2 hours may be used as the period of time between the beginning or end of the episode in each slot and the end or start time of the previous or subsequent timeslot (respectively). In the example below, all durations of "Time Slot" were set to 2 hours, but it is envisioned that the time slot duration setting may be different for some time slots, or even unique for each link in each episode chain. Furthermore, the logic may enforce the absence of one or more episodes in a position of the chain. The presence of an excluded episode would reject the candidate chain from being selected as a match to the self-care behavior.

Further logic is envisioned which would resolve "overlapping chains". In these cases, when chains are identified that are coincident in time, there may be logic which either allows them to both remain identified for further analysis (allowing the clinician to review and sort out the overlapping), or there may be a hierarchy of importance or precedence of one chain over another (helping the clinician by removing conflicting self-care behavior activities identified at the same time).

Association of Episode Chains and Self-Care Behavior

One or more episode chains are associated with a clinically-meaningful self-care behavior. These behaviors would be selected because of the risk they pose to the patient and/or the possible interventions (medications, education, etc.) which may be offered to reduce the future occurrence of the episode(s).

Table 2 below provides an example of the association of various episode chains with various diabetes self-care behaviors with the kernel episode identified as bold text within each chain (row of the table).

TABLE 2

Logic Definition for Identifying Self-care Behaviors

| Inappropriate Diabetes Self-care Behavior | Episode Chain Relative Time Slot | | | | |
|---|---|---|---|---|---|
| | 1 | 2 | 3 | 4 | 5 |
| Meal-to-Insulin Amount Mismatch, too little insulin | not F | *m-R* | H | — | — |
| | *Meal* | m-R \| lt-R | Not F | — | — |
| | *Meal* | H | — | — | — |
| | H | *Meal* | H | — | — |
| | H | *m-R* | Not H | — | — |
| Meal-to-Insulin Timing Mismatch, insulin too late | not F | *m-R* | Not H | — | — |
| | *Meal* | m-R \| lt-R | F | — | — |
| | *H* | F | not m-R & not lt-R | — | — |
| High overtreatment, without rebound High | *H* | L | not H | — | — |
| | *H* | F | not H | — | — |
| | *H* | *Meal* | F | Not H & Not m-R | — |
| | *H* | lt-R | not H | — | — |
| High overtreatment, with rebound High | *H* | L | H | — | — |
| | *H* | lt-R | H | — | — |
| | *H* | F | m-R \| lt-R | — | — |
| | *H* | *Meal* | F | H | — |
| | *H* | *Meal* | F | m-R | — |
| | *H* | L | lt-R | — | — |
| High undertreatment | *H* | not L & not lt-R | H | — | — |
| Exercise-induced glucose drop | *Exer* | F | — | — | — |
| | *Exer* | L | — | — | — |
| Isolated High, too little insulin | not L & not lt-R & not H & not Meal | *H* | not L & not lt-R & not H & not Meal | — | — |
| Rescue Carb | L | *Meal* | — | — | — |
| Low overtreatment, without rebound Low | not H | *lt-R* | not L | — | — |
| | F | *m-R* | not L | — | — |
| | L | *lt-R* | not L | — | — |
| | not H | *L* | H | not L | — |
| Low overtreatment, with rebound Low | not H | *lt-R* | L | — | — |
| | F | *m-R* | L | — | — |
| | L | *lt-R* | L | — | — |
| | L | H | L | — | — |
| Low undertreatment | *L* | not H & not lt-R | L | — | — |
| Isolated Low, too much insulin | not L & not lt-R & not H | *L* | not L & not lt-R & not H & not Meal | — | — |

Table 3 below provides a detailed example of the association of specific episode chains with specific diabetes self-care behaviors. A 2 hour period was universally applied to all time-slots between episode chain links.

TABLE 3

| Kernel Start Time | Description (bolded indicates kernel episode) |
|---|---|
| Day 1, 5:49AM | m-R, H: Meal-to-Insulin Amount Mismatch, too little insulin |
| Day 1, 4:59PM | m-R, not H: Meal-to-Insulin Timing Mismatch, insulin too late |
| Day 1, 10:20PM | H: Isolated High, too little insulin |
| Day 2, 1:59PM | L, Meal: Rescue Carb |
| Day 2, 2:11PM | not H, lt-R, not L: Low overtreatment without rebound Low |
| Day 2, 10:20PM | Meal, H: Meal-to-Insulin Amount Mismatch, too little insulin |
| Day 4, 8:23AM | H, Meal, F, not H & not m-R: High overtreatment, without rebound High |
| Day 5, 3:55AM | not H, lt-R, not L: Low overtreatment without rebound Low |
| Day 5, 6:56AM | m-R, H: Meal-to-Insulin Amount Mismatch, too little insulin |

TABLE 3-continued

| Kernel Start Time | Description (bolded indicates kernel episode) |
|---|---|
| Day 5, 9:32AM | H, Meal, F, H: High overtreatment, with rebound High |
| Day 5, 1:26PM | not H, lt-R, not L: Low overtreatment without rebound Low |
| Day 5, 2:56PM | m-R, H: Meal-to-Insulin Amount Mismatch, too little insulin |
| Day 5, 6:36PM | F, m-R, not L: Low overtreatment without rebound Low |
| Day 5, 8:06PM | m-R, not H: Meal-to-Insulin Timing, Mismatch, insulin too late |
| Day 6, 9:37AM | H, Meal, F, m-R: High overtreatment, with rebound High |
| Day 6, 2:17PM | F, m-R, not L: Low overtreatment without rebound Low |
| Day 6, 2:19PM | Meal, m-R, F: Meal-to-Insulin Timing Mismatch, insulin too late |

Display of Search Output

The number of episode chains and self-care behaviors found by the search algorithms could be displayed as a "scorecard", indicating which self-care behaviors were most prevalent. An example of such a scorecard based on the data of Table 3 is provided below in Table 4. In addition, comparison to historical findings for that patient may be shown. Alternatively, a comparison of self-care behaviors needing improvement for a particular patient could be compared to a population of similar patients. These displays would enable efficient sorting of potentially effective interventions to reduce the number of self-care behaviors problems experienced by the patient. It is envisioned that the display of the results would also provide access to further details and guidance for expert- or evidence-based techniques for addressing these self-care behaviors in a positive way.

Figure 23:
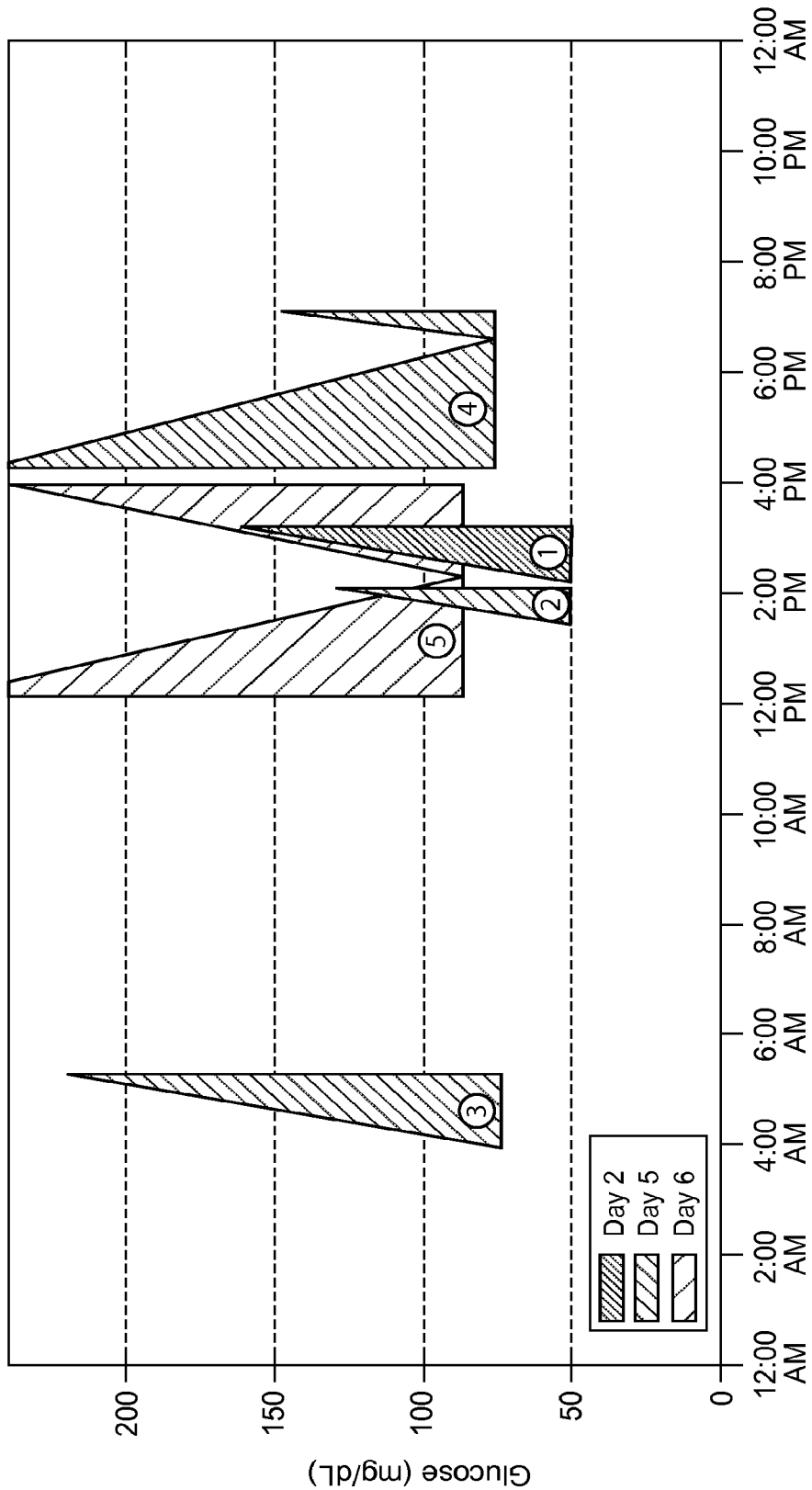
FIG. 23 provides a time of day plot including an overlay of a 30 hr plot for the self-care behavior "Low overtreatment without rebound Low".
Figure 24:
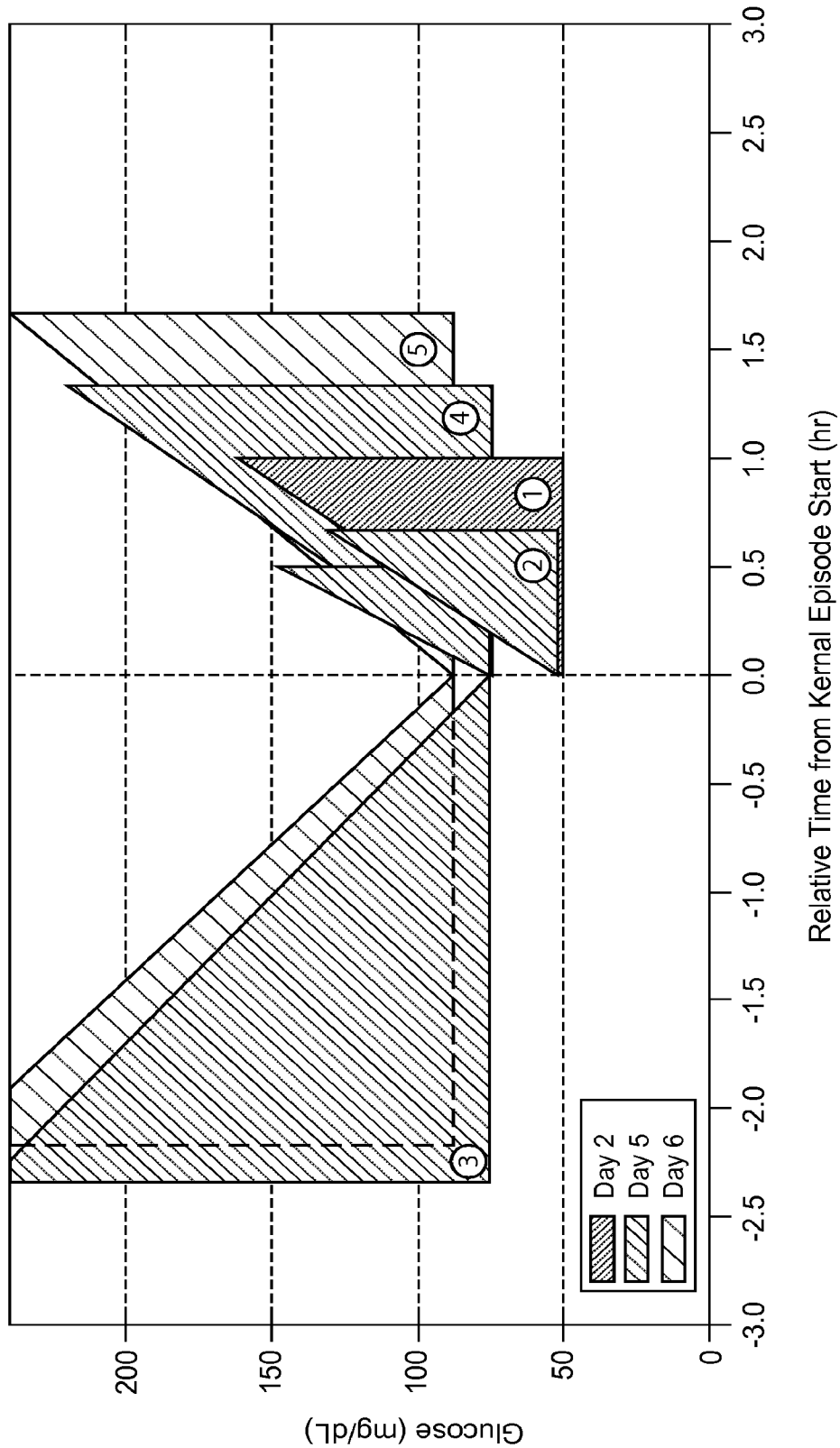
FIG. 24 provides an overlay of self-care behavior patterns relative to "kernel" start time for the "Low overtreatment without rebound Low" behavior.

In order to provide further insight into the timing and potential patterns of the self-care behaviors experienced by the patient, the episode chain or chains associated with each behavior may be shown in a time-of-day plot, with each episode indicated within the chain. For example, a 24 or 48-hour plot may be used to ensure that episodes that occur after midnight on the day of the kernel episode are shown to be after the kernel, as opposed to "wrapping" to the morning period. FIG. 23 provides a time of day plot including an overlay of a 30 hr plot for the self-care behavior "Low overtreatment without rebound Low" which is based on the data provided in Table 3. The start time of the kernel episode is indicated to provide reference to the other episodes in the chain. As an alternative display method, the chains could be displayed along a time axis that is referenced to the start time of each kernel episode of each chain type or self-care behavior. An example of such a display is provided in FIG. 24 which provides an overlay of self-care behavior patterns relative to kernel start time for "Low overtreatment without rebound" based on the data from Table 3. This format has the potential to be instructive to the clinician and patient about the recurring cause-and-effect relationships of the episodes of interest.

TABLE 4

| Summary Table, "Self-Care Scorecard" Identified Self-Care Behavior | Count |
|---|---|
| Low overtreatment without rebound Low | 5 |
| Meal-to-Insulin Amount Mismatch, too little insulin | 4 |
| Meal-to-Insulin Timing Mismatch, insulin too late | 3 |
| High overtreatment, with rebound High | 2 |
| High overtreatment, without rebound High | 1 |
| Isolated High, too little insulin | 1 |
| Rescue Garb | 1 |
| Grand Total | 17 |

Software Application for Adjusting Signal Processing Parameter

The present disclosure provides an application and/or method designed to provide a tradeoff between responsiveness to true blood glucose (BG) excursions and reduction of false perceived changes in glucose in the context of interstitial glucose (IG) monitoring. The application and/or method includes (a) providing a single manually adjustable parameter, e.g., to a patient and/or the patient's Health Care Professional (HCP) to best utilize the sensor-based glucose monitoring information, (b) providing an event dependent parameter table in order to adjust the sensor's filtering in response to the patient's declaration on a current or impending event (e.g. snack, exercise, sleep), and/or (c) providing a programmable schedule based parameter table that can be adjusted by the patient or the patient's HCP to best fit the patient's needs.

Another embodiment includes a non-user accessible event-driven algorithm which adjusts the sensor's filtering in response to events (e.g. a snack, exercise, sleep, time of day, environmental condition or recent historical signal attributes).

Figure 25:
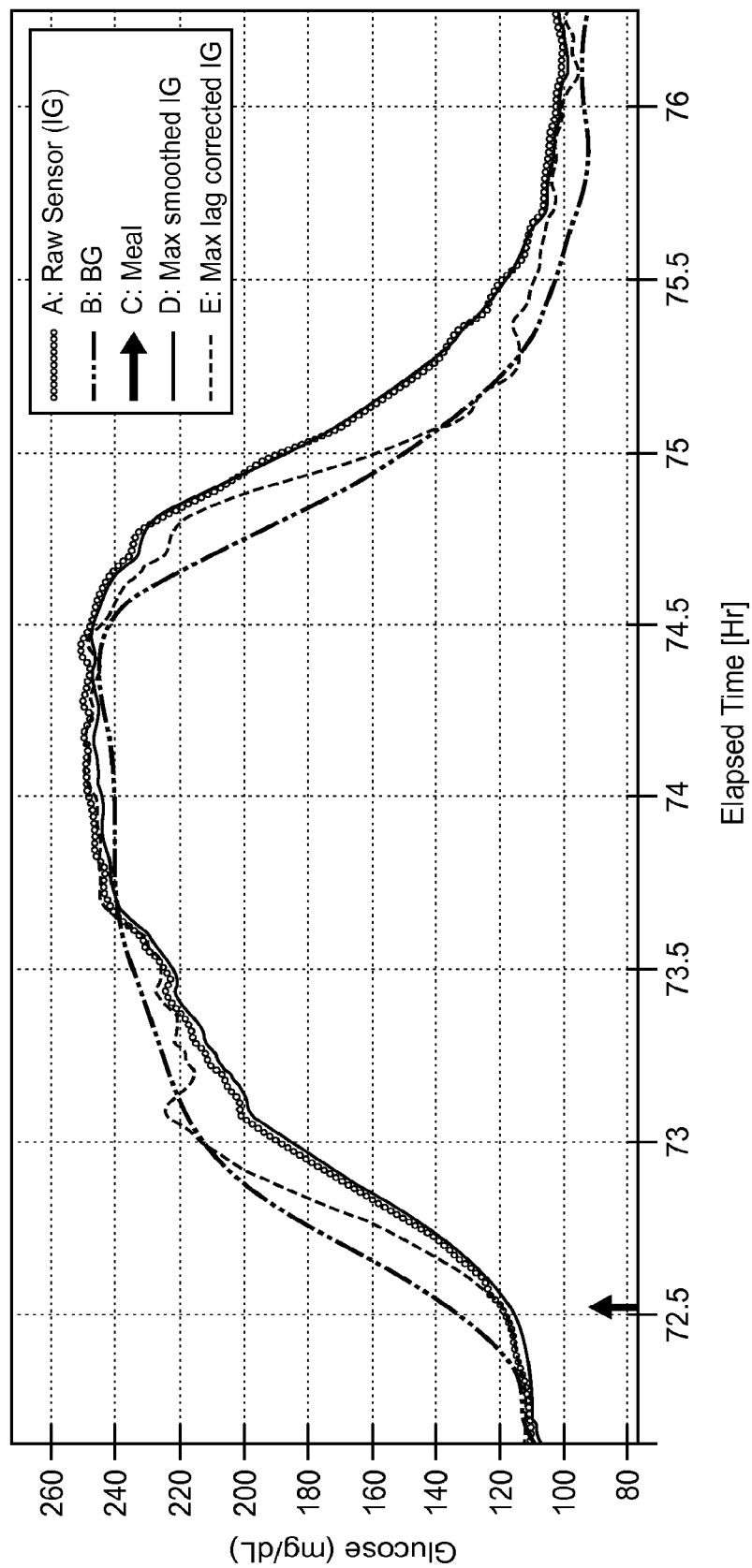
FIG. 25 provides a graph which illustrates interstitial glucose (IG) lagging with respect to blood glucose (BG), and the different effects of maximally smoothed and maximally lag-corrected IG signals.

Sensor-based glucose monitoring that draws its sample from the sub-cutaneous tissue measure interstitial glucose (IG). IG lags from blood glucose (BG), resulting in a discrepancy between the two during non-quiescent periods. Lag correction methods generally reduce this discrepancy at the expense of increased noise. FIG. 25 shows a raw sensor signal measuring IG (curve A) and a reference BG (curve B) in response to a meal (icon C) and the subsequent recovery due to the corresponding insulin bolus. A signal processing algorithm that maximizes lag correction, that is, minimizes the correlation between the IG error (with respect to BG) and the BG-to-IG dynamics (such as IG rate of change), is shown as curve E in the figure. Even minimal noise evident in the raw sensor signal results in an exaggerated fluctuation in the maximally lag corrected signal. In contrast, the maximally smoothed signal (curve D), eliminates most of the sensor noise, at the expense of larger IG error when glucose values are changing. Further discussion on the general tradeoff between a maximally lag corrected process and a maximally smoothed process is provided in the U.S. patent application entitled "Dual Algorithm Method for Independent Glucose Value and Rate Calculation", assigned client Ref. No. 10666USL1, the disclosure of which is hereby incorporated by reference in its entirety and for all purposes.

For Continuous Glucose Monitoring (CGM) systems, the general goal is to obtain a good tradeoff between the improved pointwise accuracy afforded by the maximally lag corrected approach and the sample-to-sample noise suppression afforded by the maximally smoothed approach.

Unlike CGM systems, real-time on-demand systems and retrospective therapy management systems can assume a more asynchronous timing between glucose measurements. In some embodiments, CGM systems can benefit from the disclosed application and/or method by taking advantage of the fact that the power management of some CGM system handhelds will only turn on the screen at the patient's initiative. For these three cases, an on-demand asynchronous algorithm that can perform an adjustable tradeoff point based on the time spacing of previous measurements is provided. In addition, for the first two cases, a priori information provided by the patient, the patient's HCP or another suitable party can be utilized to perform an adjustable tradeoff point based on both previous and anticipated future measurements.

Figure 26:
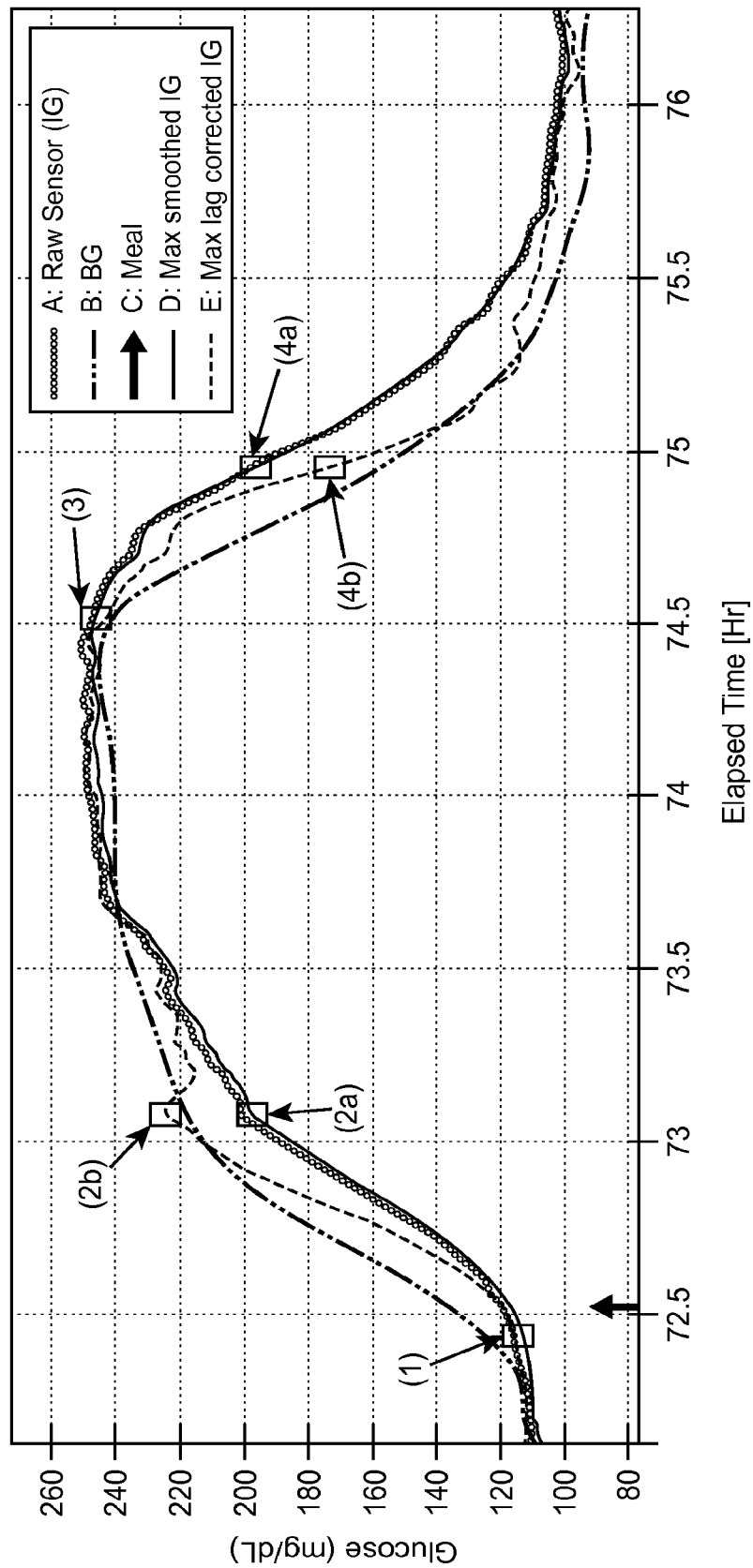
FIG. 26 provides the graph of FIG. 25, but indicates glucose measurements taken at several discrete points in time.

Consider the same patient as shown in FIG. 25, but as shown in FIG. 26, where instead of continuously checking glucose levels the patient only performs a check just prior to a meal (1), approximately 30 to 45 minutes after a meal (2a or 2b), approximately 2 hours after a meal (3), and right after a correction bolus (4a or 4b). In general, whenever the maximally smoothed and maximally lag corrected values differ (e.g., 2a vs. 2b & 4a vs. 4b), the maximally lag corrected values better represent the changes in glucose in response to a meal and a correction bolus. For this patient, and given the timing of the meal and glucose monitoring schedule, the maximally lag corrected value is preferred over the maximally smoothed value.

Figure 27:
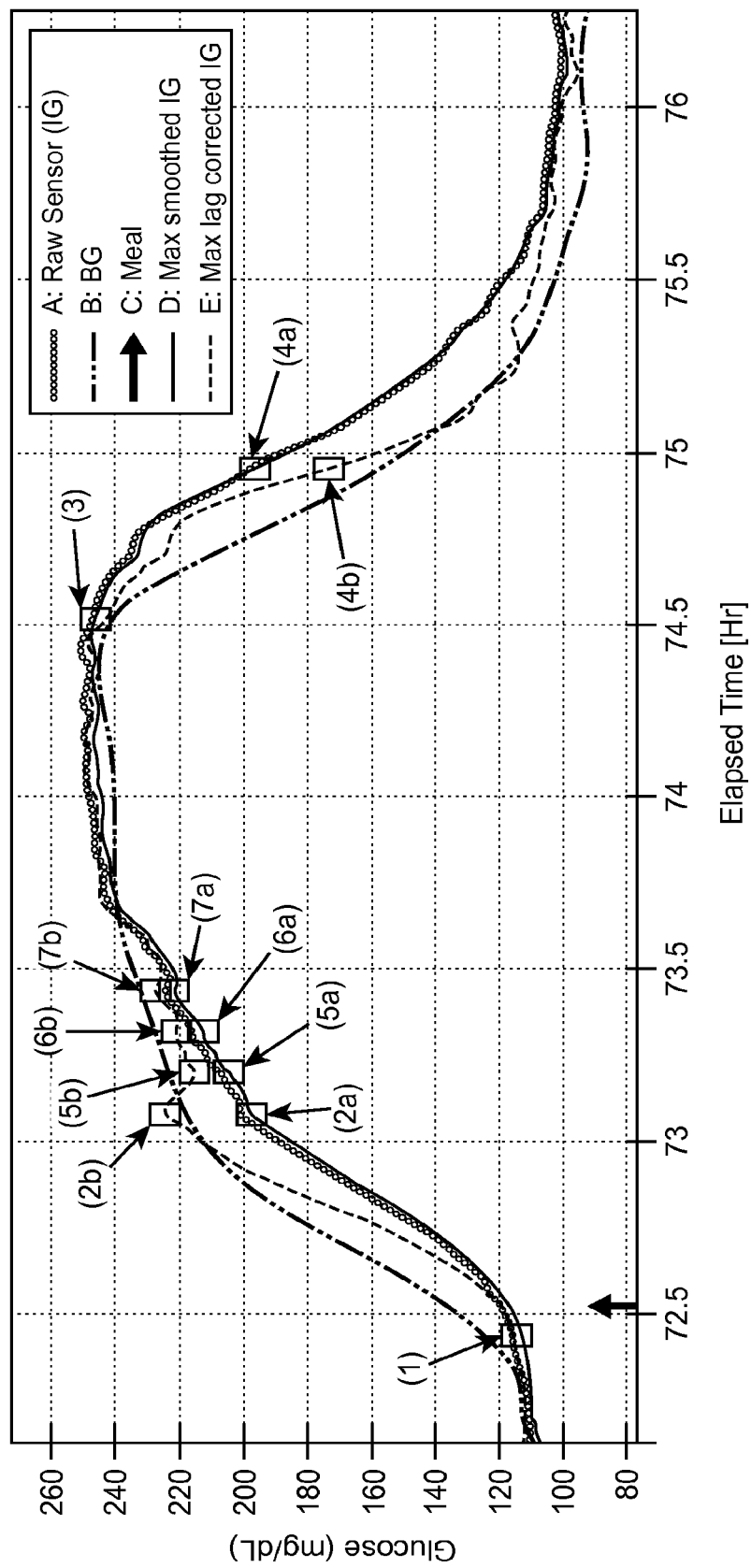
FIG. 27 provides the graph of FIG. 25, but indicates glucose measurements taken at shorter time intervals relative to the measurement schedule depicted in FIG. 26.

Suppose the same patient were to take measurements at a shorter time interval to check the glucose response to the same meal as shown in FIG. 27, but suppose the patient retains the same insulin dosing as before. When the maximally lag corrected process is chosen to generate the sensor's glucose values, the patient sees the data history (1)-(2b)-(5b)-(6b)-(7b)-(3)-(4b), compared to (1)-(2a)-(5a)-(6a)-(7a)-(3)-(4a). During the relatively successive string of measurements from (2b) through (7b), the patient may falsely infer that in addition to a relatively high glucose range (around 220 mg/dL), the glucose level is relatively level with a noticeable degree of fluctuation.

For an infrequent and/or inexperienced patient, this can be detrimental in several ways. First, the device may be perceived as unreliable due to the observed sample-to-sample variation. Second, an inexperienced patient might take the fluctuations on face value and attempt to falsely rectify the situation by either suspending their extended bolus delivery, ingesting a small amount of carbohydrate to reduce the drop, or adding more insulin. For a frequent patient, this means that the close spacing between observations (2b)-(5b)-(6b)-(7b) loses much of its trend information.

In one embodiment, the disclosed application and/or method provides a single manually adjustable parameter to the patient, the patient's HCP and/or other suitable party to change over time, wherein the parameter favors a maximally lag corrected signal processing at one end of the parameter's range, and favors a maximally smoothed signal processing at the other end. In one embodiment, a parameter is provided which takes the range of 0 to 1, which multiplies the maximally smoothed signal, and which automatically applies the complement of this parameter to the maximally lag corrected signal. The sum of the parameter and its complement equals 1. For example, when a new patient is given a glucose monitoring system for the first time, with a relatively frequent recommended monitoring schedule while retaining the same or no correction bolus. This could imply adjusting the parameter to favor better pointwise accuracy (i.e. maximally lag corrected process) since data will most likely be viewed through a therapy management system with the patient's HCP to obtain a baseline.

As the patient gains a better understanding on how much their glucose can change over time and in response to various events, and as the patient moves away from single meal boluses and instead relies on frequent glucose checks to fine tune small correction boluses, the manually adjustable parameter can be set to include more smoothing so that the difference between successive measurements contain more rate information than noise. At any point in time, should the patient need to change the frequency of correction bolus, the parameter can be tuned up or down accordingly.

In another embodiment, the disclosed application and/or method provides pre-set event choices (e.g. exercise, meals, snacks, meeting, etc.) that can be pre-associated with a particular level of this adjustable parameter. The values may have initial recommended settings based on population studies or a priori data from the same patient, and can be adjusted by the patient, HCP or other suitable party over time. Alternatively, the values are pre-set and cannot be altered by the patient, HCP or other suitable party. Based on a known or planned event, the patient can then choose their best event mode, so that the subsequent glucose observations will be processed using the most appropriate tradeoff between observed responsiveness and observed smoothness.

In yet another embodiment, the disclosed application and/or method provides a programmable schedule based on time of day, day of the week, or other calendar-based schedules which can be set by the patient, HCP or another suitable party.

In yet another embodiment, the pre-set event choices can be made to map information entered into a personal information management system such as the calendar in the patient's mobile phone system or the patient's calendar stored in the cloud (e.g. Google Calendar, Windows Live Calendar, etc.). For example, knowledge of blocks of different kinds of events (e.g. presentation, seminar, group meeting, staff meeting, lunch break, etc.) could be associated with different likelihoods of glucose measurement to be queried by the patient. The likelihoods could then be used to provide an estimate of time interval between measurements. This moving estimate (across time) could then be used as an a priori automatic adjustment to the signal processing tradeoff.

In yet another embodiment, the pre-set event choices can be made to map information entered for an insulin pump in order to align the needs of glucose monitoring of glucose value, glucose trend, and insulin delivery profile.

Figure 28:
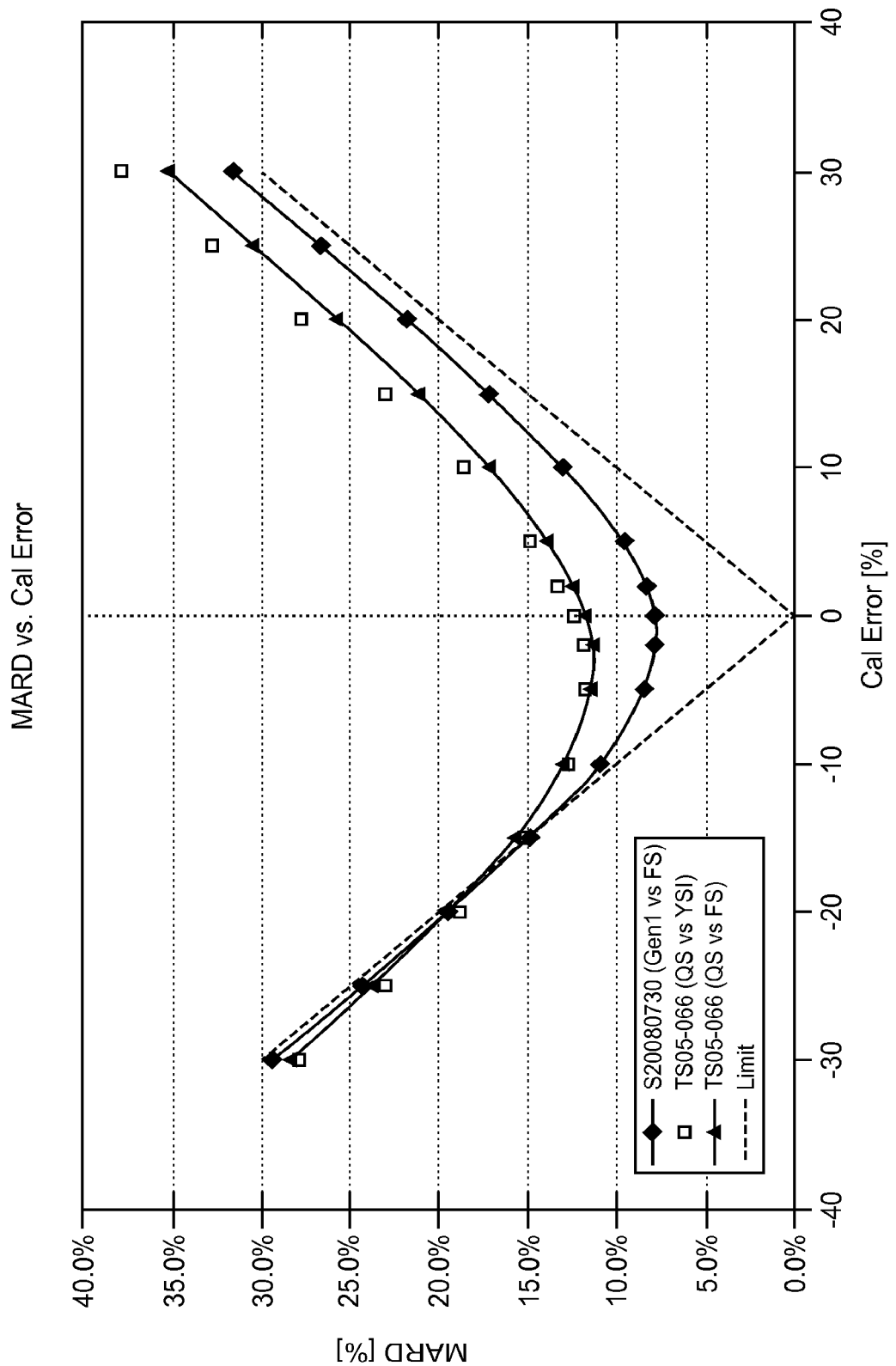
FIG. 28 provides a graph showing the effect of scaling factor/calibration error from the ideal value. TS05-066 data represents glucose date from People with Diabetes (PwD) with a large range of glucose. S20080730 represents a study dominated with People without Diabetes (PwoD), where the glucose range is very narrow.

Software Application Providing Glucose Distribution Pattern-Based Scaling Factor Sensor-based glucose monitoring generally requires a scaling factor. The reciprocal of this scaling factor is called sensitivity, wherein the raw sensor output is divided by the in-vivo sensitivity estimate in order to scale it into glucose concentration units. Depending on the glucose distribution pattern of the patient, the computed in-vivo sensitivity between a person with good and poor glucose control can vary by as much as 7.5%. Hence, a scaling factor that is optimal for a patient's current state of glucose control may be far from optimal for the same patient in the future, or for other patients. Such a difference can result in up to 7.5% Mean Absolute Relative Difference (MARD) degradation (FIG. 28) for a factory calibration based system. The present disclosure provides an application and/or method whereby: (a) an adjustable correction factor to the sensitivity is provided to minimize this effect, (b) a mapping that correlates glucose pattern and the proper correction factor is obtained based on population data, (c) online glucose pattern of the patient is estimated in order to determine the correction factor, (d) online glucose pattern estimation is predicted from the patient's glucose history, (e) a choice of several initial starting points are provided for the patient, the patient's Health Care Provider (HCP), or another suitable party to choose, and/or (f) a means to carry over the correction factor is provided so that subsequent sensor wears can benefit from prior knowledge. In the case of a completely retrospective application, no prediction is involved in the correction process.

Figure 29:
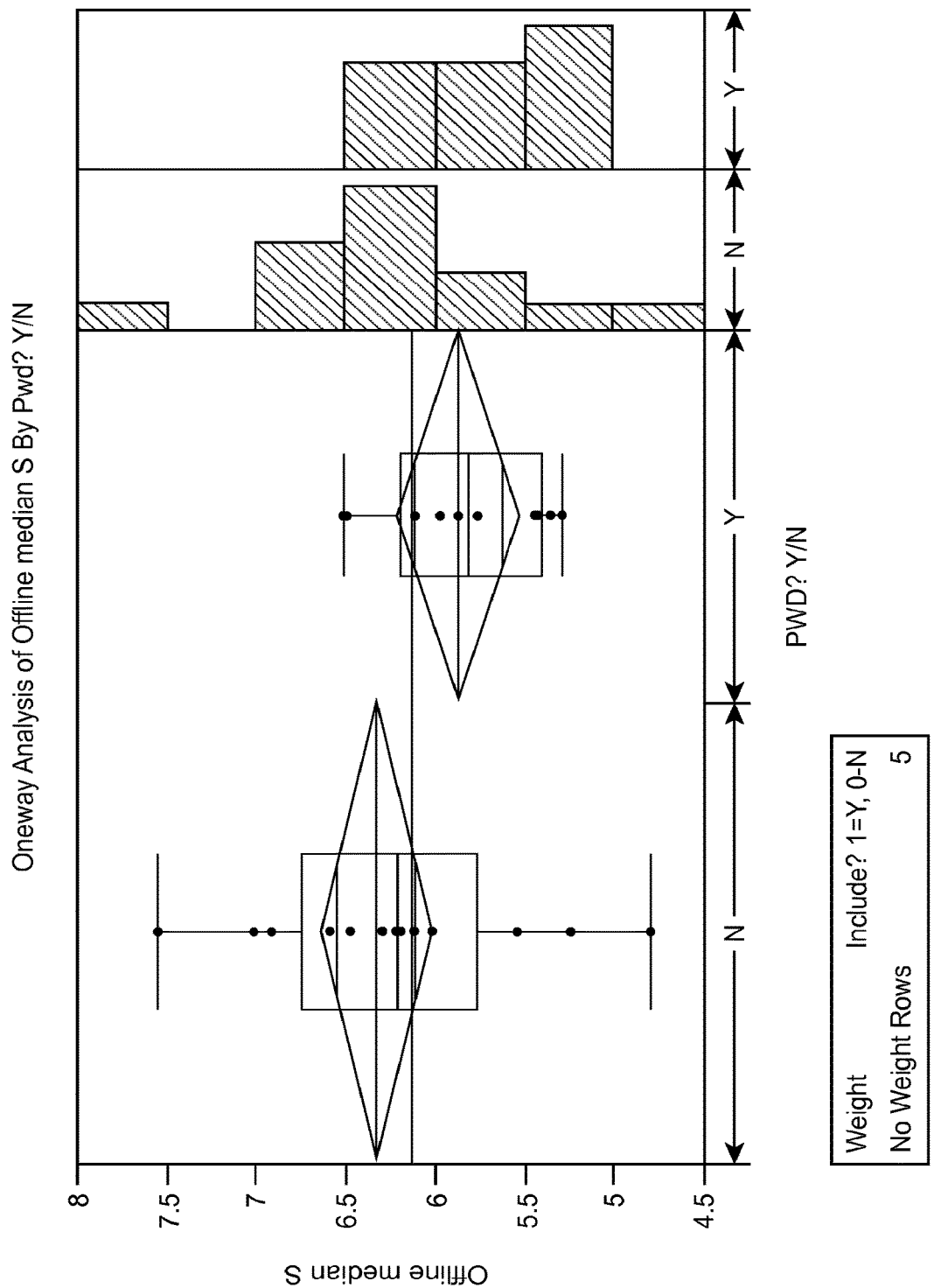
FIG. 29 shows the distribution of sensor in-vivo sensitivities estimated by taking the median of paired point sensitivities in each sensor. Values are grouped by PwoD (N) vs. PwD (Y).

For a factory calibrated system, reliable determination of in-vivo and in-vitro sensitivities are important to determine a "body-to-beaker" factor. Previously, in-vivo calibration systems circumvented this issue by directly estimating the best in-vivo (i.e. overall) sensitivity, Svivo via composite sensitivity. Observation of in-vivo sensitivities suggest a noticeable difference between those obtained from people with diabetes (PwD) and people without diabetes (PwoD). FIG. 29 shows values from 10 PwoD sensors and 8 PwD sensors from a single study, where the PwoD and PwD means are approximately 7.5% apart.

Figure 30:
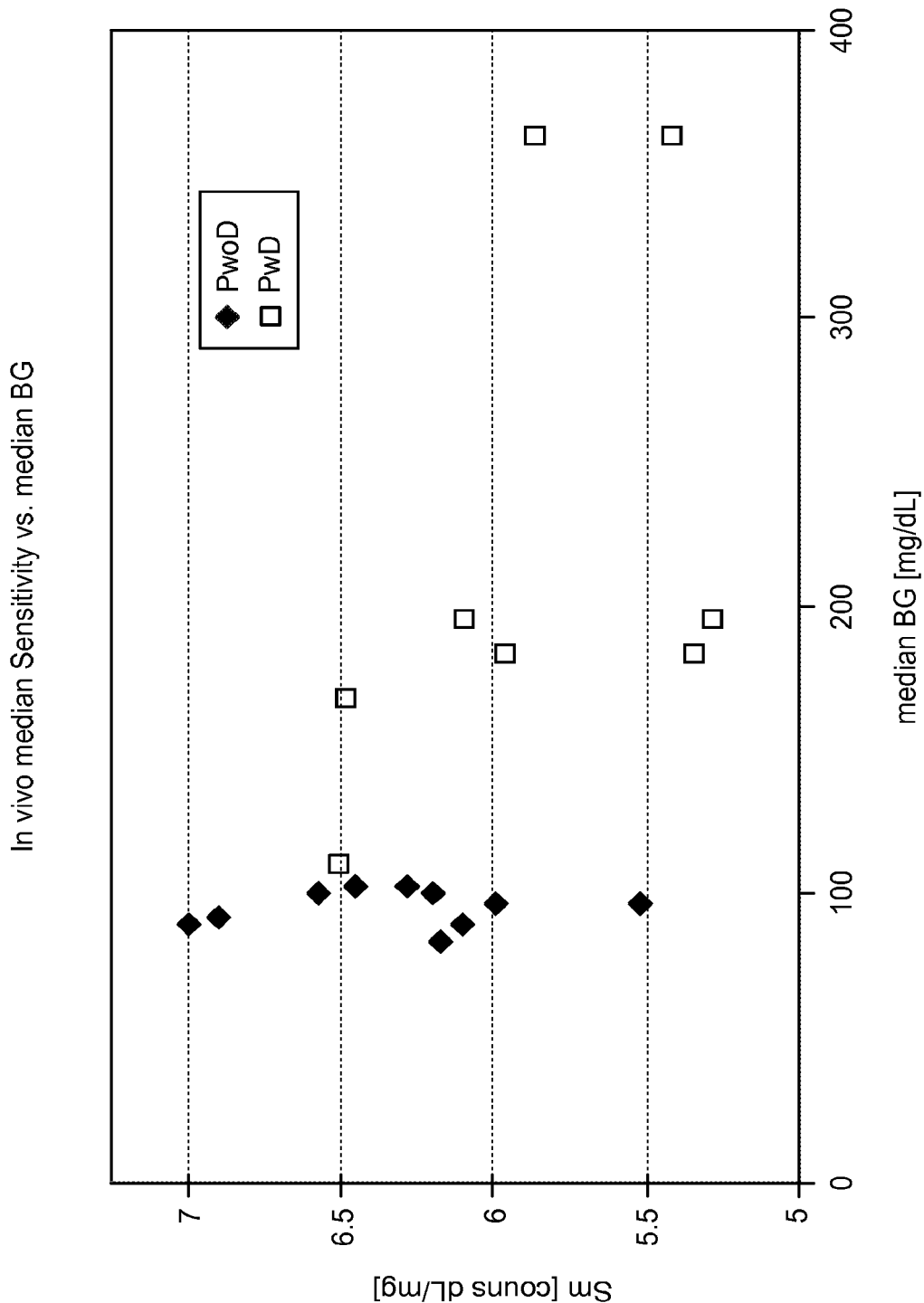
FIG. 30 provides a graph showing in-vivo sensor sensitivity (by taking the median of paired point sensitivities in each sensor) vs. median BG value for each insertion.

In addition, it can be shown that the in-vivo sensitivities are correlated to the median blood glucose (BG) value of each sensor wear (FIG. 30). A larger median BG is typically associated with a lower computed in-vivo sensitivity. When the paired point sensitivities of the same sensors used to generate plots in FIG. 29 and FIG. 30 are combined in a single plot, the result still shows a consistent trend, where sensitivities at the low end of the reference BG values tend to have a higher scatter and a positive bias compared to values at the mid and high end of the reference BG range (FIG. 31).

Figure 31:
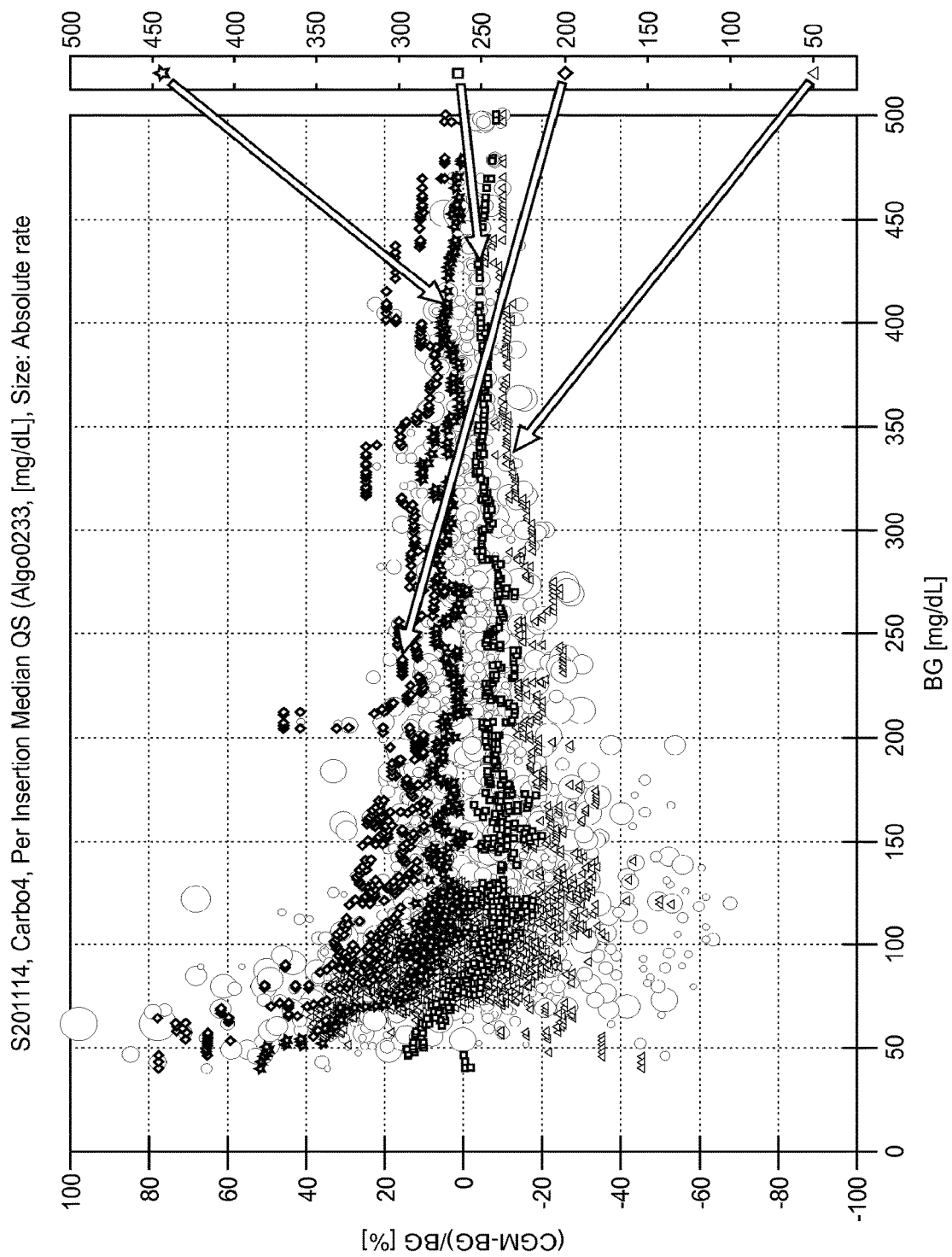
FIG. 31 provides a scatter plot of in-vivo paired point sensitivities ordered by the paired point BG value.

The dependency of mean and variability of sensitivities with respect to BG value also extends beyond the basic aggregate property exhibited in FIG. 31. Particularly, when sensitivity from each sensor is coded, and a perimeter of the scatter points for each insertion is provided (by computing a convex hull from the paired points) as shown in the left plot of FIG. 32, the extreme ends of the glucose distribution exhibits a consistent trend, where the top and bottom ends of the CGM-vs-BG plot tapers in a consistent pattern, and the sides are almost parallel to the 45 degree line. When plotted in terms of sensitivity vs. BG (right plot of FIG. 32), the low end of each insertion is consistently biased positive with a relatively higher scatter compared to the right end of each insertion, regardless of where the sensor cluster points lie. When a person's level of glucose control changes, it can be similar to moving from one set, such as the set marked "A", with a very high mean glucose, to a much better controlled state, represented by set "B". The optimal scaling factor for these two sets can differ significantly enough to impact overall sensor accuracy.

Figure 32:
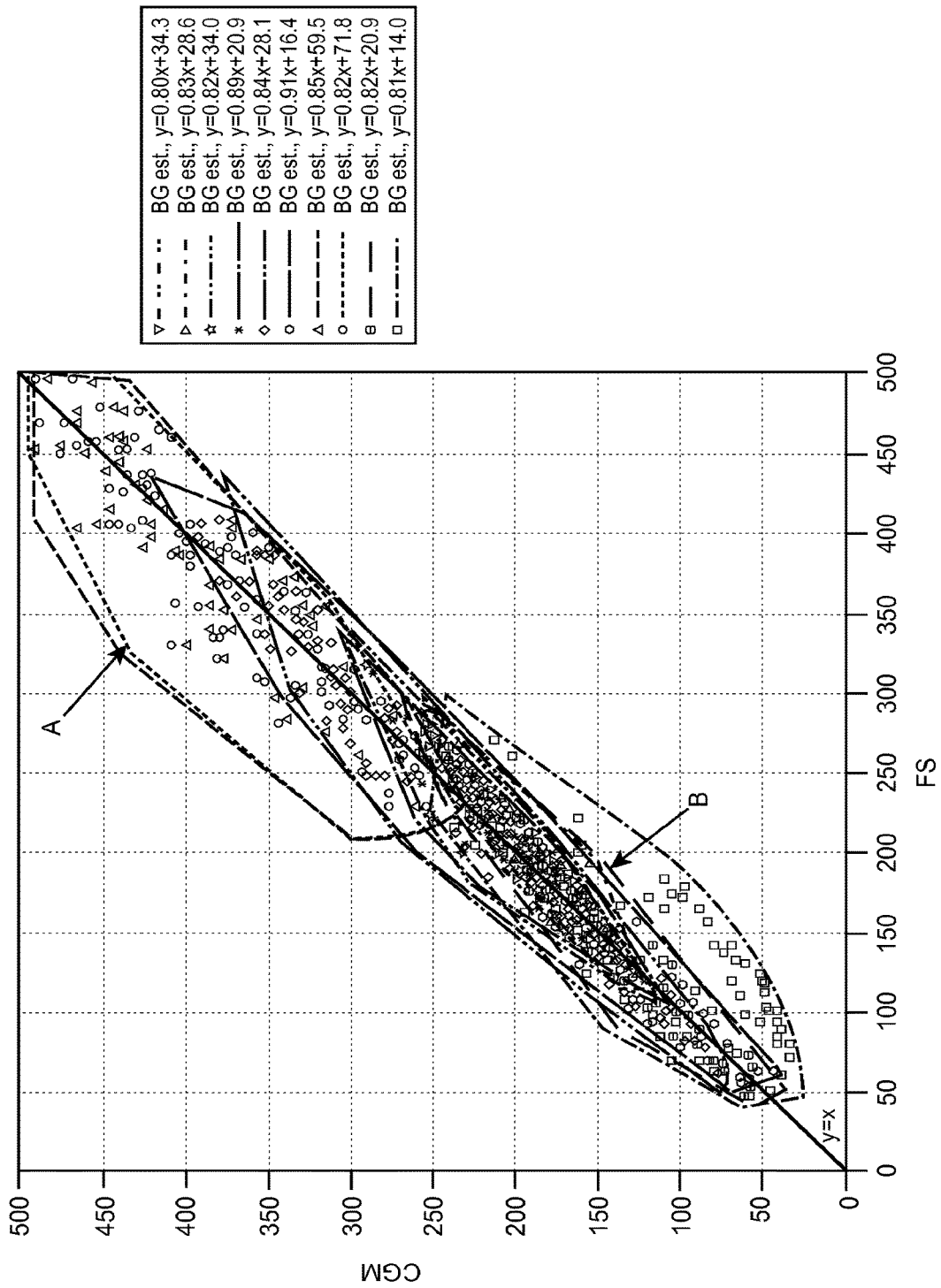
FIG. 32 provides a scatter plot of per insertion median calibrated Continuous Glucose Monitor (CGM) values vs. reference BG, coded by each insertion (left plot). Only data from PwDs are shown. The scatter for each insertion is represented by the perimeter lines. The 3 dashed perimeter lines contain exception values that overextend their lines beyond the relevant context of this discussion. The resulting sensitivities are plotted on the right, again vs. reference BG. Solid grey lines (C) correspond to constant CGM lines from the left plot, while dashed grey lines (D) correspond to 45 degree lines with various offsets from the intercept of the left plot.
Figure 32:
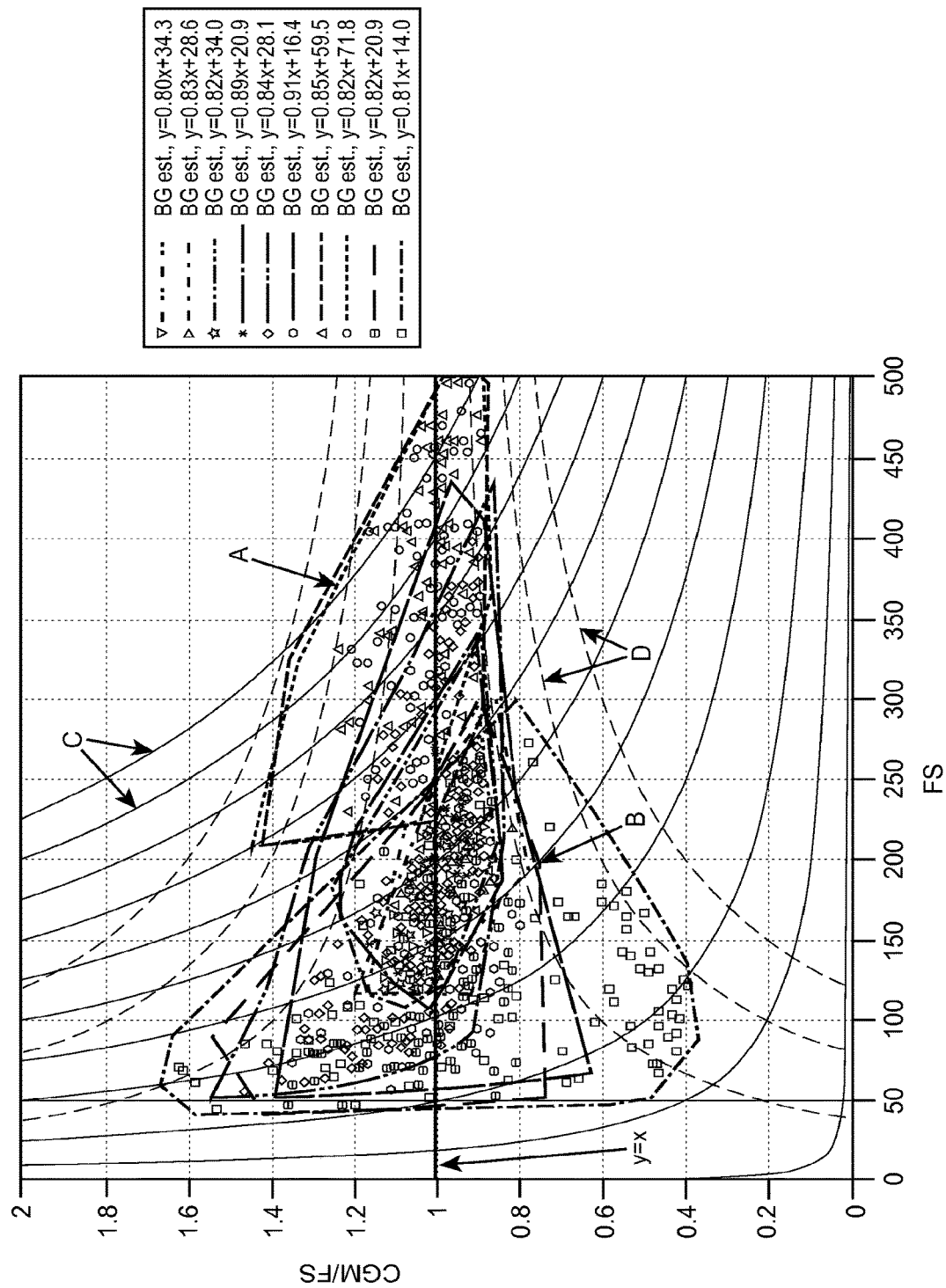

An offline map between a patient's glucose pattern and the necessary correction factor can be constructed using data shown in FIG. 32. For example, correlations can be made between the relative in-vivo sensitivity of each sensor with the median BG value of each sensor. In addition, secondary factors such as BG range, or other measurable factors, can be added into the correlation data. The result is a function or a lookup table that allows the sensor's calibration factor to be further optimized to each patient's current state of glucose control.

In one embodiment, the present disclosure provides an application and/or method which includes determining a correction factor to a sensor calibration factor based on a pre-determined map between optimal calibration factors and a patient's glucose distribution pattern, wherein:
   a) the correction factor is based on the relative values of the optimal calibration factors in the map,
   b) the correction factor is applied to a pre-determined calibration factor of a sensor,
   c) the pre-determined calibration factor of the sensor was made without prior knowledge of a patient's glucose distribution pattern, and
   d) the correction factor provides an adjustment to the calibration factor in response to the patient's glucose distribution pattern.

In one embodiment, the patient's glucose distribution pattern is determined based on glucose data within a pre-determined window of time relative any instance. The term "instance" in this context refers to the particular data point that is being corrected. For example, in a real-time system, when each new data point is received (an "instance"), the data are taken for a period of time prior to and including this most recent datum, and these data are processed to determine the correction factor to be applied to this most recent data point. For a retrospective system, for each data point (or "instance"), the data are taken for a period of time that can span prior to and after the most recent point, and these data are processed to determine the correction factor to be applied to this data point. Additional variations are possible, e.g., a period may be defined for a group of adjacent data points, the data in this period processed to determine a correction factor, and this correction factor applied to the group of adjacent data points.

For example, in one embodiment, the patient's glucose distribution pattern is determined based on glucose data within a pre-determined window of time around any instance (e.g. no longer than 48, 24 or 12 hours from any instance).

In one embodiment, the glucose distribution pattern is represented by the steady-state glucose value and the glucose range within the pre-determined window of time. In one such embodiment, the steady-state glucose value is determined by taking the average, median, or average of the upper and lower quartiles of the glucose values within the pre-determined window of time. The glucose range may be determined by taking the difference between the maximum and minimum, distance between the upper and lower quartiles, or the standard deviation of the glucose values within the pre-determined window of time.

In one embodiment, the patient's glucose distribution pattern is determined based on a pre-determined window of time up to any instance, but excluding any future instances.

In one embodiment, a history of the patient's glucose distribution pattern is tracked by employing more than one window of time using data from the past and up to the present, wherein:
   a) a history of one or more parameters associated with the patient's glucose distribution is determined and ordered by the representative timestamps of each historical window,
   b) the trend of the one or more parameters across the timestamps are used to estimate the values of the current one or more parameters, and
   c) the estimated values of the current one or more parameters are used in conjunction with the pre-determined map between optimal calibration factors and the patient's glucose distribution pattern.

In one embodiment, where the history of the patient's glucose distribution pattern is tracked by employing more than one window of time using data from the past and up to the present as described above, the trend of the one or more parameters across the timestamps are generated by computing a linear fit of the available values and their associated timestamps, and computing the value predicted by the linear fit onto a projected near future.

In one embodiment, where the history of the patient's glucose distribution pattern is tracked by employing more than one window of time using data from the past and up to the present as described above, the trend of the one or more parameters across the timestamps are generated by determining a second order polynomial fit of the available values and their associated timestamps, and determining the value predicted by the polynomial fit onto a projected near future.

In one embodiment, where the history of the patient's glucose distribution pattern is tracked by employing more than one window of time using data from the past and up to the present as described above, the trend of the one or more parameters across the timestamps are generated by utilizing a particle filter to smoothly track the one or more parameters and to determine an estimate of the values in a projected near future.

In one embodiment, a choice of several initial starting values representative of a patient's level of glucose control (e.g. high average BG with low variability, low average BG with low variability, high average BG with high variability, etc.) can be selected based on the patient, the patient's HCP or other suitable party's assessment of the patient's level of glucose control.

In one embodiment, the correction factor is retained in memory (e.g., the memory of an on-body and/or hand-held component of a CGM system) to be used as an initial correction factor for the next sensor wear by the same patient.

Integration with Medication Delivery Devices and/or Systems

In some embodiments, the analyte measurement systems disclosed herein may be included in and/or integrated with, a medication delivery device and/or system, e.g., an insulin pump module, such as an insulin pump or controller module thereof, or insulin injection pen. In some embodiments the analyte measurement system is physically integrated into a medication delivery device. In other embodiments, an analyte measurement system as described herein may be configured to communicate with a medication delivery device or another component of a medication delivery system. Additional information regarding medication delivery devices and/or systems, such as, for example, integrated systems, is provided in U.S. Patent Publication No. 2006/0224141, published on Oct. 5, 2006, entitled "Method and System for Providing Integrated Medication Infusion and Analyte Monitoring System", and U.S. Patent Publication No. 2004/0254434, published on Dec. 16, 2004, entitled "Glucose Measuring Module and Insulin Pump Combination," the disclosure of each of which is incorporated by reference herein in its entirety. Medication delivery devices which may be provided with analyte measurement system as described herein include, e.g., a needle, syringe, pump, catheter, inhaler, transdermal patch, or combination thereof. In some embodiments, the medication delivery device or system may be in the form of a drug delivery injection pen such as a pen-type injection device incorporated within the housing of an analyte measurement system. Additional information is provided in U.S. Pat. Nos. 5,536,249 and 5,925,021, the disclosures of each of which are incorporated by reference herein in their entirety.

The embodiments presented herein provide further advantages such as: the ability to upgrade strip port modules as new test strip technologies evolve; the ability to clean or sterilize a strip port module; and the ability to allow users to replace strip port modules without returning the entire measurement system to the manufacture.

Certain embodiments relate to in vivo (e.g., continuous monitoring) systems. A continuous monitoring system typically includes a sensor that is worn or placed below the skin, a transmitter that collects glucose information from the sensor, and a receiver that collects the information from the transmitter. The sensor can collect glucose level information continuously, periodically, or at other intervals. Advantageously, a user is relieved from having to repeatedly lance his or her body to collect a blood sample once the sensor is inserted, although the sensor (e.g., an electrochemical sensor that is inserted into a body) can be replaced. U.S. Pat. No. 6,175,752, which is hereby incorporated by reference in its entirety, discloses additional examples of a continuous monitoring system.

Embodiments of the invention relate to components of a continuous monitoring system that may be replaceable. In one embodiment, the interface between the sensor and the transmitter may become contaminated. The transmitter or sensor control unit, for example, may have an interface with the sensor that has been molded to form a barrier between the transmitter's contacts and circuitry internal to the transmitter. This allows the transmitter's contacts to be washed without damaging the transmitter's circuitry. Alternatively, the contacts may be included in a replaceable port that can be replaced as needed. Similarly, the interface on the sensor may be molded to form a barrier to contamination or be replaceable.

Embodiments of the invention further extend to kits. Examples of a kit include a measurement device with one or more strip connectors. In some kits, different strip connectors or ports for different types of strips may be included. This allows the measurement device to be used with different strip form factors. The kits may also include a plurality of test strips. In certain examples, the measurement device may be configured for use with disposable test strips as well as with test strips that are configured for continuous monitoring systems. Thus, the measurement device may include a receiver to receive information from a transmitter that collects glucose information from an inserted sensor. The measurement device may also include a strip connector, such as those disclosed herein, for use with single use test strips.

Analyte Test Strips

Analyte test strips for use with the present devices can be of any kind, size, or shape known to those skilled in the art; for example, FREESTYLE® and FREESTYLE LITE™ test strips, as well as PRECISION™ test strips sold by ABBOTT DIABETES CARE Inc. In addition to the embodiments specifically disclosed herein, the devices of the present disclosure can be configured to work with a wide variety of analyte test strips, e.g., those disclosed in U.S. patent application Ser. No. 11/461,725, filed Aug. 1, 2006; U.S. Patent Publication No. 2007/0095661; U.S. Patent Publication No. 2006/0091006; U.S. Patent Publication No. 2006/0025662; U.S. Patent Publication No. 2008/0267823; U.S. Patent Publication No. 2007/0108048; U.S. Patent Publication No. 2008/0102441; U.S. Patent Publication No. 2008/0066305; U.S. Patent Publication No. 2007/0199818; U.S. Patent Publication No. 2008/0148873; U.S. Patent Publication No. 2007/0068807; U.S. patent application Ser. No. 12/102,374, filed Apr. 14, 2008, and U.S. Patent Publication No. 2009/0095625; U.S. Pat. Nos. 6,616,819; 6,143,164; 6,592,745; 6,071,391 and 6,893,545; the disclosures of each of which are incorporated by reference herein in their entirety.

Calculation of Medication Dosage

In one embodiment, the analyte measurement system may be configured to measure the blood glucose concentration of a patient and include instructions for a long-acting insulin dosage calculation function. Periodic injection or administration of long-acting insulin may be used to maintain a baseline blood glucose concentration in a patient with Type-1 or Type-2 diabetes. In one aspect, the long-acting medication dosage calculation function may include an algorithm or routine based on the current blood glucose concentration of a diabetic patient, to compare the current measured blood glucose concentration value to a predetermined threshold or an individually tailored threshold as determined by a doctor or other treating professional to determine the appropriate dosage level for maintaining the baseline glucose level. In one embodiment, the long-acting insulin dosage calculation function may be based upon LANTUS® insulin, available from Sanofi-Aventis, also known as insulin glargine. LANTUS® is a long-acting insulin that has up to a 24 hour duration of action. Further information on LANTUS® insulin is available at the website located by placing "www" immediately in front of ".lantus.com". Other types of long-acting insulin include Levemir® insulin available from NovoNordisk (further information is available at the website located by placing "www" immediately in front of ".levemir-us.com". Examples of such embodiments are described in US Patent Publication No. 2010/01981142, the disclosure of which is incorporated herein by reference in its entirety.

Strip Port Configured to Receive Test Strips for Different Analytes

In another embodiment, there is provided an analyte measurement system for multichemistry testing. The test strips are for chemical analysis of a sample, and are adapted for use in combination with a measuring device having a test port and capable of performing a multiplicity of testing functionalities. Each type of test strip corresponds to at least one of the testing functionalities, and at least some types of test strips have indicators of the testing functionality on them. The test port is adapted for use in combination with a multiplicity of different types of test strips and includes a sensor capable of specifically interacting with the indicator(s) on the test strips, thereby selecting at least one of the multiplicity of testing functionalities corresponding to the type of test strip. Such system would include a strip port that can be used to read a test strip for glucose and a test strip for ketone bodies. Examples of such embodiment are provided in U.S. Pat. No. 6,773,671, which is incorporated herein by reference in its entirety.

Strip Port Configured to Receive Test Strips Having Different Dimensions and/or Electrode Configurations In some embodiments, an analyte measurement system as described herein includes a strip port configured to receive test strips having different dimensions and/or electrode configurations, e.g., as described in the U.S. patent application Ser. No. 12/695,947 filed on Jan. 28, 2010, and entitled "Universal Test Strip Port", the disclosure of which is incorporated by reference herein in its entirety.

Implanted Analyte Sensor

In some embodiments, an analyte measurement system as described herein may include an implanted or partially implanted analyte sensor, e.g., a system including an implanted or partially implanted glucose sensor (e.g., a continuous glucose sensor). A system including an implanted or partially implanted glucose sensor may include an analyte measurement system as described herein, which is configured to receive analyte data from the implanted or partially implanted glucose sensor either directly or through an intermediate device, e.g., an RF-powered measurement circuit coupled to an implanted or partially implanted analyte sensor. In some embodiments, where an analyte measurement system according to the present disclosure is integrated with an implanted sensor, the analyte measurement system does not include a strip port for receiving an analyte test strip. In one embodiment, the analyte measurement system may be used to calibrate the analyte monitoring system, e.g., using one point calibration or other calibration protocol. For additional information, see U.S. Pat. No. 6,175,752, the disclosure of which is incorporated by reference herein in its entirety. In some embodiments, the analyte measurement system may be configured to communicate with the implanted or partially implanted analyte sensor via Radio Frequency Identification (RFID) and provide for intermittent or periodic interrogation of the implanted analyte sensor.

Exemplary analyte monitoring systems that may be utilized in connection with the disclosed analyte measurement system include those described in U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Publication No. 2004/0186365; U.S. Patent Publication No. 2007/0095661; U.S. Patent Publication No. 2006/0091006; U.S. Patent Publication No. 2006/0025662; U.S. Patent Publication No. 2008/0267823; U.S. Patent Publication No. 2007/0108048; U.S. Patent Publication No. 2008/0102441; U.S. Patent Publication No. 2008/0066305; U.S. Patent Publication No. 2007/0199818; U.S. Patent Publication No. 2008/0148873; U.S. Patent Publication No. 2007/0068807; U.S. Patent Publication No. 2010/0198034; and U.S. Provisional Application No. 61/149,639 titled "Compact On-Body Physiological Monitoring Device and Methods Thereof", the disclosures of each of which are incorporated herein by reference in their entirety.

Communication Interface

As discussed previously herein, an analyte measurement system according to the present disclosure can be configured to include a communication interface. In some embodiments, the communication interface includes a receiver and/or transmitter for communicating with a network and/or another device, e.g., a medication delivery device and/or a patient monitoring device, e.g., a continuous glucose monitoring device. In some embodiments, the communication interface is configured for communication with a health management system, such as the CoPilot™ system available from Abbott Diabetes Care Inc., Alameda, CA The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the analyte measurement system and other external devices such as a computer terminal (for example, at a physician's office or in hospital environment), an external medical device, such as an infusion device or including an insulin delivery device, or other devices that are configured for similar complementary data communication.

In one embodiment, the communication interface is configured for infrared communication, Bluetooth® communication, or any other suitable wireless communication protocol to enable the analyte measurement system to communicate with other devices such as infusion devices, analyte monitoring devices, computer terminals and/or networks, communication enabled mobile telephones, personal digital assistants, or any other communication devices which the patient or user of the analyte measurement system may use in conjunction therewith, in managing the treatment of a health condition, such as diabetes.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the analyte measurement system is configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the analyte measurement system indirectly by interacting with the user interface(s) of the server device, which in turn interacts with the analyte measurement system across a wireless link.

In some embodiments, the communication interface is configured to automatically or semi-automatically communicate data stored in the analyte measurement system, e.g., in an optional data storage unit, with a network or server device using one or more of the communication protocols and/or mechanisms described above.

Input Unit

As discussed previously herein, an analyte measurement system according to the present disclosure can be configured to include an input unit and/or input buttons coupled to the housing of the analyte measurement system and in communication with a controller unit and/or processor. In some embodiments, the input unit includes one or more input buttons and/or keys, wherein each input button and/or key is designated for a specific task. Alternatively, or in addition, the input unit may include one or more input buttons and/or keys that can be 'soft buttons' or 'soft keys'. In the case where one or more of the input buttons and/or keys are 'soft buttons' or 'soft keys', these buttons and/or keys may be used for a variety of functions. The variety of functions may be determined based on the current mode of the analyte measurement system, and may be distinguishable to a user by the use of button instructions shown on an optional display unit of the analyte measurement system. Yet another input method may be a touch-sensitive display unit, as described in greater detail below.

In addition, in some embodiments, the input unit is configured such that a user can operate the input unit to adjust time and/or date information, as well as other features or settings associated with the operation of an analyte measurement system.

Display Unit

As discussed previously herein, in some embodiments, an analyte measurement system according to the present disclosure includes an optional display unit or a port for coupling an optional display unit to the analyte measurement system. The display unit is in communication with a control unit and/or processor and displays the analyte test strip signals and/or results determined from the analyte test strip signals including, for example, analyte concentration, rate of change of analyte concentration, and/or the exceeding of a threshold analyte concentration (indicating, for example, hypo- or hyperglycemia).

The display unit can be a dot-matrix display, e.g., a dot-matrix LCD display. In some embodiments, the display unit includes a liquid-crystal display (LCD), thin film transistor liquid crystal display (TFT-LCD), plasma display, light-emitting diode (LED) display, seven-segment display, E-ink (electronic paper) display or combination of two or more of the above. The display unit can be configured to provide, an alphanumeric display, a graphical display, a video display, an audio display, a vibratory output, or combinations thereof. The display can be a color display. In some embodiments, the display is a backlit display.

The display unit can also be configured to provide, for example, information related to a patient's current analyte concentration as well as predictive analyte concentrations, such as trending information.

In some embodiments an input unit and a display unit are integrated into a single unit, for example, the display unit can be configured as a touch sensitive display, e.g., a touch-screen display, where the user may enter information or commands via the display area using, for example, the user's finger, a stylus or any other suitable implement, and where, the touch sensitive display is configured as the user interface in an icon driven environment, for example.

In some embodiments, the display unit does not include a screen designed to display results visually. Instead, in some embodiments the optional display unit is configured to communicate results audibly to a user of the analyte measurement system, e.g., via an integrated speaker, or via separate speakers through a headphone jack or Bluetooth® headset.

Expanding Menu Item for Improved Readability

In some embodiments, the display unit includes a graphical user interface including a plurality of menu items, wherein the display unit is configured to provide clarification with respect to the meaning of a menu item based on a user's response speed with respect to a user input for the menu item. The menu item may take any of a variety of forms, e.g., text, icon, object or combination thereof.

In one embodiment, the graphical user interface includes a menu which in turn includes a plurality of selectable menu items. As a user navigates through the menu, e.g., by highlighting or scrolling through individual menu items, a menu item that is either unreadable or incomprehensible to the user may cause the user to pause over a menu item to be selected. In one embodiment, a choice can be presented to the user, e.g., using a dedicated physical button on an input unit, or a soft key on the menu, that offers further explanation of the item to be selected without actually selecting the item. For example, the graphical user interface can be configured such that after a pre-determined period of time a soft key offers an explanation of the menu item to be selected, e.g., by displaying a soft key with the word "MORE", "ADDITIONAL INFORMATION", "EXPAND", "MAGNIFY", "HELP" or a variation thereof displayed thereon.

The pre-determined period of time may be based on a fixed factory preset value, a value set by the user or a health care provider, or through an adaptive mechanism based on an analysis of the user's speed of navigation from past interactions with the graphical user interface. In one embodiment, the pre-determined period of time is from about 5 to about 20 seconds, e.g., from about 10 to about 15 seconds.

If the offer for clarification and/or additional information is selected, e.g., by pressing the softkey, then the menu item to be selected can be displayed in a "high emphasis" mode, e.g., where the item is displayed as if a magnifying lens is held on top of the selected item. In some embodiments, additional emphasis of the menu item to be selected can be provided, e.g., by making the menu item change color, blink, or increase in size to a pre-determined maximum limit.

Support for On-Demand Analyte Determination Using an Analyte Sensor

In some embodiments, an analyte measurement system according to the present disclosure is further configured to receive analyte concentration data and/or signals indicative of an analyte concentration from an analyte sensor, e.g., an implanted or partially implanted analyte sensor or a radio-frequency (RF)-powered measurement circuit coupled to an implanted or partially implanted analyte sensor. In some embodiments, the analyte sensor is a self-powered analyte sensor. An analyte measurement system according to the present disclosure may include software configured to analyze signals received from the analyte sensor. Additional information related to self-powered analyte sensors and methods of communicating therewith are provided in U.S. Patent Publication No. 2010/0213057, the disclosure of which is incorporated by reference herein in its entirety.

Analytes

A variety of analytes can be detected and quantified using the disclosed analyte measurement system. Analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. Nos. 6,281,006 and 6,638,716, the disclosures of each of which are incorporated by reference herein in their entirety.

Conclusion

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

The detailed description of the figures refers to the accompanying drawings that illustrate an exemplary embodiment of an analyte measurement system. Other embodiments are possible. Modifications may be made to the embodiment described herein without departing from the spirit and scope of the present invention. Therefore, the following detailed description is not meant to be limiting.

Certain embodiments presented herein relate to electrical interfaces in measurement devices. Measurement devices often have electrical interfaces that allow them to electrically connect with another device or apparatus and perform an analysis of an analyte. A device that measures blood glucose levels, for example, includes electrical interfaces that allow the device to measure the blood glucose level from a small blood sample.

What is claimed is:

1. An analyte monitoring system, comprising:
an analyte measurement device configured to receive data indicative of an analyte level from an in vivo sensor, the analyte measurement device comprising a processor and a computer-readable storage medium having a software application stored thereon, wherein the software application includes a tagging mode, and wherein the software application, when executed, causes the processor to:
in response to an analyte measurement result being outside of a target analyte range for a user, automatically display the analyte measurement result, wherein the target analyte range comprises a lower limit and an upper limit, and wherein the analyte measurement result is based on the data indicative of the analyte level; and
automatically display a tagging input interface in real time in response to (1) the tagging mode being enabled and (2) the analyte measurement result being outside of the target analyte range for the user, wherein the tagging input interface is configured to prompt the user to tag the analyte measurement result, wherein the tagging mode is enabled according to a predetermined schedule comprising predefined time periods, wherein the tagging input interface is not displayed if the analyte measurement result is within the target range,
wherein the analyte measurement result is displayed in response to the analyte measurement result being outside of the target analyte range without displaying the tagging input interface when the tagging mode is disabled.

2. The analyte monitoring system of claim 1, wherein the software application, when executed, causes the processing device to automatically cause display of the tagging input interface that requests the user tag the analyte measurement result with a tag selected from the group comprising: fasting, pre-meal, or post-meal.

3. The analyte monitoring system of claim 1, wherein the software application, when executed, causes the processing device to automatically cause display of the tagging input interface that requests the user tag the analyte measurement result with a tag selected from the group comprising: a meal or a fasting period.

4. The analyte monitoring system of claim 1, wherein the software application, when executed, causes the processing device to automatically cause display of the tagging input interface that requests the user tag the analyte measurement result with a tag selected from the group comprising: a drug administration, a drug amount, or a meal amount.

5. The analyte monitoring system of claim 1, wherein the software application, when executed, causes the processing device to record the tag as a time-stamped event.

6. The analyte monitoring system of claim 1, wherein the software application, when executed, causes the processing device to cause display of a reminder for the user to enter information, wherein the information is selected from the group comprising: a time of a meal, an amount of a meal, a time of a bolus, or an amount of a bolus.

7. The analyte monitoring system of claim 6, wherein the software application, when executed, causes the processing device to cause display of the reminder during each of a plurality of predefined time periods.

8. The analyte monitoring system of claim 7, wherein the plurality of predefined time periods comprise a morning time period, a mid-day time period, and an evening time period.

9. The analyte monitoring system of claim 7, wherein the information is associated with each of the plurality of predefined time periods, and wherein the software application, when executed, causes the processing device to cause display of the reminder during each of a plurality of predefined time periods only if the information associated with that predefined time period has not been entered.

10. The analyte monitoring system of claim 1, wherein the analyte measurement result is a glucose measurement result.

11. The analyte monitoring system of claim 1, wherein the software application, when executed, causes the processing device to determine whether the analyte measurement result is outside the target analyte range for the user.

12. The analyte monitoring system of claim 11, wherein the tagging input interface is automatically caused to be displayed only if the analyte measurement result is determined to be outside of the target analyte range for the user and only if the at least one processing device is operating in a first mode, wherein the software application, when executed, causes the processing device to automatically operate in the first mode based on a health care professional office visit reminder.

* * * * *